United States Patent
Facchini et al.

(10) Patent No.: US 11,560,578 B2
(45) Date of Patent: Jan. 24, 2023

(54) NEOPINONE ISOMERASE AND METHODS OF USING

(71) Applicant: Antheia, Inc., Menlo Park, CA (US)

(72) Inventors: Peter J. Facchini, Calgary (CA); Xue Chen, Calgary (CA)

(73) Assignee: Antheia, Inc., Menlo Park, CA (US)

( * ) Notice: Subject to any disclaimer, the term of this patent is extended or adjusted under 35 U.S.C. 154(b) by 0 days.

(21) Appl. No.: 16/770,207

(22) PCT Filed: Nov. 29, 2018

(86) PCT No.: PCT/CA2018/051520
§ 371 (c)(1),
(2) Date: Jun. 5, 2020

(87) PCT Pub. No.: WO2019/109170
PCT Pub. Date: Jun. 13, 2019

(65) Prior Publication Data
US 2020/0291438 A1    Sep. 17, 2020

Related U.S. Application Data

(60) Provisional application No. 62/594,854, filed on Dec. 5, 2017, provisional application No. 62/686,337, filed on Jun. 18, 2018.

(51) Int. Cl.
*C12N 9/90* (2006.01)
*C12P 17/18* (2006.01)

(52) U.S. Cl.
CPC ................................. *C12P 17/18* (2013.01)

(58) Field of Classification Search
CPC ........ C12N 9/90; A61K 31/485; C07D 489/02
See application file for complete search history.

(56) References Cited

U.S. PATENT DOCUMENTS 11,142,780 B2 * 10/2021 Facchini ............... C12P 17/182
2018/0163241 A1    6/2018 Smolke et al.

FOREIGN PATENT DOCUMENTS

WO    2018005553 A1    1/2018
WO    2019165551 A1    9/2019

OTHER PUBLICATIONS

Hodges et al. 1980; Enzymatic reductions of codeinone in vitro cell-systems from Papaver somniferum and P. bracteatum. Phytochemistry. vol. 19, pp. 1681-1684.*
Siah et al. 1991; Enhanced codeine and morphine production in suspended Papaver somniferum cultures after removal of exogenous hormones. Plant Cell Reports, vol. 10, pp. 349-353.*
Thodey et al., "A microbial biomanufacturing platform for natural and semisynthetic opioids", Nature Chemical Biology, vol. 10, www.nature.com/naturechemicalbiology, DOI: 10.1038/NCHEMBIO. 1613, Aug. 24, 2014, 10 pages.
Fossati et al., "Synthesis of Morphinan Alkaloids in *Saccharomyces cerevisiae*", Plos One, DOI: 10.1371/journal.pone.0124459, Apr. 23, 2015, 15 pages.
Dastmalchi et al., "Neopinone isomerase is involved in codeine and morphine biosynthesis in opium poppy", Nature Chemical Biology, vol. 15, www.nature.com/naturechemicalbiology, https://doi.org/10. 1038/s41589-019-0247-0, Apr. 2019, 13 pages.
Beaudoin, "Characterization of Oxidative Enzymes Involved in the Biosynthesis of Benzylisoquinoline Alkaloids in Opium Poppy (*Papaver somniferum*)", University of Calgary, Calgary, AB, unpublished doctoral thesis, DOI: 10.11575/PRISM/25284, https://prism. ucalgary.ca, Mar. 16, 2015, 410 pages.

* cited by examiner

*Primary Examiner* — Karen Cochrane Carlson
(74) *Attorney, Agent, or Firm* — Mintz, Levin, Cohn, Ferris, Glovsky and Popeo, P.C.

(57) ABSTRACT

Disclosed are methods for converting a first morphinan alkaloid compound into a second morphinan alkaloid compound in the presence of a neopinone isomerase enzyme under reaction conditions permitting the conversion of the first alkaloid compound into the second alkaloid compound. The first alkaloid compound can be neopinone or neomorphinone. The second alkaloid compound can be codeinone or morphinone. Related compositions are also disclosed.

10 Claims, 16 Drawing Sheets

Specification includes a Sequence Listing.

Thebaine

Neopinone

Neopine

Codeinone

Oripavine

Neomorphinone

Neomorphine

Morphinone

Codeine

Morphine

Hydrocodone

14-Hydroxycodeinone

Oxycodone

14-Hydroxymorphinone

Oxymorphone

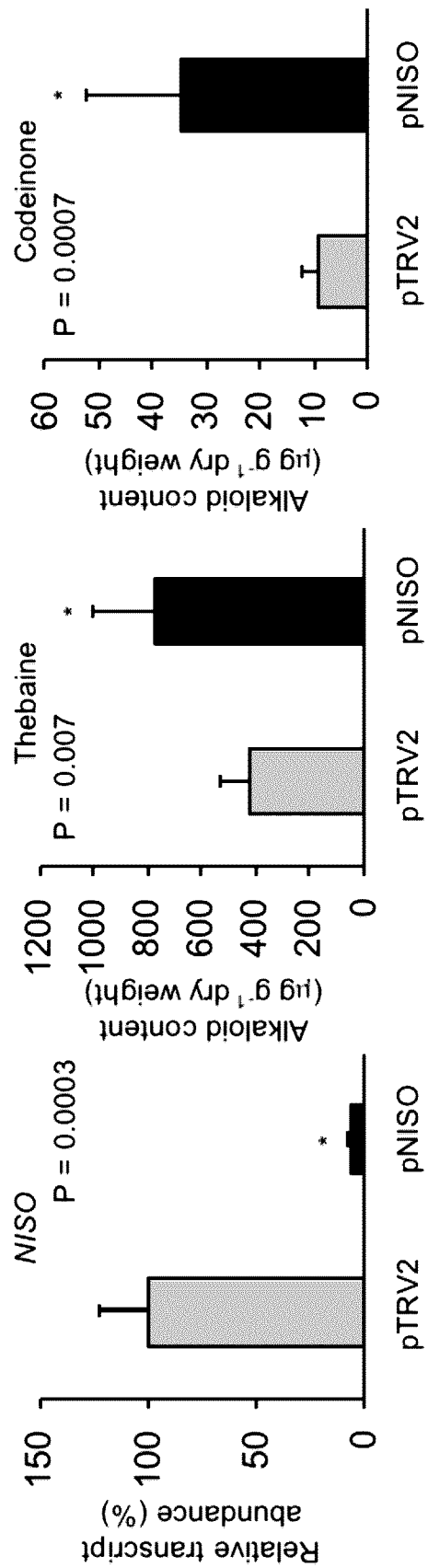
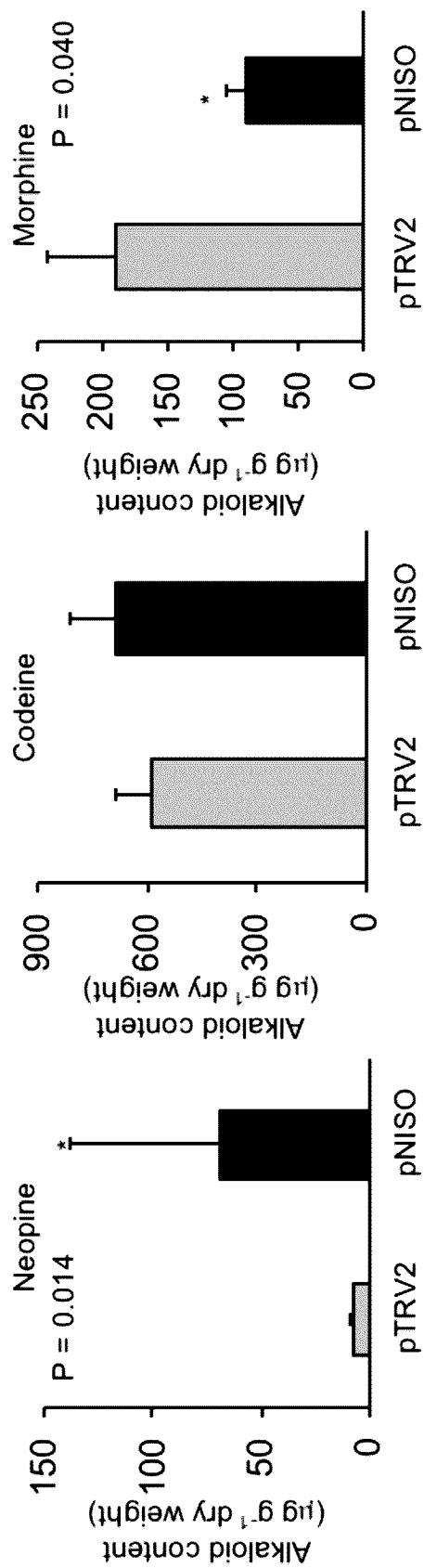
FIG. 10A, FIG. 10B, FIG. 10C, FIG. 10D, FIG. 10E, FIG. 10F

```
NISO                                           MDSV-SAALVEH----SSIY-LCA    18
THS2                                           MDSINSSIY-ECAYFRELIIK -L    22
                                              1a        1      1b

NISO     MA-H-HGVSGLVGKIVTELEVNCNADEFYKILKRDEDVER-AVSDLFPPVKIAKGDGLVSG     76
PR10-8   MA-H-HGVSGLVGKLVTQLEVNCDADEFYKIWKHHEEVPK-AVSHFPAVKVVKGDGLVSG      58
PR10-9   MA-H-HGVSGLVGKLVTQLEVNCDADKLYKIYKHHEDVPK-AISHLFTGVKVLEGHGLRSG     58
PR10-10  MA-H-HGVSGLVGKLVTQLEVNCDADIFYKIVKHHEEVPN-VIPHFFTGVQVTKGDGLVSG     58
PR10-5   MA-H-HGVSGLVGKLVTELEVHCNADAYYKIFKHQEDVPK-AMPHLYTGGKVISGDATRSG     58
PR10-4   MA-EPHPISGLVGKLVTELEVNCDADKYYKIFKHHEDVPK-AVPHMYTSVKVVEGHGITSG     59
PR10-11  MA-HTRGISGLVGKLVMETEVNCNADKYYQLYKHHEDLPS-AIPHIVTSAKAVEGHGTTSG     59
PR10-12  MARH--GGSGLVGKLVTELEVYCDADKYYKIWKHHEDVPK-AMPHMFTGVQPIKGDGICSG     58
MLP15    MA-HQHTISGLVGKLITESEVNCNADKYYQIFKHHEDLPS-AIPHIYTSVKAVEGHGTTSG     59
MLP1     MMA-H-HGVSGLVGKVVTELELNCDADEYYKVYKHHQLVPNEAVSHLFTGVKALEGGDGLSP    60
MLP2     M------------------------FKHDENITN-IIPHIYTSFKVVEG-DGLIS          29
MLP3     MAQH-HTISGLIGKLVTESEVNCDAEKYYKILKHHEDVPN-ATPYVS-DVKVTEGHGTTSG     58
MLP4     MASYDYGLSGLIGKFIIQLEINSDADNFYEIYRHCKDVPK-AVPHLFTGVKVTKGDELVSG     60
PR10-15  MA-QPQCISGLSGKLVTKSNVNCGANDFYTIFKQHVDVPK-AIPQIYKCVKVEGDGTTSG      59
PR10-14  MA-HHYSTSGLVGKLVTEMEVNCNAENYYQIFKQHEGVPK-AIPHIFTSMKVLEGHGLTSG     59
THS2     MA---PLGVSGLVGKLSTELEVDCDAEKYYNMYKHGEDVQK-AVPHLCVDVKVISGDPTSSG     80

2a          2       2b          3

NISO     C-IKEWDCVLDGKAMSGKEETTHNDETRTLRERELEGDLMKDYKKFDSIIEVNPKPNGHGSI    137
PR10-8   C-IKEWHYILEGKAMSAMEETTHNDETRTLHHQVVEGEVMKDYKAIASIIQVNPNPNGHGSI    119
PR10-9   C-IKEWKYIIDGKALTAVEETTHGDETRTLHRVIDGDLMKDYKKFDKIIEANPKPNGHGSI     119
PR10-10  C-IKEWNYVLEGKAMTAVEETTHADETRTLTHHITEGDAMKDYKKFDVIVETNPKPNGHGSV    119
PR10-5   C-IKEWNYILEGKALIAVEETTHDDETRTLTHRITGGDITKDYKKEVKIVEVNPKPNGHGSI    119
PR10-4   C-VKEWGYLLEGKELIVKETTTYDETRTIHHSAVGGHMTKIYKKFDATLVVNPKPSGHGST    120
PR10-11  C-VKEWGYMHEGKTLTCKEKTTYNDETRTICHSISEGDLMNDYKKFDATLVVDPKDNGHGSI    120
PR10-12  S-IKEWNYIIEGKAMRAMEESTHNDETRTISHRVVEGDLLKDYKKFESINEINPKPNGNGCV    119
MLP15    C-VKEWCYILEGKPLTVKEKTTYNDETRTINHNGIEGGMMTDYKKFVATLVVKPRANGQGSI    120
MLP1     VHIKEWSYILEGKTMTAVEESTYDDETRTISHRIVEGDVMKDYKKFDEIVVAKPKPDGHGSI    121
MLP2     GCTKEWGYLSEGKARIVKEQTTFDDETRTIHHCARAGDMMNDYKKFVLTLVVNPKA--HCQ-    88
MLP3     C-VKQWNFVVAGRNEYVLEKTTYNDETRTICHSDFEGDLMKKYKKFDAILVVKPRDNGHGSN    119
MLP4     C-IKEWNYVLEGKAMTAVEETTIDDATRTLTHHVIEGDVMKDYKKFDVIIEGDGHGSK       121
PR10-15  C-IKEWGYHCEGKELIVKEKTTYDETRTICHCVVGGDIANEYKKEYAILVVNPKPCCN---     117
PR10-14  C-IKEWHYLHEGKALKFKETTTYNDEERTICHSVIGGDILNDYKNFSATLLVKVKPMGHGTT    120
THS2     C-IKEWNVNIDGKTIRSVEETTHNDETKIIRHRVFEGDMMKDFKKFDTIMVVNPKPDGNGCV    141

PR10-14  LAPPVQPAPKQHFSQPAQPASKHHHFSLHRPHLNQPAQPDSKHHLSLHRPHLNLCKTISHCP
         LTGRVLGVQDSSPPAPTYVAPPVPTYVAPPMH                                  214

4
NISO     ----VTWSIEYEKMNEDSPAPFAYLASFHQNVVEVDSHI------CLS--EYPYDVPDYA      185
PR10-8   ----VTWSIEYEKMNEDSPTPFAYLEFFHQNIIDMNSHLYVGSDSHLHVDEYPYDVPDYA      175
PR10-9   ----VTVSLLYEKINEDSPAPFDHLKFFHQNIEDMNSHI------CAS--EYPYDVPDYA      167
PR10-10  ----VTYSIVYEKINEDSPAPFDYLKFFHQNIVDMSAHI------CSSA-YPYDVPDYA      167
PR10-5   ----VTVSLVYEKMNEGSPTPFNYLQFVHQTIVGLNSHI------CAS--EYPYDVPDYA     167
PR10-4   ----VSWTIDYEKINEDSPVPIPYLAFFHKLIEDLNSHL------CA---EYPYDVPDYA      167
PR10-11  ----VKYILDYEKINEDSPVPIHYLALCNQATEDLNTYL------CAS--VYPYDVPDYA      168
PR10-12  ----VTWTIAYEKINEDSPTPFAYIPFVHQAIEDTNKHL------AGS--EYPYDVPDYA      167
MLP15    ----VTWIVDYEKINEDSPVPFDYLAFFQQNIEDLNSHL------CAS--DYPYDVPDYA      168
MLP1     ----VSISIMYEKINEDSPTPFDILKTFHQNILDLSAHI------CAS--EYPYDVPDYA      169
MLP2     -GSTVKWIIDYEKINEDSPVPPAYLSLCIKITEGLNSHI------YAS--EYPYDVPDYA      139
MLP3     ----VRWTIEYEKNNEDSPVPIDYLGFFQSLIDDLNSHL------CSS---YPYDVPDYA     167
MLP4     GGSIVTVSIVMDRMNAKSPAPFDYYKFYYQNIVDMDAHI------STS---YPYDVPDYA     173
PR10-15  -GSIVSWTVDYEKINKDSPIPIPYIALFARVIEGLDSYL------CAY--AYPYDVPDYA     168
PR10-14  YGSTVMWIIDYEKINKDSPIPVPYLAFFHQIIVDLNSHF-----SASY---YPYDVPDYA     266
THS2     ----VTRSIEYEKTNENSPTPFDYLQFGHQAIEDMNKYL-----RDSE-----------      180
```

FIG. 11

SEQUENCE LISTING

<160> NUMBER OF SEQ ID NOS: 61

<210> SEQ ID NO 1
<211> LENGTH: 737
<212> TYPE: DNA
<213> ORGANISM: Papaver somniferum

<400> SEQUENCE: 1
atgtacagct cataatgtca caatatcagc tgattctttt tctatataaa ctcgttatac    60

```
caacatggac tcagtatcag ctgctctagt atttcatagt tccatatact tgtgtgcaat    120
ggctcatcat ggtgtttcag gtctagttgg gaaaattgta actgaattgg aggtgaattg    180
taatgccgac gaattttata agattttgaa gcgcgatgaa gatgttccac gggcagtttc    240
tgatcttttc cctcccgtca aaattgccaa aggagatgga cttgtttctg gttgtatcaa    300
ggaatgggac tgtgttcttg atggtaaggc gatgagcggc aaggaggaaa caacacacaa    360
cgatgaaacg aggactttgc gtcaccgtga attggaagga cttgatgaa aggattacaa     420 gaagtttgat tccataattg aagttaatcc aaaaccaaat ggacatggaa gcattgtgac    480
gtggtcaatt gagtatgaga aaatgaacga agattctccg gctccctttg cttatctagc    540
ttccttccat cagaacgttg tggaagttga ttctcacctc tgcctttctg aataagatgc    600
aagtacatga acacgacttt agtgttcgat gtacgtcagt atatgttgtt taaatgttct    660
tcttgcggta tgcctatgtc tacgtgatca agttcagtgt tcgtacacgt gagctttgtg    720
gttttgtggt tacctat                                                    737

<210> SEQ ID NO 2
<211> LENGTH: 176
<212> TYPE: PRT
<213> ORGANISM: Papaver somniferum

<400> SEQUENCE: 2

Met Asp Ser Val Ser Ala Ala Leu Val Phe His Ser Ser Ile Tyr Leu
1               5                   10                  15

Cys Ala Met Ala His His Gly Val Ser Gly Leu Val Gly Lys Ile Val
                20                  25                  30

Thr Glu Leu Glu Val Asn Cys Asn Ala Asp Glu Phe Tyr Lys Ile Leu
            35                  40                  45

Lys Arg Asp Glu Asp Val Pro Arg Ala Val Ser Asp Leu Phe Pro Pro
        50                  55                  60

Val Lys Ile Ala Lys Gly Asp Gly Leu Val Ser Gly Cys Ile Lys Glu
65                  70                  75                  80

Trp Asp Cys Val Leu Asp Gly Lys Ala Met Ser Gly Lys Glu Glu Thr
                85                  90                  95

Thr His Asn Asp Glu Thr Arg Thr Leu Arg His Arg Glu Leu Glu Gly
            100                 105                 110

Asp Leu Met Lys Asp Tyr Lys Lys Phe Asp Ser Ile Ile Glu Val Asn
        115                 120                 125

Pro Lys Pro Asn Gly His Gly Ser Ile Val Thr Trp Ser Ile Glu Tyr
    130                 135                 140

Glu Lys Met Asn Glu Asp Ser Pro Ala Pro Phe Ala Tyr Leu Ala Ser
145                 150                 155                 160

Phe His Gln Asn Val Val Glu Val Asp Ser His Leu Cys Leu Ser Glu
                165                 170                 175

<210> SEQ ID NO 3
<211> LENGTH: 966
<212> TYPE: DNA
<213> ORGANISM: Papaver somniferum

<400> SEQUENCE: 3
atggagagta atggtgtacc tatgatcact ctcagttccg gcattcggat gcctgcttta     60
ggtatgggaa cagctgaaac aatggtaaaa ggaacagaaa gagagaaatt ggcgttttg    120 aaagcgatag aggtcggtta cagacacttc gatacagctg ctgcatacca aagtgaagag    180
```

```
tgtcttggtg aagctatagc tgaagcactt caacttggtc taataaaatc tcgagatgaa      240
ctcttcatca cttccaagct ctggtgcgct gatgctcacg ctgatcttgt cctccctgct      300
cttcagaatt ctctgaggaa tcttaaattg gactatcttg atctatattt gatacaccat      360
ccggtaagct tgaagccagg gaagtttgtt aacgaaatac caaaggatca tatccttcca      420
atggactaca atctgtatg gcagccatg gaagagtgtc agacccttgg cttcactagg       480
gcaatcgggg tctgtaattt ctcatgcaaa aagcttcaag agttgatggc agcagccaag      540
atccctccag ttgtgaatca agtggagatg agcccgactt acatcaaaa aaatctgagg       600 gaatattgca aggccaataa tatcatgatc actgcacact cggttttggg agccatatgt      660
gctccatggg gcagcaatgc agttatggat tctaaggtgc ttcaccagat tgctgtggca      720
agaggaaaat ctgttgccca ggttagtatg agatgggttt accagcaagg cgcgagtcta      780
gtggtgaaaa gtttcaatga agggaggatg aaggaaaacc ttaagatatt tgattgggaa      840
ctaacggcag agaatatgga aaagatcagt gagattccgc aatctagaac aagctctgct      900
gatttcttgt tataccgac tggacctttc aaaactgaag aagagttctg ggatgagaag       960
gattga                                                                 966
```

<210> SEQ ID NO 4
<211> LENGTH: 321
<212> TYPE: PRT
<213> ORGANISM: Papaver somniferum

<400> SEQUENCE: 4

```
Met Glu Ser Asn Gly Val Pro Met Ile Thr Leu Ser Ser Gly Ile Arg
1               5                   10                  15

Met Pro Ala Leu Gly Met Gly Thr Ala Glu Thr Met Val Lys Gly Thr
            20                  25                  30

Glu Arg Glu Lys Leu Ala Phe Leu Lys Ala Ile Glu Val Gly Tyr Arg
        35                  40                  45

His Phe Asp Thr Ala Ala Ala Tyr Gln Ser Glu Glu Cys Leu Gly Glu
    50                  55                  60

Ala Ile Ala Glu Ala Leu Gln Leu Gly Leu Ile Lys Ser Arg Asp Glu
65                  70                  75                  80

Leu Phe Ile Thr Ser Lys Leu Trp Cys Ala Asp Ala His Ala Asp Leu
                85                  90                  95

Val Leu Pro Ala Leu Gln Asn Ser Leu Arg Asn Leu Lys Leu Asp Tyr
            100                 105                 110

Leu Asp Leu Tyr Leu Ile His His Pro Val Ser Leu Lys Pro Gly Lys
        115                 120                 125

Phe Val Asn Glu Ile Pro Lys Asp His Ile Leu Pro Met Asp Tyr Lys
    130                 135                 140

Ser Val Trp Ala Ala Met Glu Glu Cys Gln Thr Leu Gly Phe Thr Arg
145                 150                 155                 160

Ala Ile Gly Val Cys Asn Phe Ser Cys Lys Lys Leu Gln Glu Leu Met
                165                 170                 175

Ala Ala Ala Lys Ile Pro Pro Val Val Asn Gln Val Glu Met Ser Pro
            180                 185                 190

Thr Leu His Gln Lys Asn Leu Arg Glu Tyr Cys Lys Ala Asn Asn Ile
        195                 200                 205

Met Ile Thr Ala His Ser Val Leu Gly Ala Ile Cys Ala Pro Trp Gly
    210                 215                 220
```

```
Ser Asn Ala Val Met Asp Ser Lys Val Leu His Gln Ile Ala Val Ala
225                 230                 235                 240

Arg Gly Lys Ser Val Ala Gln Val Ser Met Arg Trp Val Tyr Gln Gln
            245                 250                 255

Gly Ala Ser Leu Val Val Lys Ser Phe Asn Glu Gly Arg Met Lys Glu
            260                 265                 270

Asn Leu Lys Ile Phe Asp Trp Glu Leu Thr Ala Glu Asn Met Glu Lys
            275                 280                 285

Ile Ser Glu Ile Pro Gln Ser Arg Thr Ser Ser Ala Asp Phe Leu Leu
290                 295                 300

Ser Pro Thr Gly Pro Phe Lys Thr Glu Glu Glu Phe Trp Asp Glu Lys
305                 310                 315                 320

Asp
```

```
<210> SEQ ID NO 5
<211> LENGTH: 1095
<212> TYPE: DNA
<213> ORGANISM: Papaver somniferum

<400> SEQUENCE: 5
atggagaaag caaaacttat gaagctaggt aatggtatgg aaataccaag tgttcaagaa      60
ttggctaaac tcacgcttgc cgaaattcca tctcgatacg tatgcgccaa tgaaaacctt     120
ttgttgccta tgggtgcatc tgtcataaat gatcatgaaa ccattcctgt catcgatata     180
gaaaatttat tatctccaga accaataatc ggaaagttag aattagatag cttcattttt     240
gcttgcaaag aatggggttt ttttcaggta gtgaaccatg gagtcgacgc ttcattggtg     300
gatagtgtaa atcagaaatt tcaaggtttc tttaaccttt ctatggatga aaaactaaa     360
tatgaacagg aagatggaga gtggaaggat tttggacaag ctttattga atcagaggac     420
caaacacttg attgggcaga tatatttatg atgttcactc ttccactcca tttaaggaag     480
cctcacttat tttcaaaact cccagtgcct ctcaggagag caatcgaatc ctactcatca     540
gaaatgaaaa agttatccat ggttctcttt aataagatgg aaaaagctct acaagtacaa     600
gcagccgaga ttaagggtat gtcagaggtg tttatagatg ggacacaagc aatgaggatg     660
aactattatc ccccttgtcc tcaaccaaat ctcgccatcg gtcttacgtc gcactcggat     720
tttggcggtt tgacaatcct ccttcaaatc aacgaagtgg aaggattaca gataaaaga     780
gaggggacat ggatttcagt caaacctcta cctaatgcgt tcgtagtgaa tgttggagat     840
atttggaga taatgactaa tggaatttac catagtgtcg atcaccgggc agtagtaaac     900
tcaacaaatg agaggctctc aatcgcaaca tttcatgacc ctagtctaga gtcggtaata     960
ggcccaatat caagcttgat tactccagag acacctgctt tgtttaaaag tggatctaca    1020
tatggggatc ttgtggagga atgtaaaaca aggaagctcg atggaaaatc atttcttgac    1080
tccatgagga tttga                                                     1095
```

```
<210> SEQ ID NO 6
<211> LENGTH: 364
<212> TYPE: PRT
<213> ORGANISM: Papaver somniferum

<400> SEQUENCE: 6

Met Glu Lys Ala Lys Leu Met Lys Leu Gly Asn Gly Met Glu Ile Pro
1               5                   10                  15

Ser Val Gln Glu Leu Ala Lys Leu Thr Leu Ala Glu Ile Pro Ser Arg
            20                  25                  30
```

Tyr Val Cys Ala Asn Glu Asn Leu Leu Pro Met Gly Ala Ser Val
         35                  40                  45

Ile Asn Asp His Glu Thr Ile Pro Val Ile Asp Ile Glu Asn Leu Leu
 50                  55                  60

Ser Pro Glu Pro Ile Ile Gly Lys Leu Glu Leu Asp Arg Leu His Phe
 65                  70                  75                  80

Ala Cys Lys Glu Trp Gly Phe Phe Gln Val Val Asn His Gly Val Asp
                 85                  90                  95

Ala Ser Leu Val Asp Ser Val Lys Ser Glu Ile Gln Gly Phe Phe Asn
                100                 105                 110

Leu Ser Met Asp Glu Lys Thr Lys Tyr Glu Gln Glu Asp Gly Asp Val
            115                 120                 125

Glu Gly Phe Gly Gln Gly Phe Ile Glu Ser Glu Asp Gln Thr Leu Asp
130                 135                 140

Trp Ala Asp Ile Phe Met Met Phe Thr Leu Pro Leu His Leu Arg Lys
145                 150                 155                 160

Pro His Leu Phe Ser Lys Leu Pro Val Pro Leu Arg Glu Thr Ile Glu
                165                 170                 175

Ser Tyr Ser Ser Glu Met Lys Lys Leu Ser Met Val Leu Phe Asn Lys
            180                 185                 190

Met Glu Lys Ala Leu Gln Val Gln Ala Ala Glu Ile Lys Gly Met Ser
        195                 200                 205

Glu Val Phe Ile Asp Gly Thr Gln Ala Met Arg Met Asn Tyr Tyr Pro
210                 215                 220

Pro Cys Pro Gln Pro Asn Leu Ala Ile Gly Leu Thr Ser His Ser Asp
225                 230                 235                 240

Phe Gly Gly Leu Thr Ile Leu Leu Gln Ile Asn Glu Val Glu Gly Leu
                245                 250                 255

Gln Ile Lys Arg Glu Gly Thr Trp Ile Ser Val Lys Pro Leu Pro Asn
            260                 265                 270

Ala Phe Val Val Asn Val Gly Asp Ile Leu Glu Ile Met Thr Asn Gly
        275                 280                 285

Ile Tyr His Ser Val Asp His Arg Ala Val Val Asn Ser Thr Asn Glu
290                 295                 300

Arg Leu Ser Ile Ala Thr Phe His Asp Pro Ser Leu Glu Ser Val Ile
305                 310                 315                 320

Gly Pro Ile Ser Ser Leu Ile Thr Pro Glu Thr Pro Ala Leu Phe Lys
                325                 330                 335

Ser Gly Ser Thr Tyr Gly Asp Leu Val Glu Glu Cys Lys Thr Arg Lys
            340                 345                 350

Leu Asp Gly Lys Ser Phe Leu Asp Ser Met Arg Ile
        355                 360

<210> SEQ ID NO 7
<211> LENGTH: 1083
<212> TYPE: DNA
<213> ORGANISM: Papaver somniferum

<400> SEQUENCE: 7
atggagacac caatacttat caagctaggc aatggtttgt caataccaag tgttcaggaa     60
ttggctaaac tcacgcttgc agaaattcca tctcgataca catgcaccgg tgaaagcccg    120
ttgaataata ttggtgcgtc tgtaacagat gatgaaacag ttcctgtcat cgatttgcaa    180
aatttactat ctccagaacc cgtagttgga aagttagaat tggataagct tcattctgct    240

```
tgcaaagaat ggggtttctt tcagctggtt aaccatggag tcgacgcttt actgatggac    300
aatataaaat cagaaattaa aggtttcttt aaccttccaa tgaatgagaa actaaatac    360 ggacagcaag atggagattt tgaaggattt ggacaaccct atattgaatc ggaggaccaa    420
agacttgatt ggactgaagt gtttagcatg ttaagtcttc ctctccattt aaggaagcct    480
catttgtttc cagaactccc tctgcctttc agggagacac tggaatccta cctatcaaaa    540
atgaaaaaac tatcaacggt tgtctttgag atgttggaaa aatctctaca attagttgag    600
attaaaggta tgacagactt atttgaagat gggttgcaaa caatgaggat gaactattat    660
cctccttgtc ctcgaccaga gcttgtactt ggtcttacgt cacactcgga ttttagcggt    720
ttgacaattc tccttcaact taatgaagtt gaaggattac aaataagaaa agaagagagg    780
tggatttcaa tcaaacctct acctgatgcg ttcatagtga atgttggaga cattttggag    840
ataatgacta atgggattta ccgtagcgtc gagcaccggg cagtagtaaa ctcaacaaag    900
gagaggctct caatcgcgac atttcatgac tctaaactag agtcagaaat aggcccaatt    960
tcgagcttgg tcacaccaga gacacctgct tgttcaaaa gaggtaggta tgaggatatt   1020
ttgaaggaaa atctttcaag gaagcttgat ggaaaatcat ttctcgacta catgaggatg   1080
tga                                                                1083
```

<210> SEQ ID NO 8
<211> LENGTH: 360
<212> TYPE: PRT
<213> ORGANISM: Papaver somniferum

<400> SEQUENCE: 8

```
Met Glu Thr Pro Ile Leu Ile Lys Leu Gly Asn Gly Leu Ser Ile Pro
1               5                   10                  15

Ser Val Gln Glu Leu Ala Lys Leu Thr Leu Ala Glu Ile Pro Ser Arg
            20                  25                  30

Tyr Thr Cys Thr Gly Glu Ser Pro Leu Asn Asn Ile Gly Ala Ser Val
        35                  40                  45

Thr Asp Asp Glu Thr Val Pro Val Ile Asp Leu Gln Asn Leu Leu Ser
    50                  55                  60

Pro Glu Pro Val Val Gly Lys Leu Glu Leu Asp Lys Leu His Ser Ala
65                  70                  75                  80

Cys Lys Glu Trp Gly Phe Phe Gln Leu Val Asn His Gly Val Asp Ala
                85                  90                  95

Leu Leu Met Asp Asn Ile Lys Ser Glu Ile Lys Gly Phe Phe Asn Leu
            100                 105                 110

Pro Met Asn Glu Lys Thr Lys Tyr Gly Gln Gln Asp Gly Asp Phe Glu
        115                 120                 125

Gly Phe Gly Gln Pro Tyr Ile Glu Ser Glu Asp Gln Arg Leu Asp Trp
    130                 135                 140

Thr Glu Val Phe Ser Met Leu Ser Leu Pro Leu His Leu Arg Lys Pro
145                 150                 155                 160

His Leu Phe Pro Glu Leu Pro Leu Pro Phe Arg Glu Thr Leu Glu Ser
                165                 170                 175

Tyr Leu Ser Lys Met Lys Lys Leu Ser Thr Val Val Phe Glu Met Leu
            180                 185                 190

Glu Lys Ser Leu Gln Leu Val Glu Ile Lys Gly Met Thr Asp Leu Phe
        195                 200                 205

Glu Asp Gly Leu Gln Thr Met Arg Met Asn Tyr Tyr Pro Pro Cys Pro
```

```
        210                 215                 220
Arg Pro Glu Leu Val Leu Gly Leu Thr Ser His Ser Asp Phe Ser Gly
225                 230                 235                 240

Leu Thr Ile Leu Leu Gln Leu Asn Glu Val Glu Gly Leu Gln Ile Arg
                245                 250                 255

Lys Glu Glu Arg Trp Ile Ser Ile Lys Pro Leu Pro Asp Ala Phe Ile
                260                 265                 270

Val Asn Val Gly Asp Ile Leu Glu Ile Met Thr Asn Gly Ile Tyr Arg
                275                 280                 285

Ser Val Glu His Arg Ala Val Val Asn Ser Thr Lys Glu Arg Leu Ser
            290                 295                 300

Ile Ala Thr Phe His Asp Ser Lys Leu Glu Ser Glu Ile Gly Pro Ile
305                 310                 315                 320

Ser Ser Leu Val Thr Pro Glu Thr Pro Ala Leu Phe Lys Arg Gly Arg
                325                 330                 335

Tyr Glu Asp Ile Leu Lys Glu Asn Leu Ser Arg Lys Leu Asp Gly Lys
                340                 345                 350

Ser Phe Leu Asp Tyr Met Arg Met
                355                 360

<210> SEQ ID NO 9
<211> LENGTH: 531
<212> TYPE: DNA
<213> ORGANISM: Papaver somniferum

<400> SEQUENCE: 9
atggactcag tatcagctgc tctagtattt catagttcca tatacttgtg tgcaatggct      60
catcatggtg tttcaggtct agttgggaaa attgtaactg aattggaggt gaattgtaat     120
gccgacgaat tttataagat tttgaagcgc gatgaagatg ttccacgggc agtttctgat     180
cttttccctc ccgtcaaaat tgccaaagga gatggacttg tttctggttg tatcaaggaa     240
tgggactgtg ttcttgatgg taaggcgatg agcggcaagg aggaaacaac acacaacgat     300
gaaacgagga ctttgcgtca ccgtgaattg aaggagact tgatgaagga ttacaagaag     360
tttgattcca taattgaagt taatccaaaa ccaaatggac atggaagcat tgtgacgtgg     420
tcaattgagt atgagaaaat gaacgaagat tctccggctc cctttgctta tctagcttcc     480
ttccatcaga acgttgtgga agttgattct cacctctgcc tttctgaata a              531

<210> SEQ ID NO 10
<211> LENGTH: 501
<212> TYPE: DNA
<213> ORGANISM: Papaver somniferum

<400> SEQUENCE: 10
atggctcatc acggtgtttc aggtctagtt gggaaacttg taactcaatt agaggtcaat      60
tgtgatgctg acgaatttta taaaatttgg aagcaccatg aagaagttcc aaaggcagtt     120
tctcattttt tccctgccgt caaagttgtc aaaggagatg gacttgtttc tggttgtatc     180
aaggaatggc actatatcct cgagggtaag gcgatgagcg caatggagga aacgacacac     240
aatgatgaaa caaggacttt acatcaccag gtagttgaag agaagtgat gaaggattac     300 aaggcgattg cttccataat tcaagttaat ccaaatccaa atggacatgg aagcattgtg     360
acgtggtcaa ttgagtatga gaaatgaac gaagattctc caactccctt gcttatcttt     420
gaattcttcc atcagaacat aatcgatatg aattctcacc tctacgtagg ctctgattct     480
```
cacctccacg ttgatgaata a                                                  501

<210> SEQ ID NO 11
<211> LENGTH: 166
<212> TYPE: PRT
<213> ORGANISM: Papaver somniferum

<400> SEQUENCE: 11

Met Ala His His Gly Val Ser Gly Leu Val Gly Lys Leu Val Thr Gln
1               5                   10                  15

Leu Glu Val Asn Cys Asp Ala Asp Glu Phe Tyr Lys Ile Trp Lys His
            20                  25                  30

His Glu Val Pro Lys Ala Val Ser His Phe Pro Ala Val Lys
        35                  40                  45

Val Val Lys Gly Asp Gly Leu Val Ser Gly Cys Ile Lys Glu Trp His
    50                  55                  60

Tyr Ile Leu Glu Gly Lys Ala Met Ser Ala Met Glu Glu Thr Thr His
65                  70                  75                  80

Asn Asp Glu Thr Arg Thr Leu His His Gln Val Val Glu Gly Glu Val
                85                  90                  95

Met Lys Asp Tyr Lys Ala Ile Ala Ser Ile Ile Gln Val Asn Pro Asn
            100                 105                 110

Pro Asn Gly His Gly Ser Ile Val Thr Trp Ser Ile Glu Tyr Glu Lys
        115                 120                 125

Met Asn Glu Asp Ser Pro Thr Pro Phe Ala Tyr Leu Glu Phe Phe His
130                 135                 140

Gln Asn Ile Ile Asp Met Asn Ser His Leu Tyr Val Gly Ser Asp Ser
145                 150                 155                 160

His Leu His Val Asp Glu
            165

<210> SEQ ID NO 12
<211> LENGTH: 477
<212> TYPE: DNA
<213> ORGANISM: Papaver somniferum

<400> SEQUENCE: 12
atggcgcacc acggtgtgag cggcctggtt ggcaagatcg tgaccgagct ggaagttaac      60
tgcaacgcgg atgagttcta taagattctg aaacgtgacg aagatgttcc gcgtgcggtg     120
agcgacctgt ttccgccggt taagatcgcg aaaggtgatg gcctggtgag cggctgcatt     180
aaagagtggg actgcgtgct ggatggcaag gcgatgagcg gtaaagagga aaccacccac     240
aacgacgaaa cccgtacccT gcgtcaccgt gagctggaag gtgacctgat gaaggattac     300
aagaaattcg atagcatcat tgaggttaac ccgaaaccga acgtcacgg cagcatcgtg     360 acctggagca ttgagtacga aaagatgaac gaagacagcc cggcgccgtt cgcgtatctg     420
gcgagctttc accagaacgt ggttgaggtt gatagccacc tgtgcctgag cgaataa        477

<210> SEQ ID NO 13
<211> LENGTH: 1567
<212> TYPE: DNA
<213> ORGANISM: Papaver somniferum

<400> SEQUENCE: 13
cgaggaaggc ctccacgaag gcgatcaggt cgaggttgga atcccgggag acggtgggga      60
agcccaccag gcggtcgagc atctcggcgg cggtcatggc gcgctccttg gtcacgtttc     120

```
gggaaatcct atcacgcccg cggggcaggc cggcggcctg ggcgtcatag ccccagacta    180
tccggtcgat gccgtcactc tttttgacag cagtcattaa caggcttaag atgtcgggcg    240
acgacggata cccgtccatt cactcttcat ctggaggcgt attgatgccg gatacatcct    300
tctccaaccc cgggctcttc accccgctgc agctgggcag cctcagcctg cccaaccgcg    360
tgatcatggc gccgctgacc cgctcgcgca cgccggacag cgttcccggc aggttgcagc    420
agatctacta tggccagcgc gccagcgccg ggctgatcat cagcgaggcc accaatatct    480
cgcccaccgc ccgcggctac gtctacacgc cggggatctg gaccgacgcg caggaagccg    540
gctggaaggg cgtcgtcgag gcggtgcatg ccaagggcgg gcgcatcgcc ctgcagctgt    600
ggcacgtcgg ccgtgtctcc cacgagctgg tgcagcccga cggccagcag cccgtggcac    660
cgagcgccct caaggccgag ggggcggaat gcttcgtcga gttcgaggac ggcacggcgg    720
ggctgcaccc caccagcacg ccgcgggcgc ttgagaccga cgagatcccc ggcatcgtcg    780
aggactaccg ccaggctgcg cagcgcgcca agcgtgccgg cttcgacatg gtcgaggtcc    840
acgccgccaa cgcctgcctg cccaaccagt tcctcgccac cggcaccaac cggcgcaccg    900
accagtacgg cggctccatc gagaaccggg cgcgcttccc gctggaggtg gtcgacgccg    960
tggccgaggt gttcgggccc gagcgggtcg gcatccgcct gacccccttc ctcgagctct   1020
tcggcctcac cgacgacgag cccgaggcga tggccttcta cctggccggc gagctcgacc   1080
gccgcggcct ggcctacctc cacttcaacg agcccgactg gatcggtggc gatatcacct   1140
accccgaagg cttccgggag cagatgcgcc agcgcttcaa gggtgggctg atctactgcg   1200
gcaactacga tgccgggcgc gcccaggccc gcctggatga caacaccgcc gacgccgtgg   1260
ccttcggccg ccccttcatc gccaaccccg atctgcccga gcgcttccgc ctgggggccg   1320
ccctcaacga gcccgacccc agcaccttct acggcggcgc cgaggtcggc tacaccgact   1380
accccttcct cgacaacggc cacgaccggc tcggctgagt cagcgtccgc ccctggaagc   1440
atcagcaagc ccgccagcg tgccgggctt gtggcgtgat ggggagggtg gtgcggggca   1500
tcgtcggtga ttggcgcaca tcaacaccgc ggcgtcagat ccacagaacg cattccgagg   1560
gaccgcc                                                             1567

<210> SEQ ID NO 14
<211> LENGTH: 64
<212> TYPE: DNA
<213> ORGANISM: Papaver somniferum

<400> SEQUENCE: 14
ttgaagcgcg atgaagatgt tccacgggca gtttctgatc ttttccctcc cgtcaaaatt    60
gcca                                                                 64

<210> SEQ ID NO 15
<211> LENGTH: 90
<212> TYPE: DNA
<213> ORGANISM: Papaver somniferum

<400> SEQUENCE: 15
tgggactgtg ttcttgatgg taaggcgatg agcggcaagg aggaaacaac acacaacgat    60
gaaacgagga ctttgcgtca ccgtgaattg                                     90

<210> SEQ ID NO 16
<211> LENGTH: 56
<212> TYPE: DNA
<213> ORGANISM: Papaver somniferum
```

<400> SEQUENCE: 16
gacttgatga aggattacaa gaagtttgat tccataattg aagttaatcc aaaacc                    56

<210> SEQ ID NO 17
<211> LENGTH: 75
<212> TYPE: DNA
<213> ORGANISM: Papaver somniferum

<400> SEQUENCE: 17 gctcccttg cttatctagc ttccttccat cagaacgttg tggaagttga ttctcacctc                 60
tgcctttctg aataa                                                                75

<210> SEQ ID NO 18
<211> LENGTH: 21
<212> TYPE: PRT
<213> ORGANISM: Papaver somniferum

<400> SEQUENCE: 18

Leu Lys Arg Asp Glu Asp Val Pro Arg Ala Val Ser Asp Leu Phe Pro
1               5                   10                  15

Pro Val Lys Ile Ala
            20

<210> SEQ ID NO 19
<211> LENGTH: 29
<212> TYPE: PRT
<213> ORGANISM: Papaver somniferum

<400> SEQUENCE: 19

Asp Cys Val Leu Asp Gly Lys Ala Met Ser Gly Lys Glu Glu Thr Thr
1               5                   10                  15

His Asn Asp Glu Thr Arg Thr Leu Arg His Arg Glu Leu
            20                  25

<210> SEQ ID NO 20
<211> LENGTH: 18
<212> TYPE: PRT
<213> ORGANISM: Papaver somniferum

<400> SEQUENCE: 20

Asp Leu Met Lys Asp Tyr Lys Lys Phe Asp Ser Ile Ile Glu Val Asn
1               5                   10                  15

Pro Lys

<210> SEQ ID NO 21
<211> LENGTH: 24
<212> TYPE: PRT
<213> ORGANISM: Papaver somniferum

<400> SEQUENCE: 21

Ala Pro Phe Ala Tyr Leu Ala Ser Phe His Gln Asn Val Val Glu Val
1               5                   10                  15

Asp Ser His Leu Cys Leu Ser Glu
            20

<210> SEQ ID NO 22
<211> LENGTH: 377
<212> TYPE: PRT
<213> ORGANISM: Papaver somniferum

<400> SEQUENCE: 22

-continued

```
Met Pro Asp Thr Ser Phe Ser Asn Pro Gly Leu Phe Thr Pro Leu Gln
1               5                   10                  15

Leu Gly Ser Leu Ser Leu Pro Asn Arg Val Ile Met Ala Pro Leu Thr
            20                  25                  30

Arg Ser Arg Thr Pro Asp Ser Val Pro Gly Arg Leu Gln Gln Ile Tyr
        35                  40                  45

Tyr Gly Gln Arg Ala Ser Ala Gly Leu Ile Ile Ser Glu Ala Thr Asn
    50                  55                  60

Ile Ser Pro Thr Ala Arg Gly Tyr Val Tyr Thr Pro Gly Ile Trp Thr
65                  70                  75                  80

Asp Ala Gln Glu Ala Gly Trp Lys Gly Val Val Glu Ala Val His Ala
                85                  90                  95

Lys Gly Gly Arg Ile Ala Leu Gln Leu Trp His Val Gly Arg Val Ser
            100                 105                 110

His Glu Leu Val Gln Pro Asp Gly Gln Gln Pro Val Ala Pro Ser Ala
        115                 120                 125

Leu Lys Ala Glu Gly Ala Glu Cys Phe Val Glu Phe Glu Asp Gly Thr
    130                 135                 140

Ala Gly Leu His Pro Thr Ser Thr Pro Arg Ala Leu Glu Thr Asp Glu
145                 150                 155                 160

Ile Pro Gly Ile Val Glu Asp Tyr Arg Gln Ala Ala Gln Arg Ala Lys
                165                 170                 175

Arg Ala Gly Phe Asp Met Val Glu Val His Ala Ala Asn Ala Cys Leu
            180                 185                 190

Pro Asn Gln Phe Leu Ala Thr Gly Thr Asn Arg Arg Thr Asp Gln Tyr
        195                 200                 205

Gly Gly Ser Ile Glu Asn Arg Ala Arg Phe Pro Leu Glu Val Val Asp
    210                 215                 220

Ala Val Ala Glu Val Phe Gly Pro Glu Arg Val Gly Ile Arg Leu Thr
225                 230                 235                 240

Pro Phe Leu Glu Leu Phe Gly Leu Thr Asp Asp Pro Glu Ala Met
                245                 250                 255

Ala Phe Tyr Leu Ala Gly Glu Leu Asp Arg Arg Gly Leu Ala Tyr Leu
            260                 265                 270

His Phe Asn Glu Pro Asp Trp Ile Gly Gly Asp Ile Thr Tyr Pro Glu
        275                 280                 285

Gly Phe Arg Glu Gln Met Arg Gln Phe Lys Gly Leu Ile Tyr
    290                 295                 300

Cys Gly Asn Tyr Asp Ala Gly Arg Ala Gln Arg Leu Asp Asp Asn
305                 310                 315                 320

Thr Ala Asp Ala Val Ala Phe Gly Arg Pro Phe Ile Ala Asn Pro Asp
                325                 330                 335

Leu Pro Glu Arg Phe Arg Leu Gly Ala Ala Leu Asn Glu Pro Asp Pro
            340                 345                 350

Ser Thr Phe Tyr Gly Gly Ala Glu Val Gly Tyr Thr Asp Tyr Pro Phe
        355                 360                 365

Leu Asp Asn Gly His Asp Arg Leu Gly
    370                 375
```

<210> SEQ ID NO 23
<211> LENGTH: 750
<212> TYPE: DNA
<213> ORGANISM: Papaver somniferum

<400> SEQUENCE: 23

```
tgtttcgtca tcaaaggtcg tttgctcctt aacaatcatc ctaatacccc agctaagacaa      60
taatcagtat caactatcag aaatggctca tgctcatggt atttcaggtc tagttgggaa     120
acttattact gaatcggagg ttaactgcaa cgctgacaag ttttaccaaa tgtttaagca     180
cgatgaaaat attacaaata taattcctca tatctatact agtttcaagg ttgtcgaggg     240
agatggactt atttctggtt gtaccaagga atggggctat ctttctgagg caaagcaag      300
gattgttaag gagcaaacga cctttgatga cgaaacaagg acgatacatc attgcgcaaa     360
agcaggagac atgatgaatg attacaagaa gttcgttcta acacttgtag ttaatccaaa     420
ggctcatgga caaggaagca cagtcaagtg gattatagat tatgagaaga taaatgagga     480
ttctccagtt cctttttgctt atctatctct gtgcattaag atcactgaag gtctgaactc     540
tcacatctac gcttccgaat aggttatcaa tggatatgtc caccgatatg tttgtgtatc     600
ggcgaatatc aggactcagt atatatggtg tgtgctaatg gagtttctac tagatctcct     660
atgatcgacc taataaatgc gtacgtactt gcatgtatgt gtggtgtgtt tcatttcgtt     720
tcgttttttca tctactttct gtaatttcta                                     750
```

<210> SEQ ID NO 24
<211> LENGTH: 159
<212> TYPE: PRT
<213> ORGANISM: Papaver somniferum

<400> SEQUENCE: 24

```
Met Ala His Ala His Gly Ile Ser Gly Leu Val Gly Lys Leu Ile Thr
  1               5                  10                  15

Glu Ser Glu Val Asn Cys Asn Ala Asp Lys Phe Tyr Gln Met Phe Lys
             20                  25                  30

His Asp Glu Asn Ile Thr Asn Ile Pro His Ile Tyr Thr Ser Phe
         35                  40                  45

Lys Val Val Glu Gly Asp Gly Leu Ile Ser Gly Cys Thr Lys Glu Trp
     50                  55                  60

Gly Tyr Leu Ser Glu Gly Lys Ala Arg Ile Val Lys Glu Gln Thr Thr
 65                  70                  75                  80

Phe Asp Asp Glu Thr Arg Thr Ile His His Cys Ala Lys Ala Gly Asp
                 85                  90                  95

Met Met Asn Asp Tyr Lys Lys Phe Val Leu Thr Leu Val Val Asn Pro
            100                 105                 110

Lys Ala His Gly Gln Gly Ser Thr Val Lys Trp Ile Ile Asp Tyr Glu
        115                 120                 125

Lys Ile Asn Glu Asp Ser Pro Val Pro Phe Ala Tyr Leu Ser Leu Cys
    130                 135                 140

Ile Lys Ile Thr Glu Gly Leu Asn Ser His Ile Tyr Ala Ser Glu
145                 150                 155
```

<210> SEQ ID NO 25
<211> LENGTH: 804
<212> TYPE: DNA
<213> ORGANISM: Papaver somniferum

<400> SEQUENCE: 25

```
tgtgcgagga tacataattt ctatataaac tcattcaact agctaataat tcatcaaaat      60
tcaattgaat ttatatgtgt cattgttttt caaacttact tatatatcaa ggaaaacaat     120
caatatcaat taccaaaaat ggctcaacat cataccattt caggtcttat tgggaagctt     180
```

-continued

```
gtgaccgaat cagaagttaa ttgcgatgct gaaaaatatt acaaaataat taagcaccac    240
gaagatgtac ctaatgcaac cccttatgtt tccgatgtca agttactga aggacatggt    300 accacttcgg gttgtgtcaa gcaatggaac tttgttgttg cgggtcgaaa cgaatatgtc    360
cttgaaaaaa caacatacaa tgatgaaaca aggacaatat gtcacagtga ctttgaagga    420
gacctgatga agaaatacaa gaagtttgat gcaatccttg tagttaagcc aaaggataat    480
ggacatggta gtaatgtgag atggactatt gaatatgaga agaataacga ggattctccg    540
gttccaattg attatctagg tttcttccaa tcgttaatcg atgacttgaa ctctcatctt    600
tgctcctctt aataatttgg attgatgata cgtatcaaca ccttctacgt acagttcgat    660
cgcttatgtg ggtatgtatt tgtgtgataa taaatagtat gtggattttt cacaatatat    720
acaataatgt gcatacatgc acgtgtgatt tgtcttattt attttcatta tcatttttg    780 tcatgtttta aggcgtataa tatg                                         804

<210> SEQ ID NO 26
<211> LENGTH: 157
<212> TYPE: PRT
<213> ORGANISM: Papaver somniferum

<400> SEQUENCE: 26

Met Ala Gln His His Thr Ile Ser Gly Leu Ile Gly Lys Leu Val Thr
1               5                   10                  15

Glu Ser Glu Val Asn Cys Asp Ala Glu Lys Tyr Tyr Lys Ile Ile Lys
            20                  25                  30

His His Glu Asp Val Pro Asn Ala Thr Pro Tyr Val Ser Asp Val Lys
        35                  40                  45

Val Thr Glu Gly His Gly Thr Thr Ser Gly Cys Val Lys Gln Trp Asn
    50                  55                  60

Phe Val Val Ala Gly Arg Asn Glu Tyr Val Leu Glu Lys Thr Thr Tyr
65                  70                  75                  80

Asn Asp Glu Thr Arg Thr Ile Cys His Ser Asp Phe Glu Gly Asp Leu
                85                  90                  95

Met Lys Lys Tyr Lys Lys Phe Asp Ala Ile Leu Val Val Lys Pro Lys
            100                 105                 110

Asp Asn Gly His Gly Ser Asn Val Arg Trp Thr Ile Glu Tyr Glu Lys
        115                 120                 125

Asn Asn Glu Asp Ser Pro Val Pro Ile Asp Tyr Leu Gly Phe Phe Gln
    130                 135                 140

Ser Leu Ile Asp Asp Leu Asn Ser His Leu Cys Ser Ser
145                 150                 155

<210> SEQ ID NO 27
<211> LENGTH: 711
<212> TYPE: DNA
<213> ORGANISM: Papaver somniferum

<400> SEQUENCE: 27
cttccacaca ctcttgtgca aacttctata ctacatatct acaatcaaca actatatcaa     60
tggctagtta tgattatggt cttccggtc taattgggaa atttataatt caattggaga    120
tcaatagcga tgctgacaat ttttatgaaa tctataagca ttgcaaagat gttcctaagg    180
cagttcctca tctttcact ggtgttaaag ttaccaaagg agatgaactc gtttctggtt    240
gtatcaagga atggaactat gttcttgagg gtaaggcgat gaccgctgtg gaggaaacaa    300
```

```
caattgacga tgcaacaagg accttgacac accacgtaat tgaaggagac gtgatgaagg    360
attacaagaa gttcgatgtg attattgaag ctaatccgaa gcctagtgga caaggaacca    420
ttggaggaag cattgtgact gtgtctattg tatatgacag aatgaatgcg aagtctccag    480
ctcccttcga ttattacaaa ttctattatc agaacatagt agatatggat gctcacatct    540
ccacttctta gtaaactatc ttaatctccg tgttgggtgt gcgtatgcat gtgcatatgt    600
acgtcagtac tcgttgatca atttgtatgc gttacttcac gagatctatt gcatctctat    660
aactatgtat cattttaaat aaatggagta agttatttaa aataaaaaaa a             711
```

<210> SEQ ID NO 28
<211> LENGTH: 163
<212> TYPE: PRT
<213> ORGANISM: Papaver somniferum

<400> SEQUENCE: 28

```
Met Ala Ser Tyr Asp Tyr Gly Leu Ser Gly Leu Ile Gly Lys Phe Ile
1               5                   10                  15

Ile Gln Leu Glu Ile Asn Ser Asp Ala Asp Asn Phe Tyr Glu Ile Tyr
                20                  25                  30

Lys His Cys Lys Asp Val Pro Lys Ala Val Pro His Leu Phe Thr Gly
            35                  40                  45

Val Lys Val Thr Lys Gly Asp Glu Leu Val Ser Gly Cys Ile Lys Glu
        50                  55                  60

Trp Asn Tyr Val Leu Glu Gly Lys Ala Met Thr Ala Val Glu Glu Thr
65                  70                  75                  80

Thr Ile Asp Asp Ala Thr Arg Thr Leu Thr His His Val Ile Glu Gly
                85                  90                  95

Asp Val Met Lys Asp Tyr Lys Lys Phe Asp Val Ile Ile Glu Ala Asn
            100                 105                 110

Pro Lys Pro Ser Gly Gln Gly Thr Ile Gly Gly Ser Ile Val Thr Val
        115                 120                 125

Ser Ile Val Tyr Asp Arg Met Asn Ala Lys Ser Pro Ala Pro Phe Asp
130                 135                 140

Tyr Tyr Lys Phe Tyr Tyr Gln Asn Ile Val Asp Met Asp Ala His Ile
145                 150                 155                 160

Ser Thr Ser
```

<210> SEQ ID NO 29
<211> LENGTH: 636
<212> TYPE: DNA
<213> ORGANISM: Papaver somniferum

<400> SEQUENCE: 29

```
attgatgatg gttgatactg gttcattcac aatcatccta atattaatta gttaaggcaa     60
gaaccagtat caaccatcat caatggccca tcaacataca atttcaggtc ttgtgggaaa    120
acttattact gaatcggagg ttaactgcaa tgccgacaag tattaccaaa tatttaagca    180
ccatgaagac cttccaagcg caatccctca tatttacact agcgtcaaag ctgtcgaggg    240
acatggaact acttctggat gtgtcaagga gtggtgctat attcttgagg ggaaaccact    300
tacagttaag gagaaaacaa cgtacaatga tgaaacaaga acgataaatc ataatggaat    360
agaaggaggc atgatgactg attacaagaa gttcgttgca acacttgtag ttaagccaaa    420
agctaatggg caaggaagca tcgtgacatg gatagtggat tatgagaaga ttaatgagga    480
ttctccagtt cctttcgact atctagcttt cttccaacaa aacatcgaag acttgaactc    540
```

```
tcacctctgt gcttctgatt aaattatcaa tgggtatgtc catatgcaac gatgaacatc    600
agtgttctct gtatgataat aaagtctata tgtgga                              636
```

<210> SEQ ID NO 30
<211> LENGTH: 159
<212> TYPE: PRT
<213> ORGANISM: Papaver somniferum

<400> SEQUENCE: 30

```
Met Ala His Gln His Thr Ile Ser Gly Leu Val Gly Lys Leu Ile Thr
1               5                   10                  15

Glu Ser Glu Val Asn Cys Asn Ala Asp Lys Tyr Tyr Gln Ile Phe Lys
            20                  25                  30

His His Glu Asp Leu Pro Ser Ala Ile Pro His Ile Tyr Thr Ser Val
        35                  40                  45

Lys Ala Val Glu Gly His Gly Thr Thr Ser Gly Cys Val Lys Glu Trp
    50                  55                  60

Cys Tyr Ile Leu Glu Gly Lys Pro Leu Thr Val Lys Glu Lys Thr Thr
65                  70                  75                  80

Tyr Asn Asp Glu Thr Arg Thr Ile Asn His Asn Gly Ile Glu Gly Gly
                85                  90                  95

Met Met Thr Asp Tyr Lys Lys Phe Val Ala Thr Leu Val Val Lys Pro
            100                 105                 110

Lys Ala Asn Gly Gln Gly Ser Ile Val Thr Trp Ile Val Asp Tyr Glu
        115                 120                 125

Lys Ile Asn Glu Asp Ser Pro Val Pro Phe Asp Tyr Leu Ala Phe Phe
    130                 135                 140

Gln Gln Asn Ile Glu Asp Leu Asn Ser His Leu Cys Ala Ser Asp
145                 150                 155
```

<210> SEQ ID NO 31
<211> LENGTH: 787
<212> TYPE: DNA
<213> ORGANISM: Papaver somniferum

<400> SEQUENCE: 31

```
gctttattta tatgccggcc ctcaataacc aaagacactc gatgcatctg tgcagtacat    60
atatatacgt actgcattat taagacacac aaaccaacag cttcatttgt ctctcgagta   120
gtaacaatca atatcatcaa ttttcatcca tggctcatcc ccatcctatt tcaggtctag   180
ttgggaaact agtgactgaa ttggaggtta actgcgacgc tgacaagtat tacaaaattt   240
ttaagcacca tgaagatgtt ccaaaagcag tacctcatat gtacactagc gtcaaagttg   300
tcgagggaca tggaattact tctggttgtg tcaaggaatg gggttatctt cttgagggaa   360
aagaactgat tgtcaaggaa acaacaacat acactgatga acaaggacg atacatcata   420 gcgcagtagg aggacacatg acgaagattt caagaagtt tgatgcaacg cttgtagtca   480
atccaaagcc tagtggccat ggaagcacgg tgagttggac tattgattat gagaaaatta   540
acgaggattc tcccgttcct attccatatc tagctttctt ccataagctc atcgaggact   600
tgaactctca cctctgcgct tctgattaaa gaaattattg attattgtt ctcgatggac   660 aatttcagct gttggtttgt gtgtgttaat aatgcagtac gtatatatat gtactgcaca   720
gatgcatcga gtgcttttgg ttattgaggg ccggcatata aataaagcca ctcctactca   780
agtattt                                                             787
```

<210> SEQ ID NO 32
<211> LENGTH: 159
<212> TYPE: PRT
<213> ORGANISM: Papaver somniferum

<400> SEQUENCE: 32

Met Ala His Pro His Pro Ile Ser Gly Leu Val Gly Lys Leu Val Thr
1               5                   10                  15

Glu Leu Glu Val Asn Cys Asp Ala Asp Lys Tyr Tyr Lys Ile Phe Lys
            20                  25                  30

His His Glu Asp Val Pro Lys Ala Val Pro His Met Tyr Thr Ser Val
        35                  40                  45

Lys Val Val Glu Gly His Gly Ile Thr Ser Gly Cys Val Lys Glu Trp
    50                  55                  60

Gly Tyr Leu Leu Glu Gly Lys Glu Leu Ile Val Lys Glu Thr Thr Thr
65                  70                  75                  80

Tyr Thr Asp Glu Thr Arg Thr Ile His His Ser Ala Val Gly Gly His
                85                  90                  95

Met Thr Lys Ile Tyr Lys Lys Phe Asp Ala Thr Leu Val Val Asn Pro
            100                 105                 110

Lys Pro Ser Gly His Gly Ser Thr Val Ser Trp Thr Ile Asp Tyr Glu
        115                 120                 125

Lys Ile Asn Glu Asp Ser Pro Val Pro Ile Pro Tyr Leu Ala Phe Phe
    130                 135                 140

His Lys Leu Ile Glu Asp Leu Asn Ser His Leu Cys Ala Ser Asp
145                 150                 155

<210> SEQ ID NO 33
<211> LENGTH: 884
<212> TYPE: DNA
<213> ORGANISM: Papaver somniferum

<400> SEQUENCE: 33
tttgaccggc agtttatgat aatctcacca gcagtagata cttatgatag gtaattggcc      60
actaaacaaa tgcttgtttt tctatataaa ctagatcaac tttcattgaa atttatcatc     120
aactgctcca gcaattatag ttctctacaa acttcaatat atagggcaac aatcatcaac     180
catctatggc gcatcatggt gtttcaggtc tagttgggaa acttgtaact gaattggagg     240
tccattgcaa tgctgacgca tactataaaa tctttaagca ccaagaagat gtaccaaagg     300
caatgcctca tctttacact ggcgggaaag ttatcagtgg agatgcaacc cgttctggtt     360
gtatcaagga atggaactac attcttgagg gtaaggcgct gatcgcagtg gaggaaacaa     420
cacatgacga tgaaacaagg accttaacac accgcataac tggaggagac ttgacaaagg     480
attacaaaaa gttcgttaag atcgttgaag ttaatccaaa gcctaatgga catggaagca     540
tgtgactgt atcccttgtg tatgagaaaa tgaacgaggg ttctccaact cccttaatt     600
atctacaatt tgtccatcag accattgtag gcttgaattc tcacatctgc gcttcttagt     660
aaaatacatc cgaacttcag cgttgggttt aagtatgcac gtacgatcgt cggtacttgt     720
tgtttaatta gttgtactgt acgttattcc tacacactgc actatcatgc ctatgtatgt     780
ttgattaaat aagactatgg aactatggga tttatcatat gcgatgatcc ttttgaataa     840
atcaaataag tcatttaaaa tgtgtttttt tttttctctt ttct                      884

<210> SEQ ID NO 34
<211> LENGTH: 157

<212> TYPE: PRT
<213> ORGANISM: Papaver somniferum

<400> SEQUENCE: 34

Met Ala His His Gly Val Ser Gly Leu Val Gly Lys Leu Val Thr Glu
1               5                   10                  15

Leu Glu Val His Cys Asn Ala Asp Ala Tyr Tyr Lys Ile Phe Lys His
                20                  25                  30

Gln Glu Asp Val Pro Lys Ala Met Pro His Leu Tyr Thr Gly Gly Lys
            35                  40                  45

Val Ile Ser Gly Asp Ala Thr Arg Ser Gly Cys Ile Lys Glu Trp Asn
    50                  55                  60

Tyr Ile Leu Glu Gly Lys Ala Leu Ile Ala Val Glu Glu Thr Thr His
65                  70                  75                  80

Asp Asp Glu Thr Arg Thr Leu Thr His Arg Ile Thr Gly Gly Asp Leu
                85                  90                  95

Thr Lys Asp Tyr Lys Lys Phe Val Lys Ile Val Glu Val Asn Pro Lys
            100                 105                 110

Pro Asn Gly His Gly Ser Ile Val Thr Val Ser Leu Val Tyr Glu Lys
            115                 120                 125

Met Asn Glu Gly Ser Pro Thr Pro Phe Asn Tyr Leu Gln Phe Val His
    130                 135                 140

Gln Thr Ile Val Gly Leu Asn Ser His Ile Cys Ala Ser
145                 150                 155

<210> SEQ ID NO 35
<211> LENGTH: 709
<212> TYPE: DNA
<213> ORGANISM: Papaver somniferum

<400> SEQUENCE: 35
gcatcacaaa ttaaaccaac gagatcagcg actacactat aatatactgc aattattagg      60
aaaatgaggt acgagtttat aaacgagttt gatgcacatg catcagcaga cgatgtttgg     120
ggaggaatct atggctccat tgattaccct aaactagtgg ttcaattact ccaactgtc     180
ctcgaaaaga aggaaatctt ggaaggcgat ggtcataatg ttggtactgt tctgcatgtt     240
gtgtaccttc caggatttgt tccgcggacg tacaacgaga agattgtaac gatggatcac     300
aaaaaacgtt acaaggaagt acaaatggtt gaaggaggat acttggatat gggatttaca     360
tatgtcatgg taattcatga agtactagca aaagaatgta attcttgtat cattagatca     420
attgttaagt gtgaagtcaa ggatgaattt gctgcaaatg tttctaatat tcgcaacacc     480
tttgatggat atgtcgcctt agcccgagcc gttccggaat atattgcgaa gcagcacgca     540
acatcagcag ctaattaact tgctgccgca gttaataaat ggattttcga tggtctaaat     600
aatatggaac tggataaagt acctaggact gagattactg tttccttcct atgttattcc     660
tcttgtgatc ttctttttctc tctttctatg tttttgtgct ttatctttt              709

<210> SEQ ID NO 36
<211> LENGTH: 164
<212> TYPE: PRT
<213> ORGANISM: Papaver somniferum

<400> SEQUENCE: 36

Met Arg Tyr Glu Phe Ile Asn Glu Phe Asp Ala His Ala Ser Ala Asp
1               5                   10                  15

Asp Val Trp Gly Gly Ile Tyr Gly Ser Ile Asp Tyr Pro Lys Leu Val

|   |   | 20 |   |   |   | 25 |   |   |   | 30 |   |
|---|---|---|---|---|---|---|---|---|---|---|---|

Val Gln Leu Leu Pro Thr Val Leu Glu Lys Lys Glu Ile Leu Glu Gly
            35                  40                  45

Asp Gly His Asn Val Gly Thr Val Leu His Val Val Tyr Leu Pro Gly
        50                  55                  60

Phe Val Pro Arg Thr Tyr Asn Glu Lys Ile Val Thr Met Asp His Lys
65                  70                  75                  80

Lys Arg Tyr Lys Glu Val Gln Met Val Glu Gly Gly Tyr Leu Asp Met
                85                  90                  95

Gly Phe Thr Tyr Val Met Val Ile His Glu Val Leu Ala Lys Glu Cys
            100                 105                 110

Asn Ser Cys Ile Ile Arg Ser Ile Val Lys Cys Glu Val Lys Asp Glu
            115                 120                 125

Phe Ala Ala Asn Val Ser Asn Ile Arg Asn Thr Phe Asp Gly Tyr Val
        130                 135                 140

Ala Leu Ala Arg Ala Val Pro Glu Tyr Ile Ala Lys Gln His Ala Thr
145                 150                 155                 160

Ser Ala Ala Asn

<210> SEQ ID NO 37
<211> LENGTH: 1264
<212> TYPE: DNA
<213> ORGANISM: Papaver somniferum

<400> SEQUENCE: 37

| tagaaaattt | agggggggct | agtgacccca | ctgaccccag | tgtagattcg | ccactgatat | 60 |
|---|---|---|---|---|---|---|
| cagttgctct | aatcttccat | actgccatat | atttctgtgc | aaatttcagg | ataacaatct | 120 |
| tgaactgttg | atggctcatc | acggtgtttc | aggtctagtt | gggaaacttg | taactcaatt | 180 |
| agaggtcaat | tgtgatgctg | acgaatttta | taaaatttgg | aagcaccatg | aagaagttcc | 240 |
| aaaggcagtt | tctcattttt | tccctgccgt | caaagttgtc | aaaggagatg | gacttgtttc | 300 |
| tggttgtatc | aaggaatggc | actatatcct | cgagggtaag | gcgatgagcg | caatggagga | 360 |
| aacgacacac | aatgatgaaa | caaggacttt | acatcaccag | gtagttgaag | agaagtgat | 420 |
| gaaggattac | aaggcgattg | cttccataat | tcaagttaat | ccaaatccaa | atggacatgg | 480 |
| aagcattgtg | acgtggtcaa | ttgagtatga | gaaaatgaac | gaagattctc | caactccctt | 540 |
| tgcttatctt | gaattcttcc | atcagaacat | aatcgatatg | aattctcacc | tctacgtagg | 600 |
| ctctgattct | cacctccacg | ttgatgaata | aaatgtcatt | accgtaagta | catgaacgcg | 660 |
| gctttagtgt | ttgatgtacg | tcagtatgtg | ctgtttgaat | tgatcagttt | cctgtgttat | 720 |
| tcttacttga | atcagttgct | tatgctagtc | ttgcagtatg | cctgtgtcta | cgtgcctgtg | 780 |
| tttcataata | ataaaggcta | agagcacttg | caagttataa | ttctcttctt | tatatccctt | 840 |
| ttcctatggt | gtattctgtt | taatcaagtt | ctgttttctc | tagcacaagg | gtttccacaa | 900 |
| attatctcag | ttaccctgaa | ttattttttc | ttaattgcaa | atgtaaaagg | tactaaaagg | 960 |
| agaattacta | gtacctagta | gtcgtaaccc | aatcaattga | gccaaatttg | atgcctataa | 1020 |
| tatgcgataa | tgtagctaag | aaagcttcct | gaatcaacag | tatatatata | ttgttgcggt | 1080 |
| gtcaactcct | acttctttta | ttagagttag | tttattacct | tattattgt | tttccgtacg | 1140 |
| tacttaacat | tcagtttcct | agtttataag | atttcttcag | tgagttgctt | gcttaccaag | 1200 |
| tttattcagc | tatatatagc | tcgatcctag | cttgtaacag | gacaaattat | caatataaga | 1260 |
| agtt |   |   |   |   |   | 1264 |

<210> SEQ ID NO 38
<211> LENGTH: 166
<212> TYPE: PRT
<213> ORGANISM: Papaver somniferum

<400> SEQUENCE: 38

```
Met Ala His His Gly Val Ser Gly Leu Val Gly Lys Leu Val Thr Gln
1               5                   10                  15

Leu Glu Val Asn Cys Asp Ala Asp Glu Phe Tyr Lys Ile Trp Lys His
            20                  25                  30

His Glu Glu Val Pro Lys Ala Val Ser His Phe Phe Pro Ala Val Lys
        35                  40                  45

Val Val Lys Gly Asp Gly Leu Val Ser Gly Cys Ile Lys Glu Trp His
    50                  55                  60

Tyr Ile Leu Glu Gly Lys Ala Met Ser Ala Met Glu Glu Thr Thr His
65                  70                  75                  80

Asn Asp Glu Thr Arg Thr Leu His His Gln Val Val Glu Gly Glu Val
                85                  90                  95

Met Lys Asp Tyr Lys Ala Ile Ala Ser Ile Ile Gln Val Asn Pro Asn
            100                 105                 110

Pro Asn Gly His Gly Ser Ile Val Thr Trp Ser Ile Glu Tyr Glu Lys
        115                 120                 125

Met Asn Glu Asp Ser Pro Thr Pro Phe Ala Tyr Leu Glu Phe Phe His
    130                 135                 140

Gln Asn Ile Ile Asp Met Asn Ser His Leu Tyr Val Gly Ser Asp Ser
145                 150                 155                 160

His Leu His Val Asp Glu
                165
```

<210> SEQ ID NO 39
<211> LENGTH: 851
<212> TYPE: DNA
<213> ORGANISM: Papaver somniferum
<220> FEATURE:
<221> NAME/KEY: misc_feature
<222> LOCATION: (835)..(835)
<223> OTHER INFORMATION: n is a, c, g, or t

<400> SEQUENCE: 39

| | | | | | |
|---|---|---|---|---|---|
| actgtaacgt | gcaagtccgc | atagtcttac | ttattcaaac | atttatataa | acccatagcc | 60 |
| ctaagcatat | agaatcaata | tcaactgcta | aggtcttcca | aaattctata | tacttttca | 120 |
| gcaacaaact | gttaatggct | catcatggcg | tttctggttt | agttgggaaa | cttgtaactc | 180 |
| aattggaggt | caattgtgat | gctgataaat | tgtataaaat | ctataagcac | catgaagatg | 240 |
| ttccaaaggc | aatttctcat | cttttcaccg | gtgtaaaagt | tctcgaagga | catggacttc | 300 |
| gttctggctg | tatcaaggaa | tggaaatata | ttattgatgg | taaggcgttg | actgctgtgg | 360 |
| aggaaacaac | ccatggcgat | gaaacaagga | ctttaaaaca | tcgcgtcatt | gatggagact | 420 |
| tgatgaagga | ttacaagaag | ttcgacaaga | tcattgaagc | taatccaaag | ccaaatggac | 480 |
| atggaagcat | tgtgactgtc | tctcttttgt | atgagaagat | aaatgaggac | tctccagctc | 540 |
| cgtttgatca | tctcaaattc | ttccatcaaa | acatagaaga | tatgaattct | cacatctgcg | 600 |
| cttcagagta | aaaatatctca | tcttcattgt | tgggtgtacg | tatgcgttca | gtaagtcagt | 660 |
| gcttgagaaa | ttagttgtgt | gcgttattcc | agtcagtgtt | ttgtgtaagt | agttggaatg | 720 |
| ttggatgcgt | tattcctaca | gtgtgctata | tgcttagggc | tatgggttta | tataaatgtt | 780 |

```
tgaataaaag taaaaaaact aaaaagagac tagccaaagg cacacagggg atagnaacaa      840
ataaatttaa a                                                          851

<210> SEQ ID NO 40
<211> LENGTH: 158
<212> TYPE: PRT
<213> ORGANISM: Papaver somniferum

<400> SEQUENCE: 40

Met Ala His His Gly Val Ser Gly Leu Val Gly Lys Leu Val Thr Gln
1               5                   10                  15

Leu Glu Val Asn Cys Asp Ala Asp Lys Leu Tyr Lys Ile Tyr Lys His
            20                  25                  30

His Glu Asp Val Pro Lys Ala Ile Ser His Leu Phe Thr Gly Val Lys
        35                  40                  45

Val Leu Glu Gly His Gly Leu Arg Ser Gly Cys Ile Lys Glu Trp Lys
    50                  55                  60

Tyr Ile Ile Asp Gly Lys Ala Leu Thr Ala Val Glu Glu Thr Thr His
65                  70                  75                  80

Gly Asp Glu Thr Arg Thr Leu Lys His Arg Val Ile Asp Gly Asp Leu
                85                  90                  95

Met Lys Asp Tyr Lys Lys Phe Asp Lys Ile Ile Glu Ala Asn Pro Lys
            100                 105                 110

Pro Asn Gly His Gly Ser Ile Val Thr Val Ser Leu Leu Tyr Glu Lys
        115                 120                 125

Ile Asn Glu Asp Ser Pro Ala Pro Phe Asp His Leu Lys Phe Phe His
    130                 135                 140

Gln Asn Ile Glu Asp Met Asn Ser His Ile Cys Ala Ser Glu
145                 150                 155

<210> SEQ ID NO 41
<211> LENGTH: 828
<212> TYPE: DNA
<213> ORGANISM: Papaver somniferum

<400> SEQUENCE: 41
agtatttcat agttccatat acttgtgtgc aatggctcat catggtgttt caggtctagt      60
tgggaaactt gttactcagc tggaggtcaa ttgcgatgca gacatatttt ataaaatcgt     120
taagcaccat gaagaagttc caaacgtaat tcctcatttt ttcaccggcg ttcaagtgac     180
caaaggagat ggacttgttt ctggttgtat caaggaatgg aactatgttc ttgagggtaa     240
ggcgatgacc gctgtggagg aaacaaccca cgccgatgaa acaaggaccc taacacacca     300
cataactgaa ggagacgcga tgaaagatta caagaagttt gatgtgatcg ttgaaactaa     360
tccaaagcct aatggacatg gaagcgttgt gacatattct attgtgtatg agaaaatcaa     420
tgaggattct ccagctccct tgattatcct aaaattcttc catcagaaca tagtagacat     480
gagtgctcac atctgctctt ctgcataata taccaatgaa cttcagtgtt gttgcgtgga     540
cgtattcacg tgaaaatgaa cgtcggtgct tgctgttcaa tttgtgtgcg ttattccttc     600
actatgatga tgtctatgga tgtttggtta ataagactg tgtgtggac tatcggatct      660 attgcatctc tgctgatctt tttaaataaa acatacagta taaatatttt aattagttgc     720
gccttgttag tctgtgactc ccatatccaa aatctattat tgtgatttaa aacttgcgaa     780
ctgatcaaaa atctatattg tgccaaaaat ttaatactta ttggaaac                  828
```

<210> SEQ ID NO 42
<211> LENGTH: 158
<212> TYPE: PRT
<213> ORGANISM: Papaver somniferum

<400> SEQUENCE: 42

Met Ala His His Gly Val Ser Gly Leu Val Gly Lys Leu Val Thr Gln
1               5                   10                  15

Leu Glu Val Asn Cys Asp Ala Asp Ile Phe Tyr Lys Ile Val Lys His
            20                  25                  30

His Glu Glu Val Pro Asn Val Ile Pro His Phe Phe Thr Gly Val Gln
        35                  40                  45

Val Thr Lys Gly Asp Gly Leu Val Ser Gly Cys Ile Lys Glu Trp Asn
    50                  55                  60

Tyr Val Leu Glu Gly Lys Ala Met Thr Ala Val Glu Glu Thr Thr His
65                  70                  75                  80

Ala Asp Glu Thr Arg Thr Leu Thr His His Ile Thr Glu Gly Asp Ala
                85                  90                  95

Met Lys Asp Tyr Lys Lys Phe Asp Val Ile Val Glu Thr Asn Pro Lys
            100                 105                 110

Pro Asn Gly His Gly Ser Val Val Thr Tyr Ser Ile Val Tyr Glu Lys
        115                 120                 125

Ile Asn Glu Asp Ser Pro Ala Pro Phe Asp Tyr Leu Lys Phe Phe His
    130                 135                 140

Gln Asn Ile Val Asp Met Ser Ala His Ile Cys Ser Ser Ala
145                 150                 155

<210> SEQ ID NO 43
<211> LENGTH: 873
<212> TYPE: DNA
<213> ORGANISM: Papaver somniferum

<400> SEQUENCE: 43
ttgccctaaa tacagctcat tatccagtca ccacccttta tcattcctgt agtttctggt      60
tgtttctata taaactcgtt cagctaagac taatttttcat cgcaatcaca ctcatcctaa    120
tattcagcta aggaaaccgt aagtatcaac ttttagcaat ggctcatact cgtggtatttt   180 caggtctagt tgggaaactt gttatggaaa cggaggttaa ctgcaacgct gacaagtatt    240
accaaatata taagcaccat gaagatcttc aagcgcaat ccctcatatt gtcactagcg      300
ccaaagctgt tgagggacat ggaactactt ctggttgcgt caaggagtgg ggctatatgc    360
atgagggtaa aacacttact tgcaaggaga aaactaccta taacgatgaa acaaggacga    420
tatgtcatag catatctgaa ggagacttga tgaatgatta caagaagttc gatgcaacac    480
ttgtcgttga tccaaaggat aatggacatg gaagcattgt gaagtatatt ttagattatg    540
agaagataaa tgaggattct ccggttccta ttcattatct agctctgtgc aatcaagcca    600
ccgaagactt gaacacttac ctttgtgctt ctgtctaagt tatcaatgga tatctccgcc    660
gaataaatat gcaagtatga ataccactgt tctacttcta tcagtggtat ctaataataa    720
agtctatatg tggaatttcc actagaccta tgtctataa taaatgcttc catacttgta     780
cgtacctgtt gttttcttca tttcttttttg ttatggagta ctgttttttcg tctactatct   840 tttattttta ctgaaaatca aggcgtaata ata                                  873

<210> SEQ ID NO 44
<211> LENGTH: 159

```
<212> TYPE: PRT
<213> ORGANISM: Papaver somniferum

<400> SEQUENCE: 44

Met Ala His Thr Arg Gly Ile Ser Gly Leu Val Gly Lys Leu Val Met
1               5                   10                  15

Glu Thr Glu Val Asn Cys Asn Ala Asp Lys Tyr Gln Ile Tyr Lys
            20                  25                  30

His His Glu Asp Leu Pro Ser Ala Ile Pro His Ile Val Thr Ser Ala
        35                  40                  45

Lys Ala Val Glu Gly His Gly Thr Thr Ser Gly Cys Val Lys Glu Trp
    50                  55                  60

Gly Tyr Met His Glu Gly Lys Thr Leu Thr Cys Lys Glu Lys Thr Thr
65                  70                  75                  80

Tyr Asn Asp Glu Thr Arg Thr Ile Cys His Ser Ile Ser Glu Gly Asp
                85                  90                  95

Leu Met Asn Asp Tyr Lys Lys Phe Asp Ala Thr Leu Val Val Asp Pro
            100                 105                 110

Lys Asp Asn Gly His Gly Ser Ile Val Lys Tyr Ile Leu Asp Tyr Glu
        115                 120                 125

Lys Ile Asn Glu Asp Ser Pro Val Pro Ile His Tyr Leu Ala Leu Cys
    130                 135                 140

Asn Gln Ala Thr Glu Asp Leu Asn Thr Tyr Leu Cys Ala Ser Val
145                 150                 155

<210> SEQ ID NO 45
<211> LENGTH: 781
<212> TYPE: DNA
<213> ORGANISM: Papaver somniferum

<400> SEQUENCE: 45
gttcgatata tatacttctg ttcatacttc agggcaacaa tcgtcaactg tcaatggctc    60
gtcacggagg ttcaggtcta gtagggaaac ttgtaactga actggaggtc tactgcgatg   120
ctgacaaata ttataaaatc tggaagcacc acgaagatgt tccgaaggca atgcctcata   180
tgttcactgg tgtccaacct atcaaggag atggaatctg ttccggcagc atcaaggaat   240
ggaactatat cattgaaggt aaggcaatga gagctatgga ggaatcaaca cataacgatg   300
aaacgagaac aataagtcac cgtgttgtag aaggagacct gctgaaggat tacaagaagt   360
ttgaatcgat aaatgaaatc aatcctaagc ctaacggaaa tggatgcgtc gtgacatgga   420
ctattgcata tgagaaaatc aatgaggatt ctccaactcc ctttgcatat atacctttcg   480
tccatcaggc cattgaagac acgaacaaac atcttgctgg ttccgagtaa atggtctacg   540
ccgtctatac atgaataacc cgattctccg tcggggtac gtatgctcat gcacgtacat   600
ttattaatca gttgaagttt atgtgggtta ttgttgcagt atatgcctaa atggccattt   660
cggcctatat tgttgtcat tgttctgtca gtaactacct agtttggtgt gtactctcat   720
tagagagaaa ctaaatgtac caactatttg atgatttgaa ttttctttcc tgataaaaaa   780
a                                                                   781

<210> SEQ ID NO 46
<211> LENGTH: 158
<212> TYPE: PRT
<213> ORGANISM: Papaver somniferum

<400> SEQUENCE: 46
```

```
Met Ala Arg His Gly Gly Ser Gly Leu Val Gly Lys Leu Val Thr Glu
1               5                   10                  15

Leu Glu Val Tyr Cys Asp Ala Asp Lys Tyr Tyr Lys Ile Trp Lys His
            20                  25                  30

His Glu Asp Val Pro Lys Ala Met Pro His Met Phe Thr Gly Val Gln
        35                  40                  45

Pro Ile Lys Gly Asp Gly Ile Cys Ser Gly Ser Ile Lys Glu Trp Asn
    50                  55                  60

Tyr Ile Ile Glu Gly Lys Ala Met Arg Ala Met Glu Glu Ser Thr His
65                  70                  75                  80

Asn Asp Glu Thr Arg Thr Ile Ser His Arg Val Val Glu Gly Asp Leu
                85                  90                  95

Leu Lys Asp Tyr Lys Lys Phe Glu Ser Ile Asn Glu Ile Asn Pro Lys
            100                 105                 110

Pro Asn Gly Asn Gly Cys Val Val Thr Trp Thr Ile Ala Tyr Glu Lys
        115                 120                 125

Ile Asn Glu Asp Ser Pro Thr Pro Phe Ala Tyr Ile Pro Phe Val His
    130                 135                 140

Gln Ala Ile Glu Asp Thr Asn Lys His Leu Ala Gly Ser Glu
145                 150                 155
```

<210> SEQ ID NO 47
<211> LENGTH: 770
<212> TYPE: DNA
<213> ORGANISM: Papaver somniferum

<400> SEQUENCE: 47

```
cttcaataat ctccaatcta ttgagcaaaa atcctcaact acttgatggc tcatcatggt    60
gtttcgggtt tagtcgggaa agttgtaact gaattgcgag atgctgacga gaa          120
tactataaag tctataagca ccatcaacta gtaccaaatg aggcagtttc tcatctttc   180
actggtgtta aagctcttga aggaggagac ggcctcagtc ccgttcatat caaggaatgg    240
agctatattc ttgagggaaa gacaatgacc gccgtggaag aatcaacata tgacgatgaa   300
acaaggacca tatcgcaccg catcgttgaa ggagatgtta tgaaggatta caagaagttt   360
gatgagatcg ttgtagctaa accaaagcct gatggacatg aagcattgt atccatatct   420
ataatgtatg agaaaataaa cgaggattct ccaactccat tgacatcct gaaaactttc   480
catcagaaca ttctagacct aagtgctcac atctgtgctt ccgagtaaaa tatctctcaa   540
gtgtttgggt gttacttgtt gtcatttatg tgtgcgttat tcatgcatgg actatgcatg   600
gcttttgtaac cgcagtttat cgcttctttg atcatctttt tttctttttt tatacttctt   660
ttttaaagaa gttttggctc tatgtccgtc ccttgctatt ttaattttt gttctttgat   720
cagtaaatat ttttgcttaa aaaaaaaaca atcatgagct acgtctatgt              770
```

<210> SEQ ID NO 48
<211> LENGTH: 160
<212> TYPE: PRT
<213> ORGANISM: Papaver somniferum

<400> SEQUENCE: 48

```
Met Ala His His Gly Val Ser Gly Leu Val Gly Lys Val Val Thr Glu
1               5                   10                  15

Leu Glu Leu Asn Cys Asp Ala Asp Glu Tyr Tyr Lys Val Tyr Lys His
            20                  25                  30

His Gln Leu Val Pro Asn Glu Ala Val Ser His Leu Phe Thr Gly Val
```

```
                    35                  40                  45
Lys Ala Leu Glu Gly Gly Asp Gly Leu Ser Pro Val His Ile Lys Glu
 50                  55                  60

Trp Ser Tyr Ile Leu Glu Gly Lys Thr Met Thr Ala Val Glu Glu Ser
 65                  70                  75                  80

Thr Tyr Asp Asp Glu Thr Arg Thr Ile Ser His Arg Ile Val Glu Gly
                 85                  90                  95

Asp Val Met Lys Asp Tyr Lys Lys Phe Asp Glu Ile Val Val Ala Lys
            100                 105                 110

Pro Lys Pro Asp Gly His Gly Ser Ile Val Ser Ile Ser Ile Met Tyr
        115                 120                 125

Glu Lys Ile Asn Glu Asp Ser Pro Thr Pro Phe Asp Ile Leu Lys Thr
130                 135                 140

Phe His Gln Asn Ile Leu Asp Leu Ser Ala His Ile Cys Ala Ser Glu
145                 150                 155                 160

<210> SEQ ID NO 49
<211> LENGTH: 1671
<212> TYPE: DNA
<213> ORGANISM: Papaver somniferum

<400> SEQUENCE: 49
caacaactat cagctggtcc agctgaccac tgtttctgct gatgaacctt aaggaacaaa      60
tttcagcaga gagatacaag ctgagggtgt tatcaaatat tcgacgtagg aagcgctatc     120
aaacctgact ttcatccttg aaattagaag ttcaagtctc cgctttaaga ataattagtg     180
atccattcaa aacttcaacc gtgtctccaa atgtcgcatt gtatgtgtca ccacagtgaa     240
tttcaggtaa aattttcaaa taagactgtt gataggattc tcctaaaagg ggattcagaa     300
agtatgactg ttagatcaag aaatttccaa aatagaaagg tcaacttata atttctagtg     360
gttatatctt atcgcaatac tagtggtgga aaggtcaact tataatttct gggtggatct     420
ggttgaacga tcgttgccgc caattacagc tcactattga gtcatcagta gttcagcaca     480
atttcatcaa ttcattcctg tagttgcagg ttgtttaatt ctatataagc tcatgaaata     540
tcagtattca tctaaggcaa gaatcagtat caactatcag caatggcaca tcactattcc     600
acttccggtc tagttgggaa acttgttact gaaatggagg ttaactgcaa cgccgaaaac     660
tattaccaaa tatttaagca gcatgaaggc gttccaaaag caatacctca tatttttacg     720
agcatgaaag ttcttgaggg acatggactt acttccggtt gtatcaagga atggcactat     780
cttcatgagg gaaaagcact caaattcaag gagaccacga catataacga tgaagaaagg     840
acgatatgtc acagcgttat aggaggtgac ttgttgaatg attacaagaa cttcagtgcg     900
acacttctgg ttaaggttaa gcctatgggt catggaacta cgtacctggc tccgccagtg     960
cagccagctc ccaagcaaca ttttagccaa ccagcccagc cggcatccaa gcatcatcat    1020
tttagccttc ataggcctca tttaaaccaa ccagcacagc cagattccaa gcatcatctt    1080
agtcttcata ggcctcattt aaaccttgc aagaccattt cacactgccc actgaccggc     1140
cgtgtcttgg gtgtgcaaga ttcttcccca cctgctccta cctacgtggc tccgccagtt    1200
cctacatacg tggctccgcc catgcatgga agcactgtga tgtggattat agattatgag    1260
aagatcaata aggattctcc aatccccgtt ccttatctgg cttctcttcca tcagatcatt    1320
gtagacttga actctcactt ctccgcttct tattaaatta tggatagata tgcatgccca    1380
cggatttata tatatgtatg caacgacaat cacagtgtct tgtgtacgat atatgtgtgg    1440
```

```
aaataaaaaa ctatatataa acgtggtcat gccaaaaatc tattttcggc ctaatcaagg      1500 cttttacttat tgcatgtgta tgagtggttt gtttcataat actagggcat atgaataagt      1560
gaatgaatta tgtaagtcat ttggattgat tctttcatgt tataataaga taaaaaacaa      1620
acattcagaa taatgtcggc atcgtatggg ccgcgacagt gcatcactaa g               1671
```

<210> SEQ ID NO 50
<211> LENGTH: 257
<212> TYPE: PRT
<213> ORGANISM: Papaver somniferum

<400> SEQUENCE: 50

```
Met Ala His His Tyr Ser Thr Ser Gly Leu Val Gly Lys Leu Val Thr
 1               5                  10                  15
Glu Met Glu Val Asn Cys Asn Ala Glu Asn Tyr Tyr Gln Ile Phe Lys
             20                  25                  30
Gln His Glu Gly Val Pro Lys Ala Ile Pro His Ile Phe Thr Ser Met
         35                  40                  45
Lys Val Leu Glu Gly His Gly Leu Thr Ser Gly Cys Ile Lys Glu Trp
     50                  55                  60
His Tyr Leu His Glu Gly Lys Ala Leu Lys Phe Lys Glu Thr Thr Thr
 65                  70                  75                  80
Tyr Asn Asp Glu Glu Arg Thr Ile Cys His Ser Val Ile Gly Gly Asp
                 85                  90                  95
Leu Leu Asn Asp Tyr Lys Asn Phe Ser Ala Thr Leu Leu Val Lys Val
            100                 105                 110
Lys Pro Met Gly His Gly Thr Thr Tyr Leu Ala Pro Pro Val Gln Pro
        115                 120                 125
Ala Pro Lys Gln His Phe Ser Gln Pro Ala Gln Pro Ala Ser Lys His
    130                 135                 140
His His Phe Ser Leu His Arg Pro His Leu Asn Gln Pro Ala Gln Pro
145                 150                 155                 160
Asp Ser Lys His His Leu Ser Leu His Arg Pro His Leu Asn Leu Cys
                165                 170                 175
Lys Thr Ile Ser His Cys Pro Leu Thr Gly Arg Val Leu Gly Val Gln
            180                 185                 190
Asp Ser Ser Pro Pro Ala Pro Thr Tyr Val Ala Pro Val Pro Thr
        195                 200                 205
Tyr Val Ala Pro Pro Met His Gly Ser Thr Val Met Trp Ile Ile Asp
    210                 215                 220
Tyr Glu Lys Ile Asn Lys Asp Ser Pro Ile Pro Val Pro Tyr Leu Ala
225                 230                 235                 240
Phe Phe His Gln Ile Ile Val Asp Leu Asn Ser His Phe Ser Ala Ser
                245                 250                 255
Tyr
```

<210> SEQ ID NO 51
<211> LENGTH: 819
<212> TYPE: DNA
<213> ORGANISM: Papaver somniferum

<400> SEQUENCE: 51

```
cgatcatcca aatatttagc taagccaaca attataattc agtatcaatc actatatcac        60
tatcagcaat ggctcagcct caatgtattt caggtctatc tgggaaactt gtgactaaat       120
caaatgttaa ctgcggtgcc aacgattttt acacaatttt taagcagcat gtagatgttc       180
```

```
cgaaagcgat acctcaaatt tacaagtgcg tgaaagttgt tgagggagat ggaactactt     240
ccggttgtat caaggaatgg ggataccatt gtgagggtaa ggaactgatt gtcaaggaga     300
aaacgacata caccgatgaa acaaggacga tatgtcactg cgtagtagga ggagacatag     360
caaatgagta caagaaattt tatgcaattc ttgtggttaa tccaaagcct tgtggtaatg     420
gaagcattgt gagttggact gttgattacg agaagattaa taaggattct ccaattccta     480
ttccttatat agctctgttc gctcgggtca ttgaaggctt ggactcctac ctctgcgctt     540
atgcttaaat tatcgatggg tttgcatata tatcatggga gaatcctagg gtcctgcaga     600
tggtaataaa actataaata agcgtggact tgccaagatt ctaccttcta ccttatcatc     660
aaggcttaca tattgcatgt ctgcgtggtt tgtttcgtat taaatgaata agttaattat     720
ccaagtcgtt tggagtgttt ctactgtttt aatgaacaa gtgatttatc taagtcgttt      780
gaattgtttg tttttgttta ttaaattctc atcattaac                           819
```

<210> SEQ ID NO 52
<211> LENGTH: 159
<212> TYPE: PRT
<213> ORGANISM: Papaver somniferum

<400> SEQUENCE: 52

```
Met Ala Gln Pro Gln Cys Ile Ser Gly Leu Ser Gly Lys Leu Val Thr
1               5                   10                  15

Lys Ser Asn Val Asn Cys Gly Ala Asn Asp Phe Tyr Thr Ile Phe Lys
            20                  25                  30

Gln His Val Asp Val Pro Lys Ala Ile Pro Gln Ile Tyr Lys Cys Val
        35                  40                  45

Lys Val Val Glu Gly Asp Gly Thr Thr Ser Gly Cys Ile Lys Glu Trp
    50                  55                  60

Gly Tyr His Cys Glu Gly Lys Glu Leu Ile Val Lys Glu Lys Thr Thr
65                  70                  75                  80

Tyr Thr Asp Glu Thr Arg Thr Ile Cys His Cys Val Val Gly Gly Asp
                85                  90                  95

Ile Ala Asn Glu Tyr Lys Lys Phe Tyr Ala Ile Leu Val Val Asn Pro
            100                 105                 110

Lys Pro Cys Gly Asn Gly Ser Ile Val Ser Trp Thr Val Asp Tyr Glu
        115                 120                 125

Lys Ile Asn Lys Asp Ser Pro Ile Pro Ile Pro Tyr Ile Ala Leu Phe
    130                 135                 140

Ala Arg Val Ile Glu Gly Leu Asp Ser Tyr Leu Cys Ala Tyr Ala
145                 150                 155
```

<210> SEQ ID NO 53
<211> LENGTH: 477
<212> TYPE: DNA
<213> ORGANISM: Papaver somniferum

<400> SEQUENCE: 53

```
atggctcatc atggtgtttc aggtctagtt gggaaaattg taactgaatt ggaggtgaat     60
tgtaatgccg acgaattta taagattttg aagcgcgatg aagatgttcc acgggcagtt    120
tctgatcttt tccctcccgt caaaattgcc aaaggagatg acttgtttc tggttgtatc    180 aaggaatggg actgtgttct tgatggtaag gcgatgagcg gcaaggagga aacaacacac    240
aacgatgaaa cgaggacttt gcgtcaccgt gaattggaag gagacttgat gaaggattac    300
```

```
aagaagtttg attccataat tgaagttaat ccaaaaccaa atggacatgg aagcattgtg      360
acgtggtcaa ttgagtatga gaaaatgaac gaagattctc cggctccctt tgcttatcta      420
gcttccttcc atcagaacgt tgtggaagtt gattctcacc tctgcctttc tgaataa         477
```

<210> SEQ ID NO 54
<211> LENGTH: 158
<212> TYPE: PRT
<213> ORGANISM: Papaver somniferum
<400> SEQUENCE: 54

```
Met Ala His His Gly Val Ser Gly Leu Val Gly Lys Ile Val Thr Glu
1               5                   10                  15

Leu Glu Val Asn Cys Asn Ala Asp Glu Phe Tyr Lys Ile Leu Lys Arg
            20                  25                  30

Asp Glu Asp Val Pro Arg Ala Val Ser Asp Leu Phe Pro Pro Val Lys
        35                  40                  45

Ile Ala Lys Gly Asp Gly Leu Val Ser Gly Cys Ile Lys Glu Trp Asp
    50                  55                  60

Cys Val Leu Asp Gly Lys Ala Met Ser Gly Lys Glu Glu Thr Thr His
65                  70                  75                  80

Asn Asp Glu Thr Arg Thr Leu Arg His Arg Glu Leu Glu Gly Asp Leu
                85                  90                  95

Met Lys Asp Tyr Lys Lys Phe Asp Ser Ile Ile Glu Val Asn Pro Lys
            100                 105                 110

Pro Asn Gly His Gly Ser Ile Val Thr Trp Ser Ile Glu Tyr Glu Lys
        115                 120                 125

Met Asn Glu Asp Ser Pro Ala Pro Phe Ala Tyr Leu Ala Ser Phe His
    130                 135                 140

Gln Asn Val Val Glu Val Asp Ser His Leu Cys Leu Ser Glu
145                 150                 155
```

<210> SEQ ID NO 55
<211> LENGTH: 770
<212> TYPE: DNA
<213> ORGANISM: Papaver somniferum
<400> SEQUENCE: 55

```
cttcaataat ctccaatcta ttgagcaaaa atcctcaact acttgatggc tcatcatggt       60
gtttcgggtt tagtcgggaa agttgtaact gaattggagc tcaattgcga tgctgacgaa      120
tactataaag tctataagca ccatcaacta gtaccaaatg aggcagtttc tcatcttttc      180
actggtgtta aagctcttga aggaggagac ggcctcagtc ccgttcatat caaggaatgg      240
agctatattc ttgagggaaa gacaatgacc gccgtggaag aatcaacata tgacgatgaa      300
acaaggacca tatcgcaccg catcgttgaa ggagatgtta tgaaggatta caagaagttt      360
gatgagatcg ttgtagctaa accaaagcct gatggacatg gaagcattgt atccatatct      420
ataatgtatg agaaaataaa cgaggattct ccaactccat tgacatcct gaaaactttc       480 catcagaaca ttctagacct aagtgctcac atctgtgctt ccgagtaaaa tatctctcaa      540
gtgtttgggt gttacttgtt gtcatttatg tgtgcgttat tcatgcatgg actatgcatg      600
gctttgtaac cgcagtttat cgcttctttg atcatctttt tttctttttt tatacttctt      660
ttttaaagaa gttttggctc tatgtccgtc ccttgctatt ttaatttttt gttctttgat      720
cagtaaatat ttttgcttaa aaaaaaaaca atcatgagct acgtctatgt                 770
```

<210> SEQ ID NO 56
<211> LENGTH: 170
<212> TYPE: PRT
<213> ORGANISM: Papaver somniferum

<400> SEQUENCE: 56

Met Met Ala His His Gly Val Ser Gly Leu Val Gly Lys Val Val Thr
1               5                   10                  15

Glu Leu Glu Leu Asn Cys Asp Ala Asp Glu Tyr Tyr Lys Val Tyr Lys
            20                  25                  30

His His Gln Leu Val Pro Asn Glu Ala Val Ser His Leu Phe Thr Gly
        35                  40                  45

Val Lys Ala Leu Glu Gly Gly Asp Gly Leu Ser Pro Val His Ile Lys
    50                  55                  60

Glu Trp Ser Tyr Ile Leu Glu Gly Lys Thr Met Thr Ala Val Glu Glu
65                  70                  75                  80

Ser Thr Tyr Asp Asp Glu Thr Arg Thr Ile Ser His Arg Ile Val Glu
                85                  90                  95

Gly Asp Val Met Lys Asp Tyr Lys Lys Phe Asp Glu Ile Val Val Ala
            100                 105                 110

Lys Pro Lys Pro Asp Gly His Gly Ser Ile Val Ser Ile Ser Ile Met
        115                 120                 125

Tyr Glu Lys Ile Asn Glu Asp Ser Pro Thr Pro Phe Asp Ile Leu Lys
    130                 135                 140

Thr Phe His Gln Asn Ile Leu Asp Leu Ser Ala His Ile Cys Ala Ser
145                 150                 155                 160

Glu Tyr Pro Tyr Asp Val Pro Asp Tyr Ala
                165                 170

<210> SEQ ID NO 57
<211> LENGTH: 543
<212> TYPE: DNA
<213> ORGANISM: Papaver somniferum

<400> SEQUENCE: 57
atggattcta ttaattcttc catatacttc tgtgcatatt ttagagaact aatcatcaaa    60
ttgttgatgg ctcctcttgg tgtttcaggt ttagtcggga acttttcaac tgaattggag   120
gtcgattgcg atgctgaaaa atattataac atgtataagc acggagaaga tgtgcaaaag   180
gcagttcctc atctttgcgt tgacgtcaaa gttatcagtg agatccgac cagttcaggt    240 tgtatcaagg aatggaatgt taacattgat ggtaagacga ttcgctcagt agaggaaaca   300
acacacaatg atgaaacgaa aacgttgcgt caccgtgtat ttgaaggaga catgatgaag   360
gatttcaaga agtttgatac gataatggta gtcaatccaa agccggatgg aaatggatgt   420
gttgtgacac ggtcaattga gtatgagaaa accaacgaga attctccgac tcccttttgat  480 tatctacaat tcggccatca ggccattgaa gacatgaaca aatacttacg cgattctgaa   540
taa                                                                 543

<210> SEQ ID NO 58
<211> LENGTH: 180
<212> TYPE: PRT
<213> ORGANISM: Papaver somniferum

<400> SEQUENCE: 58

Met Asp Ser Ile Asn Ser Ser Ile Tyr Phe Cys Ala Tyr Phe Arg Glu
1               5                   10                  15

-continued

```
Leu Ile Ile Lys Leu Leu Met Ala Pro Leu Gly Val Ser Gly Leu Val
             20                  25                  30

Gly Lys Leu Ser Thr Glu Leu Glu Val Asp Cys Asp Ala Glu Lys Tyr
         35                  40                  45

Tyr Asn Met Tyr Lys His Gly Glu Asp Val Gln Lys Ala Val Pro His
     50                  55                  60

Leu Cys Val Asp Val Lys Val Ile Ser Gly Asp Pro Thr Ser Ser Gly
 65                  70                  75                  80

Cys Ile Lys Glu Trp Asn Val Asn Ile Asp Gly Lys Thr Ile Arg Ser
                 85                  90                  95

Val Glu Glu Thr Thr His Asn Asp Glu Thr Lys Thr Leu Arg His Arg
             100                 105                 110

Val Phe Glu Gly Asp Met Met Lys Asp Phe Lys Lys Phe Asp Thr Ile
             115                 120                 125

Met Val Val Asn Pro Lys Pro Asp Gly Asn Gly Cys Val Val Thr Arg
 130                 135                 140

Ser Ile Glu Tyr Glu Lys Thr Asn Glu Asn Ser Pro Thr Pro Phe Asp
145                 150                 155                 160

Tyr Leu Gln Phe Gly His Gln Ala Ile Glu Asp Met Asn Lys Tyr Leu
                 165                 170                 175

Arg Asp Ser Glu
            180

<210> SEQ ID NO 59
<211> LENGTH: 13
<212> TYPE: PRT
<213> ORGANISM: Papaver somniferum

<400> SEQUENCE: 59

Lys Gly Asp Gly Leu Val Ser Gly Cys Ile Lys Glu Trp
1               5                   10

<210> SEQ ID NO 60
<211> LENGTH: 2
<212> TYPE: PRT
<213> ORGANISM: Papaver somniferum

<400> SEQUENCE: 60

Glu Gly
1

<210> SEQ ID NO 61
<211> LENGTH: 22
<212> TYPE: PRT
<213> ORGANISM: Papaver somniferum

<400> SEQUENCE: 61

Pro Asn Gly His Gly Ser Ile Val Thr Trp Ser Ile Glu Tyr Glu Lys
1               5                   10                  15

Met Asn Glu Asp Ser Pro
            20
```

NEOPINONE ISOMERASE AND METHODS OF USING

RELATED APPLICATION

This is a national phase entry of PCT/CA2019/109170 filed on Nov. 29, 2018 which claims the benefit under 35 USC § 119(e) from U.S. Provisional Patent Application No. 62/594,854, filed on Dec. 5, 2017, and from U.S. Provisional Patent Application No. 62/686,337, filed on Jun. 18, 2017, all of which are incorporated by reference herein in their entirety.

INCORPORATION OF SEQUENCE LISTING

A computer readable form of the Sequence Listing "21806-P54885US02_SequenceListing.txt" (77,824 bytes), submitted via EFS-WEB and created on Jun. 5, 2020, is herein incorporated by reference.

FIELD OF THE DISCLOSURE

The methods and systems disclosed herein relate to a class of chemical compounds known as alkaloids and methods of making alkaloids. In particular, the methods and systems disclosed herein relate to alkaloid morphinan compounds.

BACKGROUND OF THE DISCLOSURE

The following paragraphs are provided by way of background to the present disclosure. Except where expressly stated, they are not however an admission that anything discussed therein is prior art or part of the knowledge of persons skilled in the art.

Alkaloids are a class of nitrogen containing organic chemical compounds that are naturally produced by opium poppy (*Papaver somniferum*), and a range of other plant species belonging to the Papaveraceae family of plants, as well as other plant families including, for example the Lauraceae, Annonaceae, Euphorbiaceae and the Moraceae. The interest of the art in alkaloid compounds is well established and can be explained by the pharmacological properties of these compounds, as well as their utility as feedstock materials in the manufacture of pharmaceutical compounds.

The manufacture of a class of compounds known as alkaloid morphinan compounds, for example, codeine and morphine, can involve the conversion of precursor alkaloid compounds into one or more intermediary alkaloid compounds to yield the desired morphinan alkaloid compound. In biosynthetic production systems, enzymes can catalyze the conversion reaction of precursor compounds into intermediate compounds, or into a desired product. However in many biosynthetic production systems, alkaloid compounds are not efficiently converted into the desired products, for example, due to substrate inhibition, or they can be converted into products other than the desired alkaloids products, each of which results into low alkaloid product yields.

Thus, for example, in a biosynthetic production system in which it is desired that morphine or codeine is produced, wherein the system involves the alkaloid morphinan compounds neopinone or neomorphinone as a precursor compound, the reaction can be inefficient. In particular, it has been observed that substantial quantities of neopine and neomorphine can accumulate in such systems, at the expense of morphine and codeine (see: Nature Chemical Biology, 2014, 10: 837). The accumulation of neopine and neomorphine is believed to occur as the precursor compounds neopinone and neomorphine are converted to neopine and neomorphine, respectively, rather than to the desired intermediate reaction compounds, namely codeinone and morphinone.

It is noted that in biosynthetic systems for the production of morphine or codeine, the undesirable conversion of neopinone and neomorphine to neopine and neomorphine, respectively, is believed by the prior art to be catalyzed by codeinone reductase, while the desired reaction from neopinone and neomorphine to codeinone and morphinone, respectively, is believed by the prior art to the prior art to proceed spontaneously (see: Tetrahedron Letters, 1993, 34: 5703).

There exists therefore a need in the art for improved processes to produce morphinan alkaloid compounds. In particular, there exists a need in the art for production systems in which the alkaloid compounds neopinone or neomorphinone are efficiently converted to codeinone and morphinone, respectively.

SUMMARY OF THE DISCLOSURE

The following paragraphs are intended to introduce the reader to the more detailed description, not to define or limit the claimed subject matter of the present disclosure.

In one aspect, the present disclosure relates to morphinan alkaloid compounds.

In another aspect, the present disclosure relates to enzymes useful in the synthesis of morphinan alkaloid compounds.

Accordingly, in one aspect, the present disclosure provides, in at least one embodiment, a method of making a second morphinan compound having a saturated carbon bond at position $C_8$-$C_{14}$ and a mono-unsaturated bond at position $C_7$-$C_8$, the method comprising:
  (i) providing a first morphinan compound having a mono-unsaturated carbon bond at position $C_8$-$C_{14}$ and a saturated carbon bond at position $C_7$-$C_8$; and
  (ii) contacting the first morphinan compound with neopinone isomerase under reaction conditions permitting the conversion of the first morphinan compound into the second morphinan compound.

In some embodiments, the first and second morphinan compounds can possess a bridging oxygen atom between carbon atoms $C_4$ and $C_5$, forming a tetrahydrofuranyl ring within the morphinan chemical structure.

In some embodiments, the first morphinan compound can be a chemical compound having the chemical structure (I):

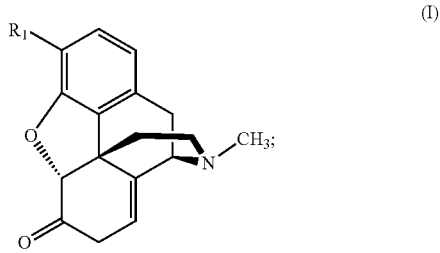

and
the second morphinan compound can be a chemical compound having the chemical structure (II):

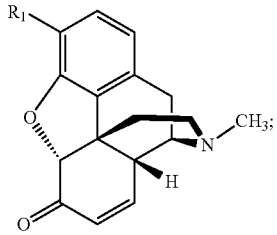
(II)

wherein $R_1$ is either a hydroxyl group, or a methoxy group.

In some embodiments, the method can further include a step c) comprising isolating the second morphinan compound.

In some embodiments, $R_1$ can be a methoxy group, and the method can further include reacting the second morphinan compound in the presence of codeinone reductase to form a third morphinan compound having the chemical structure (III):

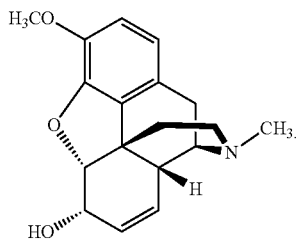
(III)

In some embodiments, the method can further include a step c) comprising isolating the third morphinan compound having chemical structure (III).

In some embodiments, additionally a fourth morphinan having the chemical structure (IV):

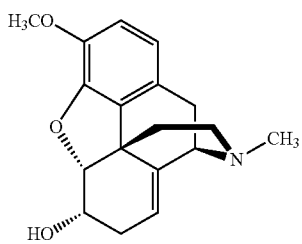
(IV)

can be formed, wherein the quantity of compound (IV) upon completion of the reaction does constitute no more than about 20% (w/w) of all morphinan compounds.

In some embodiments, compound (IV) upon completion of the reaction can constitute no more than about 15%, 14%, 13%, 12%, 11%, 10%, 9%, 8%, 7%, 6%, 5%, 4%, 3%, 2% of 1% (w/w) of all morphinan compounds.

In some embodiments, $R_1$ can be a methoxy group and the method further includes reacting the second morphinan compound in the presence of codeinone reductase to form a third morphinan compound having the chemical structure (III):

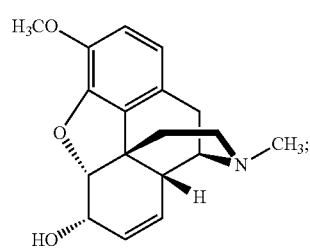
(III)

and
the method further includes reacting the third morphinan compound in the presence of codeinone-O-demethylase to form a fourth morphinan compound having the chemical structure (V):

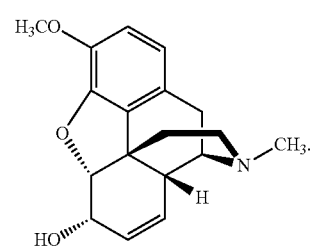
(V)

In some embodiments, the method can further include a step c) comprising isolating the fourth morphinan compound having chemical structure (V).

In some embodiments, $R_1$ can be a methoxy group and the method further includes reacting the second morphinan compound in the presence of morphinone reductase B to form a third morphinan compound selected from the morphinan compounds having the chemical structure (XIV):

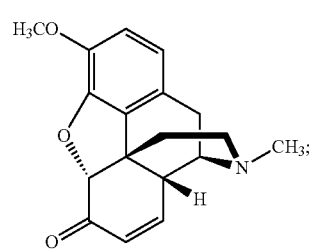
(XIV)

(XV)

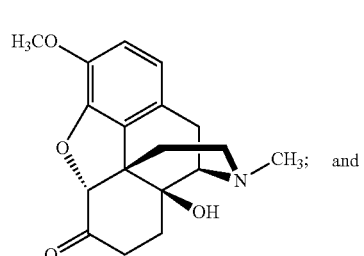
(XV)

and

-continued (XVI)

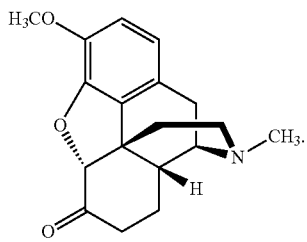

In some embodiments, the method can further include a step c) comprising isolating the third morphinan compound having chemical structure (XIV); (XV) or (XVI).

In some embodiments, $R_1$ can be a hydroxyl group and the method further includes reacting the second morphinan compound in the presence of codeinone reductase to form a third morphinan compound having the chemical structure (V).

In some embodiments, additionally a fourth morphinan compound having the chemical structure (VI):

(VI)

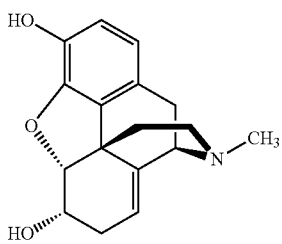

can be formed, wherein compound the quantity of compound (VI) upon completion of the reaction does constitute no more than about 20% (w/w) of all morphinan compounds.

In some embodiments, compound (VI) upon completion of the reaction can constitute no more than about 15%, 14%, 13%, 12%, 11%, 10%, 9%, 8%, 7%, 6%, 5%, 4%, 3%, 2% of 1% (w/w) of all morphinan compounds.

In some embodiments, $R_1$ can be a hydroxyl group and the method further includes reacting the second morphinan compound in the presence of morphinone reductase B to form a third morphinan compound selected from the morphinan compounds having the chemical structure (XVII):

(XVII)

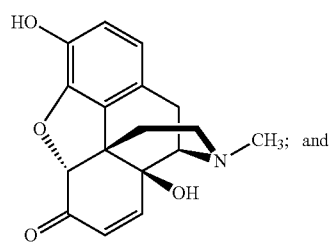

-continued (XVIII):

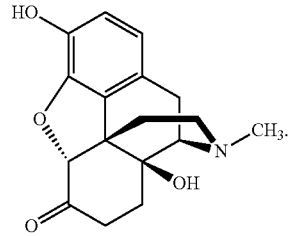

In some embodiments, the method can further include a step c) comprising isolating the third morphinan compound having chemical structure (XVII) or (XVIII).

In some embodiments, the first morphinan compound can be formed in a reaction comprising providing a precursor morphinan compound and converting the precursor morphinan compound to form the first morphinan compound.

In some embodiments, the precursor morphinan compound can be a morphinan compound having the chemical structure (VII):

(VII)

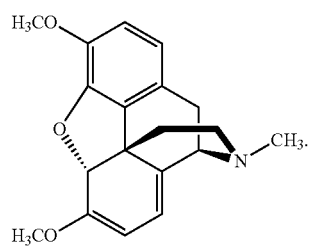

In some embodiments, the precursor morphinan compound can be a compound having chemical structure (VII) and the precursor compound is reacted in the presence of T6-O-demethylase to form the first morphinan compound, wherein in the first morphinan compound $R_1$ is a methoxy group.

In some embodiments, the morphinan precursor compound can be a morphinan compound having chemical structure (VIII):

(VIII)

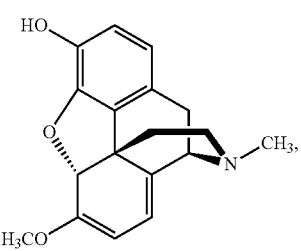

and the precursor morphinan compound is reacted in the presence of T6-O-demethylase, to form the first morphinan compound, wherein in the first morphinan compound $R_1$ is a hydroxyl group.

In some embodiments, the precursor compound can be a compound having chemical structure (VII) and the precursor compound is reacted in the presence of codeine-O-demethylase to form a further precursor compound having the chemical structure (VIII), and the further precursor compound is reacted in the presence of T6-O-demethylase, to form the first morphinan compound, wherein in the first morphinan compound $R_1$ is a hydroxyl group.

In some embodiments, the reaction conditions can be in vitro reaction conditions.

In some embodiments, the reaction conditions can be in vivo reaction conditions.

In some embodiments, the neopine isomerase can be a polypeptide encoded by a nucleic acid sequence comprising one or more nucleic acid sequences selected from:
(i) SEQ. ID NO: 14, SEQ. ID NO: 15, SEQ. ID NO: 16 and SEQ. ID NO: 17;
(ii) a nucleic acid sequence that is substantially identical to SEQ. ID NO: 14, SEQ. ID NO: 15, SEQ. ID NO: 16 or SEQ. ID NO: 17;
(iii) a nucleic acid sequence that is substantially identical to SEQ. ID NO: 14, SEQ. ID NO: 15, SEQ. ID NO: 16 or SEQ. ID NO: 17 but for the degeneration of the genetic code;
(iv) a nucleic acid sequence that is complementary to SEQ. ID NO: 14, SEQ. ID NO: 15, SEQ. ID NO: 16 or SEQ. ID NO: 17;
(v) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;
(vi) a nucleic acid sequence that encodes a functional variant of a polypeptide comprising one or more of the amino acid sequences set forth in SEQ. ID NO: 18, SEQ. ID NO: 19, SEQ. ID NO: 20 or SEQ. ID NO: 21; and
(vii) a nucleic acid sequence that hybridizes under stringent conditions to any one of the nucleic acid sequences set forth in (i), (ii), (iii), (iv), (v) or (vi).

In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the neopine isomerase can be a polypeptide encoded by a nucleic acid sequence comprising SEQ. ID NO: 14, SEQ. ID NO: 15, SEQ. ID NO; 16 and SEQ. ID NO: 17.

In some embodiments, the neopine isomerase can be a polypeptide encoded by a nucleic acid sequence selected from SEQ. ID NO: 1, SEQ. ID NO: 9, SEQ. ID NO: 12 and SEQ. ID NO: 53.

In some embodiments, the polypeptide comprising one or more of the amino acid sequences set forth in SEQ. ID NO: 18, SEQ. ID NO: 19, SEQ. ID NO: 20 or SEQ. ID NO: 21 can be selected from SEQ. ID NO: 2 and SEQ. ID NO: 54.

In another aspect, the present disclosure provides, in at least one embodiment, a method for preparing a second morphinan compound comprising:
(A) providing a chimeric nucleic acid sequence comprising as operably linked components:
  (a) a nucleic acid sequence encoding a neopinone isomerase polypeptide comprising one or more of the nucleic acid sequences selected from the group consisting of:
    (i) SEQ. ID NO: 14, SEQ. ID NO: 15, SEQ. ID NO: 16 and SEQ. ID NO: 17;
    (ii) a nucleic acid sequence that is substantially identical to SEQ. ID NO: 14, SEQ. ID NO: 15, SEQ. ID NO: 16 or SEQ. ID NO: 17;
    (iii) a nucleic acid sequence that is substantially identical to SEQ. ID NO: 14, SEQ. ID NO: 15, SEQ. ID NO: 16 or SEQ. ID NO: 17 but for the degeneration of the genetic code;
    (iv) a nucleic acid sequence that is complementary to SEQ. ID NO: 14, SEQ. ID NO: 15, SEQ. ID NO: 16 or SEQ. ID NO: 17;
    (v) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;
    (vi) a nucleic acid sequence that encodes a functional variant of a polypeptide comprising one or more of the amino acid sequences set forth in in SEQ. ID NO: 18, SEQ. ID NO: 19, SEQ. ID NO: 20 or SEQ. ID NO: 21; and
    (vii) a nucleic acid sequence that hybridizes under stringent conditions to any one of the nucleic acid sequences set forth in (i), (ii), (iii), (iv), (v) or (vi); and
  (b) one or more nucleic acid sequences capable of controlling expression in a host cell;
(B) introducing the chimeric nucleic acid sequence into a host cell capable of producing a first morphinan compound having the chemical structure (I):

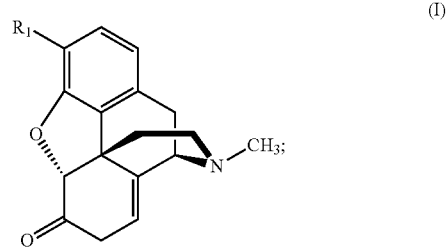

and
(C) growing the cell to produce a second morphinan having the chemical structure (II):

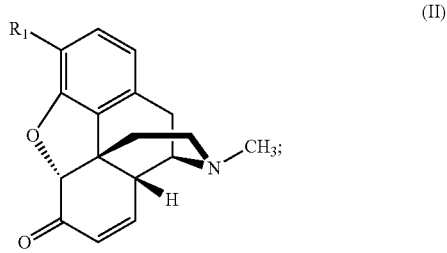

wherein $R_1$ is either a hydroxyl group, or a methoxy group.

In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the neopine isomerase can be a polypeptide encoded by a nucleic acid sequence comprising SEQ. ID NO: 14, SEQ. ID NO: 15, SEQ. ID NO; 16 and SEQ. ID NO: 17.

In some embodiments, the neopine isomerase can be a polypeptide encoded by a nucleic acid sequence selected from SEQ. ID NO: 1, SEQ. ID NO: 9, SEQ. ID NO: 12 and SEQ. ID NO: 53.

In some embodiments, the polypeptide comprising one or more of the amino acid sequences set forth in SEQ. ID NO: 18, SEQ. ID NO: 19, SEQ. ID NO: 20 or SEQ. ID NO: 21 can be selected from SEQ. ID NO: 2 and SEQ. ID NO: 54.

In some embodiments, the method can further include a step c) comprising isolating the second morphinan compound.

In some embodiments, $R_1$ can be a methoxy group, and the cell further includes a polynucleotide encoding a codeinone reductase capable of catalyzing a reaction, permitting the conversion of the second morphinan compound to form a third morphinan compound having the chemical structure (III):

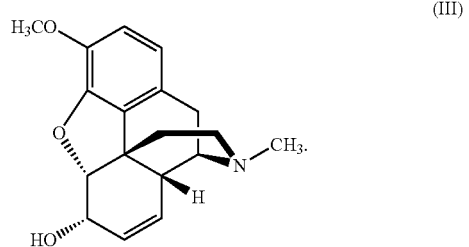

In some embodiments, the nucleic acid encoding the codeinone reductase can be operably linked to the nucleic acid comprising a nucleic acid sequence selected from (i); (ii); (iii); (iv); (v); and (vi).

In some embodiments, the method can further include a step c) comprising isolating the third morphinan compound having chemical structure (III).

In some embodiments, additionally a fourth morphinan having the chemical structure (IV):

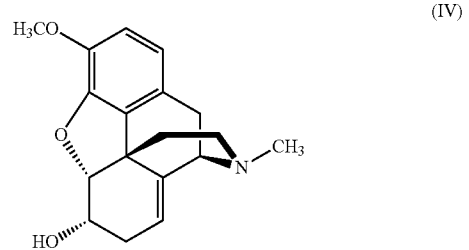

can be formed, wherein the quantity of compound (IV) upon completion of the reaction does constitute no more than about 20% (w/w) of all morphinan compounds.

In some embodiments, compound (IV) upon completion of the reaction can constitute no more than about 15%, 14%, 13%, 12%, 11%, 10%, 9%, 8%, 7%, 6%, 5%, 4%, 3%, 2% of 1% (w/w) of all morphinan compounds.

In some embodiments, $R_1$ can be a methoxy group and the cell further includes a polynucleotide encoding a codeinone reductase capable of catalyzing a reaction permitting the conversion of the second morphinan compound in the presence of codeinone reductase to form a third morphinan compound having the chemical structure (III):

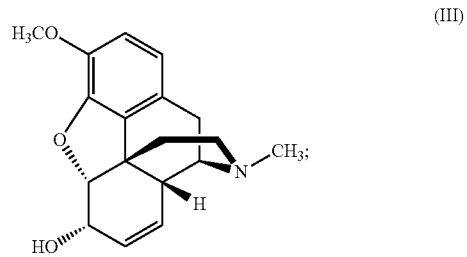

and
the cell further includes a polynucleotide encoding a codeine-O-demethylase capable of catalyzing a reaction permitting the conversion of the third morphinan compound in the presence of codeine-O-demethylase to form a fourth morphinan compound having the chemical structure (V):

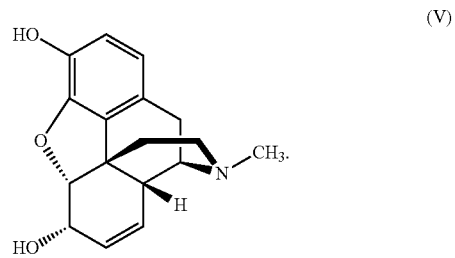

In some embodiments, the nucleic acid encoding the codeinone reductase or the nucleic acid encoding the codeine-O-demethylase can be operably linked to the nucleic acid comprising a nucleic acid sequence selected from (i); (ii); (iii); (iv); (v); and (vi).

In some embodiments, the method can further include a step c) comprising isolating the fourth morphinan compound having chemical structure (V).

In some embodiments, $R_1$ can be a hydroxyl group and the cell further includes a nucleic acid encoding a codeinone reductase capable of catalyzing a reaction permitting the conversion of the second morphinan in the presence of codeinone reductase to form a third morphinan compound having the chemical structure (V).

In some embodiments, additionally a fourth morphinan having the chemical structure (VI):

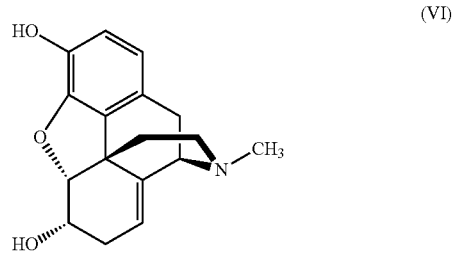

is formed, wherein compound the quantity of compound (VI) upon completion of the reaction does constitute no more than about 20% (w/w) of all morphinan compounds.

In some embodiments, compound (VI) upon completion of the reaction can constitute no more than about 15%, 14%, 13%, 12%, 11%, 10%, 9%, 8%, 7%, 6%, 5%, 4%, 3%, 2% of 1% (w/w) of all morphinan compounds.

In some embodiments, the first morphinan can be formed in a reaction in the cell, the reaction comprising converting a precursor morphinan compound to form the first morphinan.

In some embodiments, the precursor compound can be a compound having the chemical structure (VII):

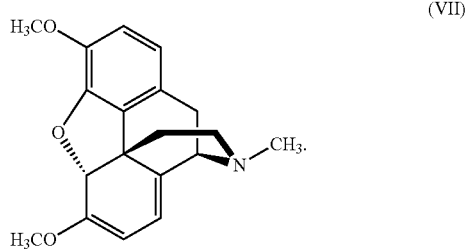

In some embodiments, the precursor compound can be a compound having chemical structure (VII), the cell can comprise T6-O-demethylase, and wherein the first morphinan compound $R_1$ can be a methoxy group.

In some embodiments, the precursor compound can be a compound having chemical structure (VIII):

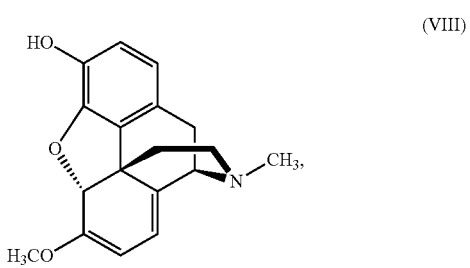

wherein the cell can comprise T6-O-demethylase, and wherein the first morphinan $R_1$ can be a hydroxyl group.

In some embodiments, the precursor compound can be a compound having chemical structure (VIII), the cell can comprise T6-O-demethylase, and in the first morphinan compound $R_1$ can be a hydroxyl group.

In some embodiments, the precursor compound can be a compound having chemical structure (VII), the cell comprises codeine-O-demethylase catalyzing a reaction to form a further precursor compound having the chemical structure (VIII) from precursor compound (VII), and the cell further comprises T6-O-demethylase, to form the first morphinan compound from the precursor compound having the chemical structure (VIII), wherein in the first morphinan compound $R_1$ is a hydroxyl group.

In another aspect, the present disclosure provides, in at least one embodiment, a substantially pure nucleic acid comprising one or more of the nucleic acid sequences selected from the group consisting of:
(i) SEQ. ID NO: 14, SEQ. ID NO: 15, SEQ. ID NO: 16 and SEQ. ID NO: 17;
(ii) a nucleic acid sequence that is substantially identical to SEQ. ID NO: 14, SEQ. ID NO: 15, SEQ. ID NO: 16 or SEQ. ID NO: 17;
(iii) a nucleic acid sequence that is substantially identical to SEQ. ID NO: 14, SEQ. ID NO: 15, SEQ. ID NO: 16 or SEQ. ID NO: 17 but for the degeneration of the genetic code;
(iv) a nucleic acid sequence that is complementary to SEQ. ID NO: 14, SEQ. ID NO: 15, SEQ. ID NO: 16 or SEQ. ID NO: 17;
(iv) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;
(vi) a nucleic acid sequence that encodes a functional variant of a polypeptide comprising one or more of the amino acid sequences set forth in in SEQ. ID NO: 18, SEQ. ID NO: 19, SEQ. ID NO: 20 or SEQ. ID NO: 21; and
(vii) a nucleic acid sequence that hybridizes under stringent conditions to any one of the nucleic acid sequences set forth in (i), (ii), (iii), (iv), (v) or (vi).

In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the neopine isomerase can be a polypeptide encoded by a nucleic acid sequence comprising SEQ. ID NO: 14, SEQ. ID NO: 15, SEQ. ID NO; 16 and SEQ. ID NO: 17.

In some embodiments, the nucleic acid sequence encodes a neopine isomerase and can be selected from SEQ. ID NO: 1, SEQ. ID NO: 9, SEQ. ID NO: 12 and SEQ. ID NO: 53.

In some embodiments the polypeptide comprising one or more of the amino acid sequences set forth in SEQ. ID NO: 18, SEQ. ID NO: 19, SEQ. ID NO: 20 or SEQ. ID NO: 21 can be selected from SEQ. ID NO: 2 and SEQ. ID NO: 54.

In another aspect, the present disclosure provides, in at least one embodiment, a substantially pure protein comprising:
(i) a polypeptide comprising one or more of the amino acid sequences set forth in SEQ. ID NO: 18, SEQ. ID NO: 19, SEQ. ID NO: 20, or SEQ. ID NO: 21; or
(ii) a functional variant of a polypeptide comprising one or more of the amino acid sequences set forth in SEQ. ID NO: 18, SEQ. ID NO: 19, SEQ. ID NO: 20 or SEQ. ID NO: 21.

In some embodiments, SEQ. ID NO: 18, SEQ. ID NO: 19, SEQ. ID NO: 20 or SEQ. ID NO: 21 can comprise an amino acid sequence that is at least 90% identical, at least 91% identical, at least 92% identical, at least 93% identical, at least 94% identical at least 95%, at least 96%, at least 97%, at least 98%, or at least 99% identical to SEQ. ID NO: 18; SEQ. ID NO: 19; SEQ. ID NO: 20; or SEQ. ID NO: 21, respectively.

In some embodiments, the neopine isomerase can be a polypeptide encoded by a nucleic acid sequence comprising SEQ. ID NO: 18, SEQ. ID NO: 19, SEQ. ID NO; 20 and SEQ. ID NO: 21.

In some embodiments, the substantially pure protein can comprise SEQ. ID NO: 2, or SEQ. ID NO: 54.

In another aspect, the present disclosure provides, in at least one embodiment, a chimeric nucleic acid sequence comprising as operably linked components:

(a) a nucleic acid sequence encoding a neopinone isomerase, the nucleic acid sequence comprising one or more nucleic acid sequences selected from the group consisting of:
  (i) SEQ. ID NO: 14, SEQ. ID NO: 15, SEQ. ID NO: 16 and SEQ. ID NO: 17;
  (ii) a nucleic acid sequence that is substantially identical to SEQ. ID NO: 14, SEQ. ID NO: 15, SEQ. ID NO: 16 or SEQ. ID NO: 17;
  (iii) a nucleic acid sequence that is substantially identical to SEQ. ID NO: 14, SEQ. ID NO: 15, SEQ. ID NO: 16 or SEQ. ID NO: 17 but for the degeneration of the genetic code;
  (iv) a nucleic acid sequence that is complementary to SEQ. ID NO: 14, SEQ. ID NO: 15, SEQ. ID NO: 16 or SEQ. ID NO: 17;
  (v) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;
  (vi) a nucleic acid sequence that encodes a functional variant of a polypeptide comprising one or more of the amino acid sequences set forth in in SEQ. ID NO: 18, SEQ. ID NO: 19, SEQ. ID NO: 20 or SEQ. ID NO: 21; and
  (vii) a nucleic acid sequence that hybridizes under stringent conditions to any one of the nucleic acid sequences set forth in (i), (ii), (iii), (iv), (v) or (vi); and
(b) a nucleic acid sequence capable of controlling expression of neopinone isomerase in a host cell.

In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the neopine isomerase can be a polypeptide encoded by a nucleic acid sequence comprising SEQ. ID NO: 14, SEQ. ID NO: 15, SEQ. ID NO; 16 and SEQ. ID NO: 17.

In some embodiments, the neopine isomerase can be a polypeptide encoded by a nucleic acid sequence selected from SEQ. ID NO: 1, SEQ. ID NO: 9, SEQ. ID NO: 12 and SEQ. ID NO: 53.

In some embodiments, the polypeptide comprising one or more of the amino acid sequences set forth in SEQ. ID NO: 18, SEQ. ID NO: 19, SEQ. ID NO: 20 or SEQ. ID NO: 21 can be selected from SEQ. ID NO: 2 and SEQ. ID NO: 54.

In another aspect, the present disclosure provides, in at least one embodiment, a recombinant expression vector comprising as operably linked components:
(a) a nucleic acid sequence capable of controlling expression in a host cell; and
(b) a nucleic acid sequence encoding a neopinone isomerase, the nucleic acid sequence comprising one or more nucleic acid sequences selected from the group consisting of:
  (i) SEQ. ID NO: 14, SEQ. ID NO: 15, SEQ. ID NO: 16 and SEQ. ID NO: 17;
  (ii) a nucleic acid sequence that is substantially identical to SEQ. ID NO: 14, SEQ. ID NO: 15, SEQ. ID NO: 16 or SEQ. ID NO: 17;
  (iii) a nucleic acid sequence that is substantially identical to SEQ. ID NO: 14, SEQ. ID NO: 15, SEQ. ID NO: 16 or SEQ. ID NO: 17 but for the degeneration of the genetic code;
  (iv) a nucleic acid sequence that is complementary to SEQ. ID NO: 14, SEQ. ID NO: 15, SEQ. ID NO: 16 or SEQ. ID NO: 17;
  (v) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;
  (vi) a nucleic acid sequence that encodes a functional variant of a polypeptide comprising one or more of the amino acid sequences set forth in in SEQ. ID NO: 18, SEQ. ID NO: 19, SEQ. ID NO: 20 or SEQ. ID NO: 21; and
  (vii) a nucleic acid sequence that hybridizes under stringent conditions to any one of the nucleic acid sequences set forth in (i), (ii), (iii), (iv), (v) or (vi); and
wherein the expression vector is suitable for expression in a host cell.

In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the neopine isomerase can be a polypeptide encoded by a nucleic acid sequence comprising SEQ. ID NO: 14, SEQ. ID NO: 15, SEQ. ID NO; 16 and SEQ. ID NO: 17.

In some embodiments, the neopine isomerase can be a polypeptide encoded by a nucleic acid sequence selected from SEQ. ID NO: 1, SEQ. ID NO: 9, SEQ. ID NO: 12 and SEQ. ID NO: 53.

In some embodiments, the polypeptide comprising one or more of the amino acid sequences set forth in SEQ. ID NO: 18, SEQ. ID NO: 19, SEQ. ID NO: 20 or SEQ. ID NO: 21 can be selected from SEQ. ID NO: 2 and SEQ. ID NO: 54.

In another aspect, the present disclosure provides, in at least one embodiment, a host cell comprising a recombinant polynucleotide comprising a nucleic acid sequence selected from the group consisting of:
  (i) SEQ. ID NO: 14, SEQ. ID NO: 15, SEQ. ID NO: 16 and SEQ. ID NO: 17;
  (ii) a nucleic acid sequence that is substantially identical to SEQ. ID NO: 14, SEQ. ID NO: 15, SEQ. ID NO: 16 or SEQ. ID NO: 17;
  (iii) a nucleic acid sequence that is substantially identical to SEQ. ID NO: 14, SEQ. ID NO: 15, SEQ. ID NO: 16 or SEQ. ID NO: 17 but for the degeneration of the genetic code;
  (iv) a nucleic acid sequence that is complementary to SEQ. ID NO: 14, SEQ. ID NO: 15, SEQ. ID NO: 16 or SEQ. ID NO: 17;
  (v) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;
  (vi) a nucleic acid sequence that encodes a functional variant of a polypeptide comprising one or more of the amino acid sequences set forth in in SEQ. ID NO: 18, SEQ. ID NO: 19, SEQ. ID NO: 20 or SEQ. ID NO: 21; and (vii) a nucleic acid sequence that hybridizes under stringent conditions to any one of the nucleic acid sequences set forth in (i), (ii), (iii), (iv), (v) or (vi); and In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the neopine isomerase can be a polypeptide encoded by a nucleic acid sequence comprising SEQ. ID NO: 14, SEQ. ID NO: 15, SEQ. ID NO; 16 and SEQ. ID NO: 17.

In some embodiments, the neopine isomerase can be a polypeptide encoded by a nucleic acid sequence selected from SEQ. ID NO: 1, SEQ. ID NO: 9, SEQ. ID NO: 12 and SEQ. ID NO: 53.

In some embodiments, the polypeptide comprising one or more of the amino acid sequences set forth in SEQ. ID NO: 18, SEQ. ID NO: 19, SEQ. ID NO: 20 or SEQ. ID NO: 21 can be selected from SEQ. ID NO: 2 and SEQ. ID NO: 54.

In another aspect, the present disclosure provides, a method of making neopinone isomerase, the method comprising:
(a) providing a chimeric nucleic acid sequence comprising as operably linked components:
  (I) a nucleic acid sequence encoding a neopinone isomerase selected from the group consisting of:
    (i) SEQ. ID NO: 14, SEQ. ID NO: 15, SEQ. ID NO: 16 and SEQ. ID NO: 17;
    (ii) a nucleic acid sequence that is substantially identical to SEQ. ID NO: 14, SEQ. ID NO: 15, SEQ. ID NO: 16 or SEQ. ID NO: 17;
    (iii) a nucleic acid sequence that is substantially identical to SEQ. ID NO: 14, SEQ. ID NO: 15, SEQ. ID NO: 16 or SEQ. ID NO: 17 but for the degeneration of the genetic code;
    (iv) a nucleic acid sequence that is complementary to SEQ. ID NO: 14, SEQ. ID NO: 15, SEQ. ID NO: 16 or SEQ. ID NO: 17;
    (v) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;
    (vi) a nucleic acid sequence that encodes a functional variant of a polypeptide comprising one or more of the amino acid sequences set forth in in SEQ. ID NO: 18, SEQ. ID NO: 19, SEQ. ID NO: 20 or SEQ. ID NO: 21; and
    (vii) a nucleic acid sequence that hybridizes under stringent conditions to any one of the nucleic acid sequences set forth in (i), (ii), (iii), (iv), (v) or (vi); and
  (II) one or more nucleic acid sequences capable of controlling expression in a host cell;
(b) introducing the chimeric nucleic acid sequence into a host cell and growing the host cell to produce the neopinone isomerase; and
(c) recovering the neopinone isomerase from the host cell.

In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the neopine isomerase can be a polypeptide encoded by a nucleic acid sequence comprising SEQ. ID NO: 14, SEQ. ID NO: 15, SEQ. ID NO; 16 and SEQ. ID NO: 17.

In some embodiments, the neopine isomerase can be a polypeptide encoded by a nucleic acid sequence selected from SEQ. ID NO: 1, SEQ. ID NO: 9, SEQ. ID NO: 12 and SEQ. ID NO: 53.

In some embodiments, the polypeptide comprising one or more of the amino acid sequences set forth in SEQ. ID NO: 18, SEQ. ID NO: 19, SEQ. ID NO: 20 or SEQ. ID NO: 21 can be selected from SEQ. ID NO: 2 and SEQ. ID NO: 54.

In another aspect, the present disclosure provides, in at least one embodiment, a use of a neopinone isomerase as a catalytic agent in a reaction to make a second morphinan compound having a saturated carbon bond at position $C_8$-$C_{14}$ and a mono-unsaturated carbon bond at position $C_7$-$C_8$, using a first morphinan compound having a mono-unsaturated carbon bond at position $C_8$-$C_{14}$ and a saturated carbon bond at position $C_7$-$C_8$ as a substrate.

In some embodiments, the first and second morphinan compound can possess a bridging oxygen atom between carbon atoms $C_4$ and $C_5$, forming a tetrahydrofuranyl ring within the morphinan chemical structure.

In some embodiments, the first morphinan compound can be a chemical compound having the chemical structure (I):

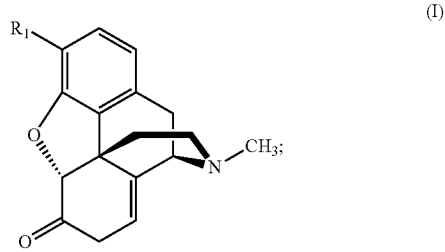

and
the second morphinan compound can be a chemical compound having the chemical structure (II):

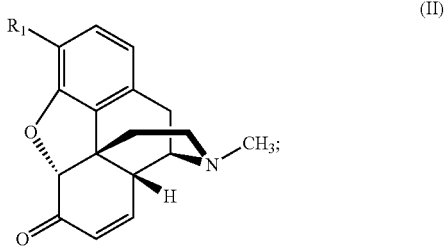

wherein $R_1$ is either a hydroxyl group, or a methoxy group.

In another aspect, the present disclosure provides, in at least one embodiment, a pharmaceutical composition comprising a morphinan compound prepared in accordance with any one of the methods of the present disclosure.

In another aspect, the present disclosure provides, in at least one embodiment, a use of a morphinan compound prepared in accordance with any one of the methods of the present disclosure to prepare a pharmaceutical composition comprising the morphinan compound.

In another aspect, the present disclosure provides, in at least one embodiment, a method for treating a patient with a morphinan compound prepared according to the methods of the present disclosure, the method comprising administering to the patient a pharmaceutical composition comprising a morphinan compound, wherein the pharmaceutical composition is administered in an amount sufficient to ameliorate a medical condition in the patient.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

FIG. 10 depicts certain experimental results, notably bar graphs obtained in the performance of a neopine isomerase gene silencing experiment. Shown are the production of NISO transcript (FIG. 10A), thebaine (FIG. 10B), codeinone (FIG. 10C), neopine (FIG. 10D), codeine (FIG. 10E) and morphine (FIG. 10F), in each case in the presence of *P. somniferum* tissue transformed with empty vector (pTRV2), or with a vector designed to silence NISO expression (pNISO).

FIG. 11 depicts an amino acid sequence alignment of NISO (SEQ. ID NO: 2) and PR-polypeptides including notably: PR10-8 (SEQ. ID NO: 38); PR10-9 (SEQ. ID NO: 40); PR10-10 (SEQ. ID NO: 42); PR10-5 (SEQ. ID NO: 34); PR10-4 (SEQ. ID NO: 32), PR10-11 (SEQ. ID NO: 44); PR10-12 (SEQ. ID NO: 46); MLP15 (SEQ. ID NO: 30); MLP1 (SEQ. ID NO: 56), MLP2 (SEQ. ID NO: 24); MLP3 (SEQ. ID NO: 26); MLP4 (SEQ. ID NO: 28); PR10-14 (SEQ. ID NO: 50); PR10-15 (SEQ. ID NO: 30); and a thebaine synthase polypeptide (SEQ. ID NO: 58). Various Domains are indicated, notably Domain 1 (1) (including Subdomain 1a (1a), and Subdomain 1b (1b)); Domain 2 (2) (including Subdomain 2a (2a), and Subdomain 2b (2b)); Domain 3 (3); and Domain 4 (4). Identical amino acid residues are highlighted in black for ease of comparison. It is noted that an interspersed sequence that is unique to PR10-14, starting at amino acid 121 and ending at amino acid 214 is shown highlighted in grey. The interspersed sequence is shown separately in order to permit alignment between PR10-14 and the other sequences shown.

Figure 1A:
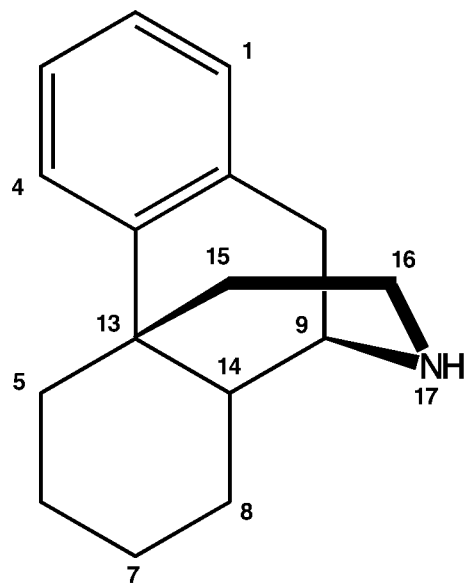
FIG. 1 depicts a prototype chemical structure of a morphinan (FIG. 1A) and furanyl morphinan (FIG. 1B). Various atoms within the chemical structures have been numbered for ease of reference.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

The term "or" is inclusive unless modified, for example, by "either".

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g. a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent or patent application was specifically and individually indicated to be incorporated by reference in its entirety.

Terms and Definitions

Figure 1B:
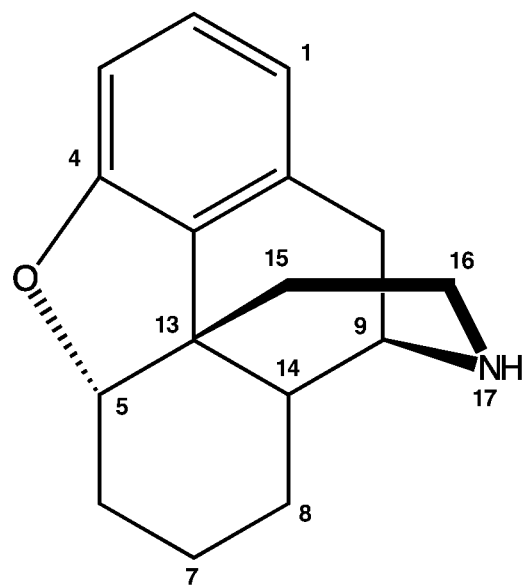

The terms "morphinan", "morphinan alkaloid compound", "morphinan" alkaloid", or "morphinan compound", as may be used interchangeably herein, refer to a class of molecules having the prototype chemical structure shown in FIG. 1A, and includes compounds having the prototype chemical structure shown in FIG. 1B. Certain specific carbon and nitrogen atoms can be referred herein by reference to their position within the morphinan chemical structure e.g. $C_1$, $C_2$, $N_{17}$ etc. Various modifications to the prototype chemical structures are possible, and morphinans include, for example, compounds wherein the $C_3$ carbon atom comprises a hydroxyl side group, or a methoxy side group, the $C_6$ carbon atom comprises a hydroxyl group or an oxo group, and wherein the nitrogen atom $N_{17}$ comprises a methyl side group.

The term "furanyl morphinan", as used herein, refers to a class of chemical compounds having the prototype chemical structure as shown in FIG. 1B. Furanyl morphinans can be derived from morphinan compounds having the chemical structure shown in FIG. 1A by the formation of a tetrahydrofuranyl ring chemical structure established by a bridging oxygen atom between $C_4$ and $C_5$. It is noted that the tetrahydrofuranyl ring can also be referred to as a dihydrofuranyl chemical structure due to benzene resonance.

Figure 2A:
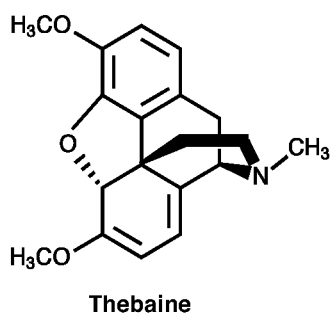
FIG. 2 depicts the chemical structures of certain morphinan compounds: thebaine (FIG. 2A); neopinone (FIG. 2B); neopine (FIG. 2C); codeinone (FIG. 2D); oripavine (FIG. 2E) neomorphinone (FIG. 2F); neomorphine (FIG. 2G); and morphinone (FIG. 2H).

The term "thebaine", as used herein, refers to a chemical compound having the chemical structure set forth in FIG. 2A.

Figure 2B:
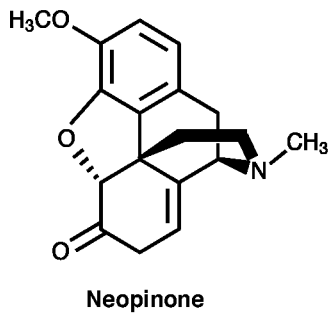

The term "neopinone", as used herein, refers to a chemical compound having the chemical structure set forth in FIG. 2B.

Figure 2C:
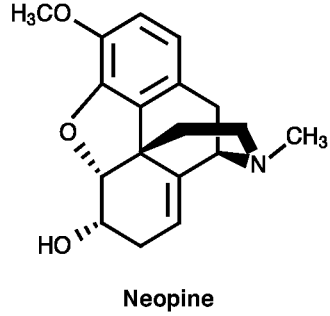

The term "neopine", as used herein, refers to a chemical compound having the chemical structure set forth in FIG. 2C.

Figure 2D:
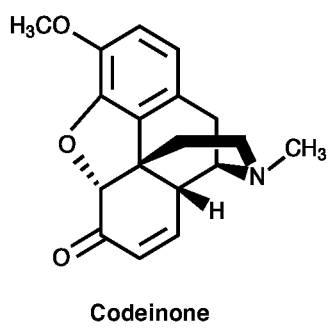

The term "codeinone", as used herein, refers to a chemical compound having the chemical structure set forth in FIG. 2D.

Figure 2E:
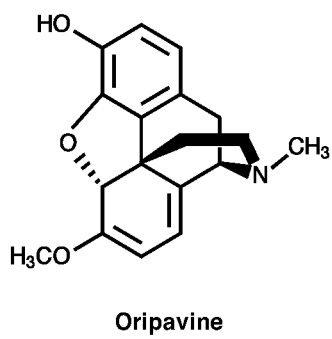

The term "oripavine", as used herein, refers to a chemical compound having the chemical structure set forth in FIG. 2E.

Figure 2F:
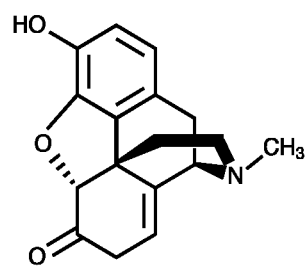

The term "neomorphinone", as used herein, refers to a chemical compound having the chemical structure set forth in FIG. 2F.

Figure 2G:
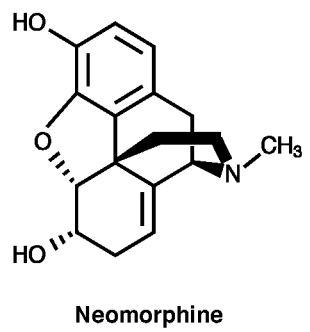

The term "neomorphine", as used herein, refers to a chemical compound having the chemical structure set forth in FIG. 2G.

Figure 2H:
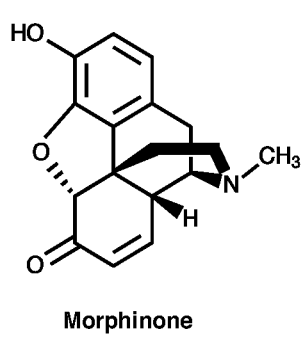

The term "morphinone", as used herein, refers to a chemical compound having the chemical structure set forth in FIG. 2H.

Figure 3A:
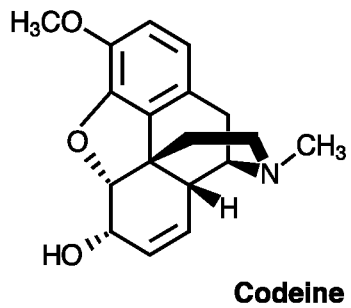
FIG. 3 depicts the chemical structures of certain further morphinan compounds: codeine (FIG. 3A); morphine (FIG. 3B); hydrocodone (FIG. 3C); 14-hydroxycodeinone (FIG. 3D); oxycodone (FIG. 3E); 14-hydroxymorphinone (FIG. 3F); and oxymorphinone (FIG. 3G).

The term "codeine", as used herein, refers to a chemical compound having the chemical structure set forth in FIG. 3A.

Figure 3B:
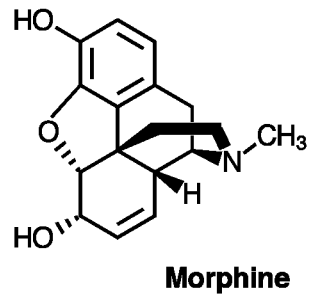

The term "morphine", as used herein, refers to a chemical compound having the chemical structure set forth in FIG. 3B.

Figure 3C:
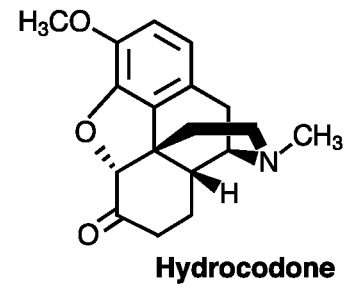

The term "hydrocodone", as used herein, refers to a chemical compound having the chemical structure set forth in FIG. 3C.

Figure 3D:
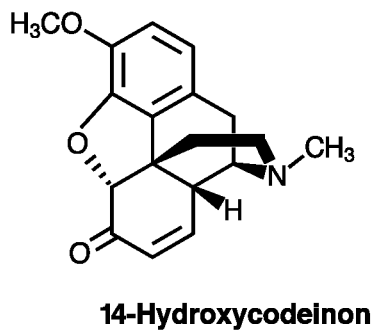

The term "14-hydroxycodeinone", as used herein, refers to a chemical compound having the chemical structure set forth in FIG. 3D.

Figure 3E:
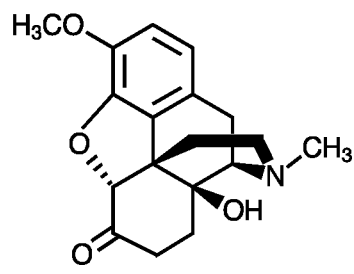

The term "oxycodone", as used herein, refers to a chemical compound having the chemical structure set forth in FIG. 3E.

Figure 3F:
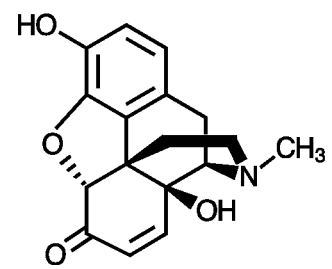

The term "14-hydroxymorpinone", as used herein, refers to a chemical compound having the structure set forth in FIG. 3F.

Figure 3G:
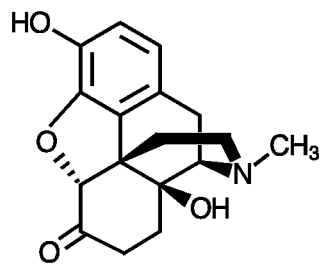

The term "oxymorphone", as used herein, refers to a chemical compound having the structure set forth in FIG. 3G.

The terms "neopinone isomerase" or "NISO", as may be used interchangeably herein, refer to any and all proteins comprising a sequence of amino acid residues which is (i) substantially identical to the amino acid sequences constituting any neopinone isomerase polypeptide set forth herein, including, for example, SEQ. ID NO: 2, and SEQ. ID NO: 54 or (ii) encoded by a nucleic acid sequence capable of hybridizing under at least moderately stringent conditions to any nucleic acid sequence encoding any neopinone isomerase polypeptide set forth herein, but for the use of synonymous codons, provided however that, neopinone isomerases, exclude any and all PR-Proteins, and further include all neopinone isomerases set forth herein.

The terms "codeinone reductase" or "COR", as may be used interchangeably herein, refer to any and all enzymes comprising a sequence of amino acid residues which is (i) substantially identical to the amino acid sequences constituting any codeinone reductase polypeptide set forth herein, including, for example, SEQ. ID NO: 4, or (ii) encoded by a nucleic acid sequence capable of hybridizing under at least moderately stringent conditions to any nucleic acid sequence encoding any codeinone reductase polypeptide set forth herein, but for the use of synonymous codons.

The terms "T6-O-demethylase" or "T6ODM", as may be used interchangeably herein, refer to any and all enzymes comprising a sequence of amino acid residues which is (i) substantially identical to the amino acid sequences constituting any T6-O-demethylase polypeptide set forth herein, including, for example, SEQ. ID NO: 6, or (ii) encoded by a nucleic acid sequence capable of hybridizing under at least moderately stringent conditions to any nucleic acid sequence encoding any T6-O-demethylase polypeptide set forth herein, but for the use of synonymous codons.

The terms "codeine-O-demethylase" or "CODM", as may be used interchangeably herein, refer to any and all enzymes comprising a sequence of amino acid residues which is (i) substantially identical to the amino acid sequences constituting any codeine-O-demethylase polypeptide set forth herein, including, for example, SEQ. ID NO: 8, or (ii) encoded by a nucleic acid sequence capable of hybridizing under at least moderately stringent conditions to any nucleic acid sequence encoding any codeine-O-demethylase polypeptide set forth herein, but for the use of synonymous codons.

The terms "morphinone reductase B" or "MorB", as may be used interchangeably herein, refer to any and all enzymes comprising a sequence of amino acid residues which is (i) substantially identical to the amino acid sequences constituting any morphinone reductase B polypeptide set forth herein, including, for example, SEQ. ID NO: 22, or (ii) encoded by a nucleic acid sequence capable of hybridizing under at least moderately stringent conditions to any nucleic acid sequence encoding any morphinone reductase B polypeptide set forth herein, but for the use of synonymous codons.

The term "PR-protein" refers to any and all proteins comprising a sequence of amino acid residues which is (i) substantially identical to the amino acid sequences constituting any PR protein polypeptide set forth herein, including, for example, SEQ. ID NO: 38, or (ii) encoded by a nucleic acid sequence capable of hybridizing under at least moderately stringent conditions to any nucleic acid sequence encoding any PR-protein polypeptide set forth herein, but for the use of synonymous codons, provided however that, PR-proteins, exclude any and all neopine isomerases, and further include all PR-proteins set forth herein.

The terms "nucleic acid sequence encoding neopinone isomerase", and "nucleic acid sequence encoding a neopinone isomerase polypeptide", as may be used interchangeably herein, refer to any and all nucleic acid sequences encoding a neopinone isomerase polypeptide, including, for example, SEQ. ID NO: 1, SEQ. ID NO: 9, SEQ. ID NO: 12, and SEQ. ID NO: 53. Nucleic acid sequences encoding a neopinone isomerase polypeptide further include any and all nucleic acid sequences which (i) encode polypeptides that are substantially identical to the neopinone isomerase polypeptide sequences set forth herein; or (ii) hybridize to any neopinone isomerase nucleic acid sequences set forth herein under at least moderately stringent hybridization conditions or which would hybridize thereto under at least moderately stringent conditions but for the use of synonymous codons.

The terms "nucleic acid sequence encoding codeinone reductase", and "nucleic acid sequence encoding a codeinone reductase polypeptide", as may be used interchangeably herein, refer to any and all nucleic acid sequences encoding a codeinone reductase polypeptide, including, for example, SEQ. ID NO: 3. Nucleic acid sequences encoding a codeinone reductase polypeptide further include any and all nucleic acid sequences which (i) encode polypeptides that are substantially identical to the codeinone reductase polypeptide sequences set forth herein; or (ii) hybridize to any codeinone reductase nucleic acid sequences set forth herein under at least moderately stringent hybridization conditions or which would hybridize thereto under at least moderately stringent conditions but for the use of synonymous codons.

The terms "nucleic acid sequence encoding T6-O-demethylase", and "nucleic acid sequence encoding a T6-O-demethylase polypeptide", as may be used interchangeably herein, refer to any and all nucleic acid sequences encoding a T6-O-demethylase polypeptide, including, for example, SEQ. ID NO: 5. Nucleic acid sequences encoding a T6-O-demethylase polypeptide further include any and all nucleic acid sequences which (i) encode polypeptides that are substantially identical to the T6-O-demethylase polypeptide sequences set forth herein; or (ii) hybridize to any T6-O-demethylase nucleic acid sequences set forth herein under at least moderately stringent hybridization conditions or which would hybridize thereto under at least moderately stringent conditions but for the use of synonymous codons.

The terms "nucleic acid sequence encoding codeine-O-demethylase", and "nucleic acid sequence encoding a codeine-O-demethylase polypeptide", as may be used interchangeably herein, refer to any and all nucleic acid sequences encoding a codeine-O-demethylase polypeptide, including, for example, SEQ. ID NO: 7. Nucleic acid sequences encoding a codeine-O-demethylase polypeptide further include any and all nucleic acid sequences which (i) encode polypeptides that are substantially identical to the codeine-O-demethylase polypeptide sequences set forth herein; or (ii) hybridize to any codeine-O-demethylase nucleic acid sequences set forth herein under at least moderately stringent hybridization conditions or which would hybridize thereto under at least moderately stringent conditions but for the use of synonymous codons.

The terms "nucleic acid sequence encoding morphinone reductase B", and "nucleic acid sequence encoding a morphinone reductase B polypeptide", as may be used interchangeably herein, refer to any and all nucleic acid sequences encoding a morphinone reductase B polypeptide, including, for example, SEQ. ID NO: 13. Nucleic acid sequences encoding a morphinone reductase B polypeptide further include any and all nucleic acid sequences which (i) encode polypeptides that are substantially identical to the morphinone reductase B polypeptide sequences set forth herein; or (ii) hybridize to any morphinone reductase B nucleic acid sequences set forth herein under at least moderately stringent hybridization conditions or which would hybridize thereto under at least moderately stringent conditions but for the use of synonymous codons.

The terms "nucleic acid sequence encoding a PR-protein, and "nucleic acid sequence encoding a "PR-polypeptide", as may be used interchangeably herein, refer to any and all nucleic acid sequences encoding a PR-polypeptide, including, for example, SEQ. ID NO: 37. Nucleic acid sequences encoding a PR-polypeptide further include any and all nucleic acid sequences which (i) encode polypeptides that are substantially identical to PR-polypeptide sequences set forth herein; or (ii) hybridize to any nucleic PR-polypeptide encoding nucleic acid sequences set forth herein under at least moderately stringent hybridization conditions or which would hybridize thereto under at least moderately stringent conditions but for the use of synonymous codons, provided however that, nucleic acid sequences encoding PR-polypeptides, exclude any and all nucleic acid sequences encoding neopine isomerases, and further include all nucleic acid sequences encoding PR-polypeptides set forth herein.

The terms "polynucleotide", "nucleic acid" or "nucleic acid sequence" as used herein, refer to a sequence of nucleoside or nucleotide monomers, consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic polynucleotides (DNA) or ribonucleic acid polynucleotides (RNA) and may include naturally occurring bases including adenine, guanine, cytosine, thymidine and uracil. The nucleic acid sequences may also contain modified bases. Examples of such modified bases include aza and deaza adenine, guanine, cytosine, thymidine and uracil, and xanthine and hypoxanthine. A sequence of nucleotide or nucleoside monomers may be referred to as a polynucleotide sequence, nucleic acid sequence, a nucleotide sequence or a nucleoside sequence.

The term "polypeptide", as used herein in conjunction with a reference SEQ. ID NO, refers to any and all polypeptides comprising a sequence of amino acid residues which is (i) substantially identical to the amino acid sequence constituting the polypeptide having such reference SEQ. ID NO, or (ii) encoded by a nucleic acid sequence capable of hybridizing under at least moderately stringent conditions to any nucleic acid sequence encoding the polypeptide having such reference SEQ. ID NO, but for the use of synonymous codons. A sequence of amino acid residues may be referred to as an amino acid sequence, or polypeptide sequence.

The terms "nucleic acid sequence encoding a polypeptide" or "nucleic acid encoding a polypeptide", as used herein in conjunction with a reference SEQ. ID NO, refers to any and all nucleic acid sequences encoding a polypeptide having such reference SEQ. ID NO. Nucleic acid sequences encoding a polypeptide, in conjunction with a reference SEQ. ID NO, further include any and all nucleic acid sequences which (i) encode polypeptides that are substantially identical to the polypeptide having such reference SEQ. ID NO; or (ii) hybridize to any nucleic acid sequences encoding polypeptides having such reference SEQ. ID NO under at least moderately stringent hybridization conditions or which would hybridize thereto under at least moderately stringent conditions but for the use of synonymous codons.

By the term "substantially identical" it is meant that two amino acid sequences preferably are at least 70% identical, and more preferably are at least 85% identical and most preferably at least 95% identical, for example 96%, 97%, 98% or 99% identical. In order to determine the percentage of identity between two amino acid sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Mol. Biol., 1990: 215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50)

nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "functional variant", as used herein in reference to polynucleotides or polypeptides, refers to polynucleotides or polypeptides capable of performing the same function as a noted reference polynucleotide or polypeptide. Thus, for example, a functional variant of the polypeptide set forth in SEQ. ID NO: 2, refers to a polypeptide capable of performing the same function as the polypeptide set forth in SEQ. ID NO: 2. Functional variants include modified a polypeptide wherein, relative to a noted reference polypeptide, the modification includes a substitution, deletion or addition of one or more amino acids. In some embodiments, substitutions are those that result in a replacement of one amino acid with an amino acid having similar characteristics. Such substitutions include, without limitation (i) glutamic acid and aspartic acid; (i) alanine, serine, and threonine; (iii) isoleucine, leucine and valine, (iv) asparagine and glutamine, and (v) tryptophan, tyrosine and phenylalanine. Functional variants further include polypeptides having retained or exhibiting an enhanced alkaloid biosynthetic bioactivity.

The term "chimeric", as used herein in the context of polynucleotides, refers to at least two linked polynucleotides which are not naturally linked. Chimeric polynucleotides include linked polynucleotides of different natural origins. For example, a polynucleotide constituting a microbial promoter linked to a polynucleotide encoding a plant polypeptide is considered chimeric. Chimeric polynucleotides also may comprise polynucleotides of the same natural origin, provided they are not naturally linked. For example a polynucleotide constituting a promoter obtained from a particular cell-type may be linked to a polynucleotide encoding a polypeptide obtained from that same cell-type, but not normally linked to the polynucleotide constituting the promoter. Chimeric polynucleotides also include polynucleotides comprising any naturally occurring polynucleotides linked to any non-naturally occurring polynucleotides.

The term "in vivo", as used herein to describe methods of making morphinan compounds, refers to contacting a first morphinan compound with a polypeptide capable of mediating conversion of a first morphinan compound within a cell, including, for example, a microbial cell or a plant cell, to form a second morphinan compound.

The term "in vitro" as used herein to describe methods of making morphinan compounds refers to contacting a first morphinan with a polypeptide capable of mediating a conversion of the first morphinan in an environment outside a cell, including, without limitation, for example, in a microwell plate, a tube, a flask, a beaker, a tank, a reactor and the like, to form a second morphinan.

The terms "substantially pure" and "isolated", as may be used interchangeably herein describe a compound, e.g., an alkaloid, polynucleotide or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "recovered" as used herein in association with an enzyme or protein or morphinan, refers to a more or less pure form of the enzyme or protein or morphinan.

General Implementation

As hereinbefore mentioned, the present disclosure relates to alkaloids. The current disclosure further relates to certain polynucleotides and polypeptides. The herein provided methods and compositions are useful in that they facilitate a novel and efficient means of making certain alkaloids, notably certain morphinan alkaloids, including codeinone, codeine, morphine and morphinone. The methods and compositions can avoid the synthesis of certain side products, notably neopine and neomorphine, which in the methods known to the art can be produced at the expense of desired products, such as the aforementioned codeinone, codeine, morphine and morphinone. The current disclosure further provides cells and organisms not normally capable of synthesizing these morphinan alkaloid compounds. Such cells and organisms may be used as a source whence these morphinan alkaloids can economically be extracted. The morphinan alkaloids produced in accordance with the present disclosure are useful inter alia in the manufacture of pharmaceutical compositions.

Accordingly, the present disclosure provides, in at least one aspect, and in at least one embodiment, a method of making a second morphinan compound having a saturated carbon bond at position $C_8$-$C_{14}$ and a mono-unsaturated carbon bond at position $C_7$-$C_8$, the method comprising:
  (i) providing a first morphinan compound having a mono-unsaturated carbon bond at position $C_8$-$C_{14}$ and a saturated carbon bond at position $C_7$-$C_8$; and
  (ii) contacting the first morphinan compound with neopinone isomerase (NISO) under reaction conditions permitting the conversion of the first morphinan compound into the second morphinan compound.

In preferred embodiments, the first morphinan and the second morphinan each possess a bridging oxygen atom between carbon atoms $C_4$ and $C_5$ forming a tetrahydrofuranyl ring within the morphinan chemical structure, thus having the prototype chemical structure shown in FIG. 1B.

In at least one aspect, the present disclosure provides, in an embodiment, a method of making a second morphinan compound, the method comprising:

(a) providing a first morphinan compound; and
(b) contacting the first morphinan compound with a neopinone isomerase under conditions permitting the conversion of the first morphinan into the second morphinan;

wherein the first morphinan is a chemical compound having the chemical structure (I):

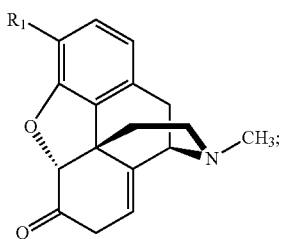

(I)

and
the second morphinan is a chemical compound having the chemical structure (II):

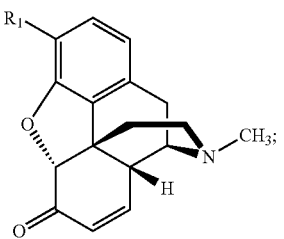

(II)

wherein $R_1$ is either a hydroxyl group, or a methoxy group.

In what follows, various example embodiments are provided to make morphinan alkaloids, including codeinone, morphinone, codeine and morphine. The alkaloid compounds that may be used and made, and the methods are further illustrated with reference to FIG. 4.

Synthesis of Codeinone

Figure 4:
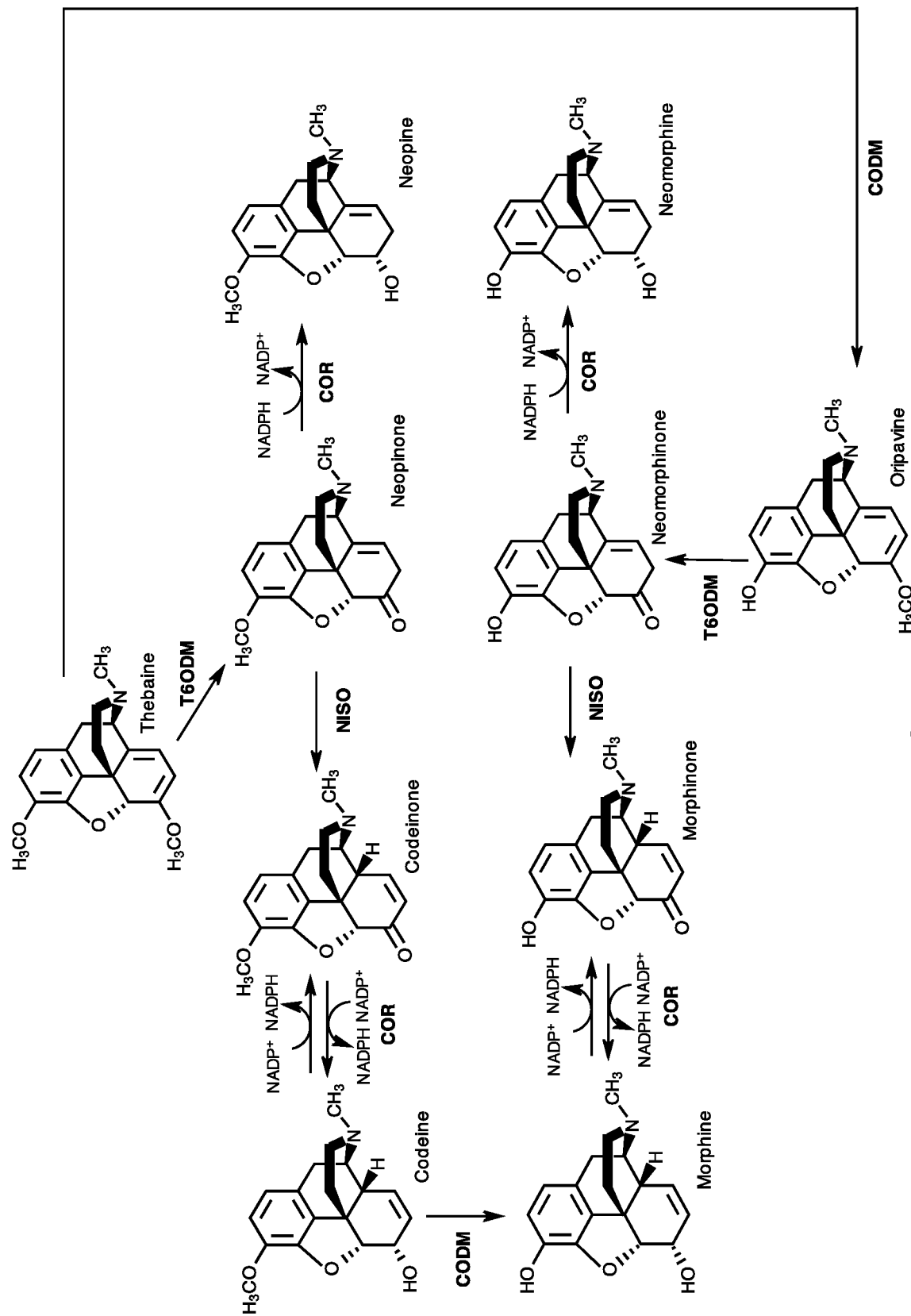
FIG. 4 depicts certain chemical example reactions involving the conversion of various alkaloid morphinan compounds to other alkaloid morphinan compounds.

As shown in FIG. 4, in one embodiment, in the first and second morphinan compound, $R_1$ is a methoxy group, and the method comprises:

(a) providing a first morphinan compound;
(b) contacting the first morphinan compound with a neopinone isomerase under conditions permitting the conversion of the first morphinan compound into the second morphinan;

wherein the first morphinan compound is a chemical compound having the chemical structure (IX):

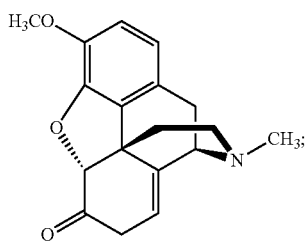

(IX)

and
the second morphinan compound is a chemical compound having the chemical structure (X):

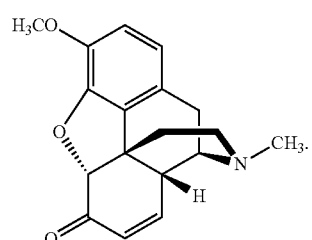

(X)

It is noted that compound (IX) and (X) are known as neopinone and codeinone, respectively.

Synthesis of Morphinone

As shown in FIG. 4, in one embodiment, in the first and second morphinan compound, $R_1$ is a hydroxyl group, and the method comprises:

(a) providing a first morphinan compound;
(b) contacting the first morphinan compound with a neopinone isomerase under conditions permitting the conversion of the first morphinan compound into the second morphinan compound;

wherein the first morphinan compound is a chemical compound having the chemical structure (XI):

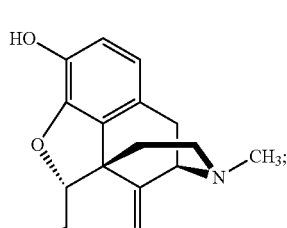

(XI)

and
the second morphinan is a chemical compound having the chemical structure (XII):

(XII)

It is noted that compound (XI) and (XII) are known as neomorphinone and morphinone, respectively.

Synthesis of Codeine

As shown in FIG. 4, in one embodiment, in the first and second morphinan compound, $R_1$ is a methoxy group, and the method comprises:

(a) providing a first morphinan compound;
(b) contacting the first morphinan compound with a neopinone isomerase under conditions permitting the conversion of the first morphinan compound into the second morphinan;
wherein the first morphinan compound is a chemical compound having the chemical structure (IX):

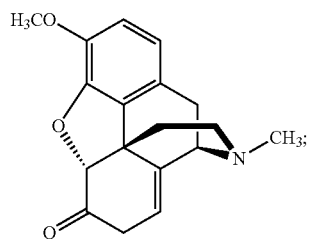
(IX)

and
the second morphinan compound is a chemical compound having the chemical structure (X):

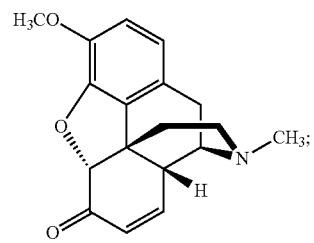
(X)

and
the method further comprising contacting the second morphinan compound with codeinone reductase under reaction conditions permitting the second morphinan compound into a third morphinan compound, wherein the third morphinan compound has the chemical structure (III):

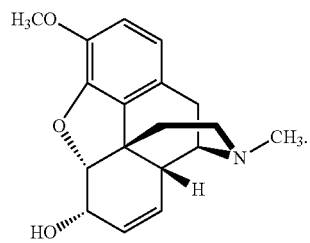
(III)

It is noted that compound (IX), (X) and (III) are known as neopinone, codeinone and codeine, respectively.

In some embodiments, a reaction mixture can be prepared to include the first morphinan compound and both neopinone isomerase and codeinone reductase.

In some embodiments, a reaction mixture can be prepared to include the first morphinan compound and neopinone isomerase, and only upon completion of the reaction, codeinone reductase can be added to the reaction mixture.

In some embodiments, certain quantities of the second morphinan compound may in the presence of codeinone reductase be converted into a fourth morphinan compound, the fourth morphinan having the chemical structure (IV):

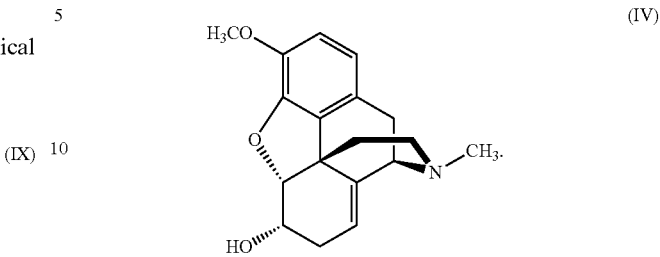
(IV)

It is noted that compound (IV) is known as neopine.

In general upon completion of the reaction, the reaction mixture constitutes no more than about 20% (w/w) of compound (IV) of all morphinan compounds.

In some embodiments, compound (IV) upon completion of the reaction constitute no more than about 15%, 14%, 13%, 12%, 11%, 10%, 9%, 8%, 7%, 6%, 5%, 4%, 3%, 2% of 1% (w/w) of all morphinan compounds.

Synthesis of Morphine

As shown in FIG. 4, in one embodiment, in the first and second morphinan compound, $R_1$ is a hydroxyl group, and the method comprises:

(a) providing a first morphinan compound;
(b) contacting the first morphinan compound with a neopinone isomerase under conditions permitting the conversion of the first morphinan compound into the second morphinan compound;
wherein the first morphinan compound is a chemical compound having the chemical structure (XII):

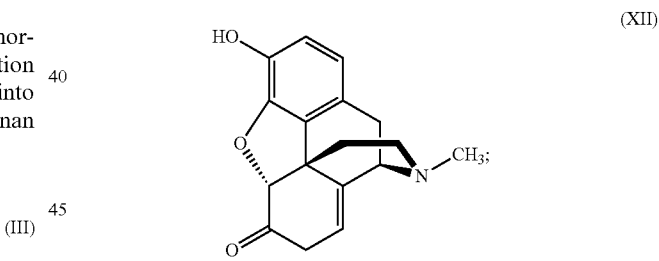
(XII)

and
the second morphinan compound is a chemical compound having the chemical structure (XIII):

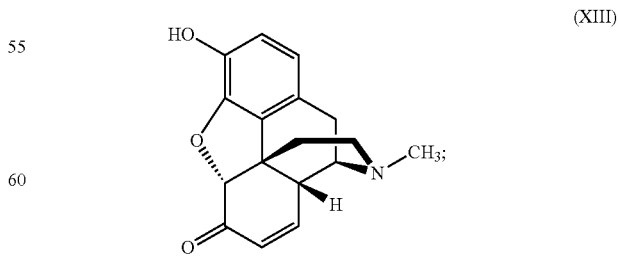
(XIII)

and
the method further comprising contacting the second morphinan compound with codeinone reductase under reaction conditions permitting the conversion of the second morphinan compound into a third morphinan, wherein the third morphinan has the chemical structure (V):

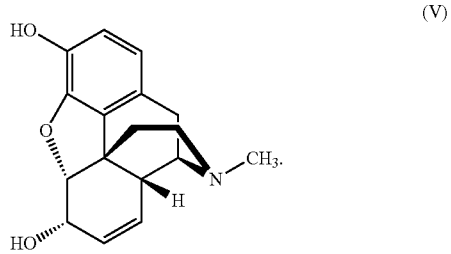

(V)

It is noted that compound (XII), (XIII) and (V) are known as neomorphinone, morphinone and morphine, respectively.

As shown in FIG. 4, in one embodiment, in the first and second morphinan compound, $R_1$ is a hydroxyl group, and the method comprises:

(a) providing a first morphinan compound;
(b) contacting the first morphinan compound with a neopinone isomerase under conditions permitting the conversion of the first morphinan compound into the second morphinan compound;

wherein the first morphinan compound is a chemical compound having the chemical structure (XII):

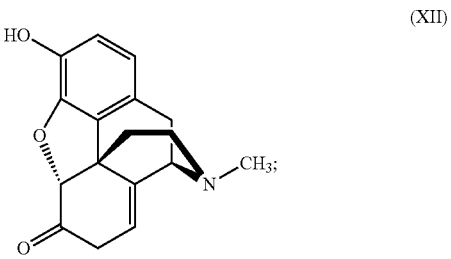

(XII)

and the second morphinan compound is a chemical compound having the chemical structure (XIII):

(XIII)

and the method further comprising contacting the second morphinan compound with codeinone reductase under reaction conditions permitting the second morphinan compound into a third morphinan, wherein the third morphinan compound has the chemical structure (V):

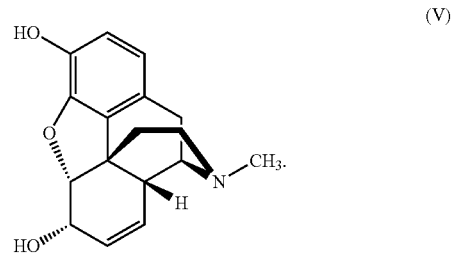

(V)

It is noted that compound (XII), (XIII) and (V) are known as neomorphinone, morphinone and morphine, respectively.

In some embodiments, a reaction mixture can be prepared to include the first morphinan compound and both neopinone isomerase and codeinone reductase.

In some embodiments a reaction mixture can be prepared to include the first morphinan compound and neopinone isomerase, and only upon completion of the reaction, codeinone reductase can be added to the reaction mixture.

In some embodiments, certain quantities of the second morphinan may in the presence of codeinone reductase be converted into a fourth morphinan, the fourth morphinan having the chemical structure (VI):

(VI)

It is noted that compound (VI) is also known as neomorphine.

In general upon completion of the reaction, the reaction mixture constitutes no more than about 20% (w/w) of compound (VI) of all morphinan compounds.

In some embodiments, compound (VI) upon completion of the reaction constitutes no more than about 15%, 14%, 13%, 12%, 11%, 10%, 9%, 8%, 7%, 6%, 5%, 4%, 3%, 2% of 1% (w/w) of all morphinan compounds.

As further shown in FIG. 4, in one embodiment, in the first and second morphinan compound, $R_1$ is a methoxy group, and the method comprises:

(a) providing a first morphinan compound;
(b) contacting the first morphinan compound with a neopinone isomerase under conditions permitting the conversion of the first morphinan compound into the second morphinan compound;

wherein the first morphinan compound is a chemical compound having the chemical structure (IX):

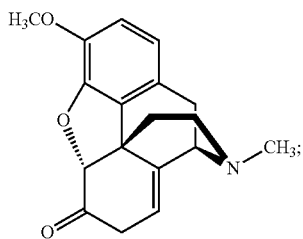

(IX)

and
the second morphinan compound is a chemical compound having the chemical structure (X):

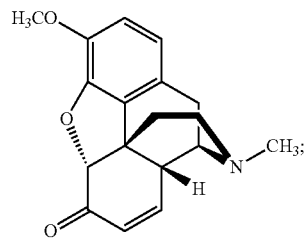

(X)

the method further comprising contacting the second morphinan compound with codeinone reductase under reaction conditions permitting the second morphinan compound into a third morphinan compound wherein the third morphinan compound has the chemical structure (III):

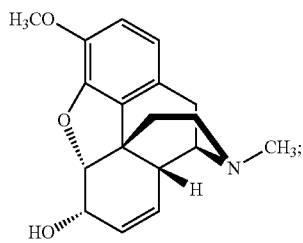

(III)

and
the method further comprising contacting the third morphinan compound with codeine-O-demethylase under reaction conditions permitting the conversion of the third morphinan compound into a fourth morphinan compound, wherein the fourth morphinan compound has the chemical structure (V):

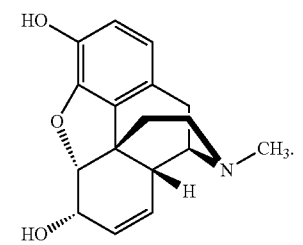

(V)

It is noted that compound (IX), (X), (III) and (V) are known as neopinone, codeinone, codeine and morphine, respectively.

In some embodiments, a reaction mixture can be prepared to include the first morphinan compound and each neopinone isomerase, codeinone reductase and codeine-O-demethylase.

In some embodiments, a reaction mixture can be prepared to include the first morphinan compound and neopinone isomerase, and only upon completion of the reaction, codeinone reductase and codeinone-O-demethylase can be added to the reaction mixture, either together or sequentially.

In some embodiments, the reaction mixture can include 2-oxoglutarate to facilitate the demethylation reaction catalyzed by codeine-O-demethylase.

Synthesis of 14-Hydroxymorphinone and Oxymorphone

Figure 5:
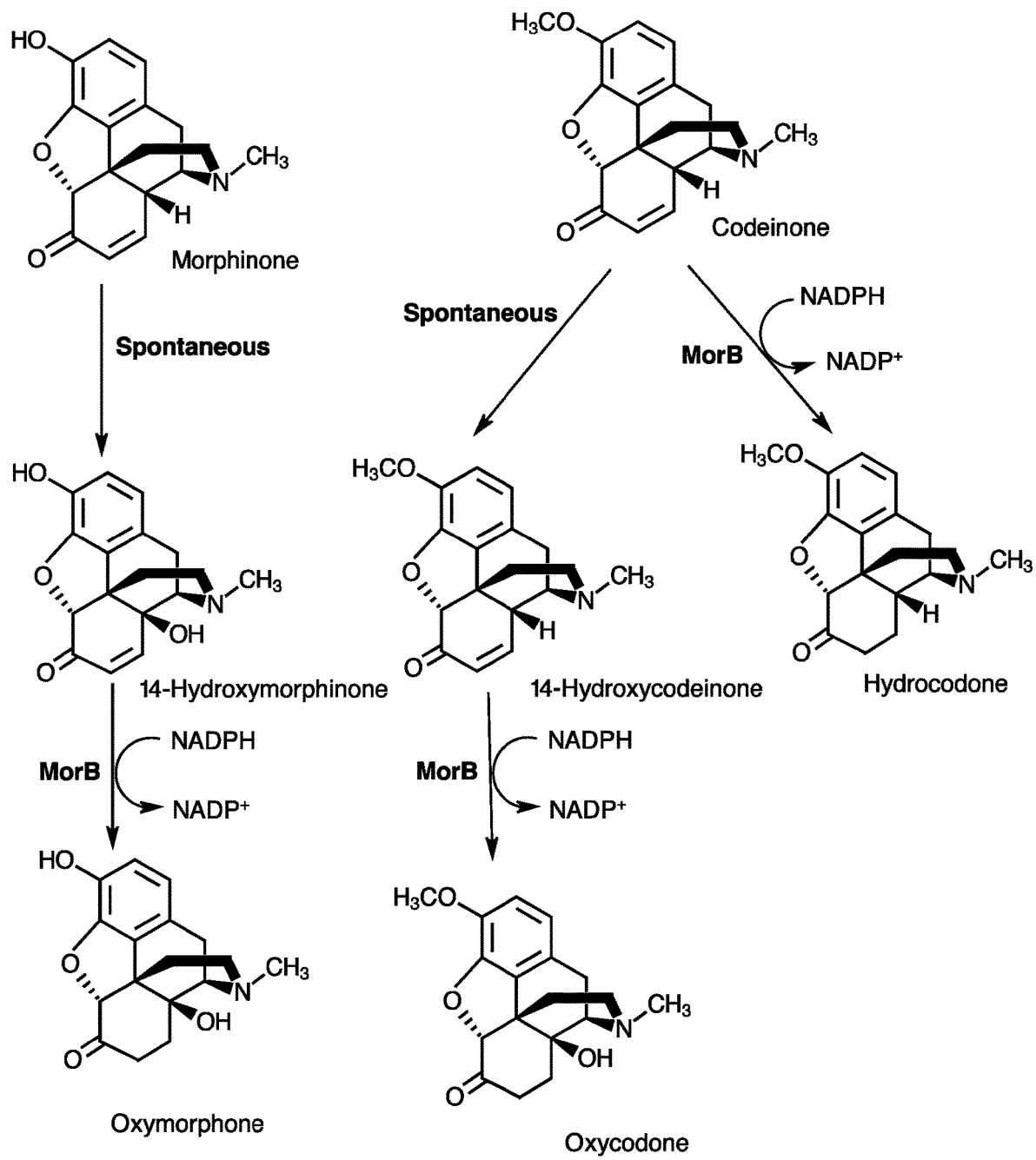
FIG. 5 depicts certain other chemical example reactions involving the conversion of various alkaloid morphinan compounds to other alkaloid morphinan compounds.

As shown in FIG. 4 and FIG. 5, in one embodiment, in the first and second morphinan compound, $R_1$ is a hydroxyl group, and the method comprises:
(a) providing a first morphinan compound;
(b) contacting the first morphinan compound with a neopinone isomerase under conditions permitting the conversion of the first morphinan compound into the second morphinan compound;
wherein the first morphinan compound is a chemical compound having the chemical structure (XII):

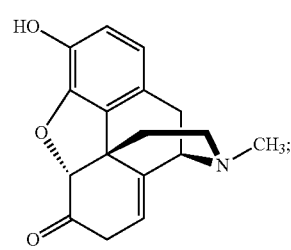

(XII)

and
the second morphinan compound is a chemical compound having the chemical structure (XIII):

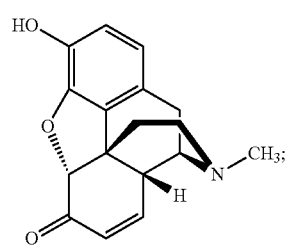

(XIII)

and
the method further comprising contacting the second morphinan compound with morphinone reductase B under reaction conditions permitting the second morphinan compound into a third morphinan compound, wherein the third morphinan compound has the chemical structure (XVII):

(XVII)

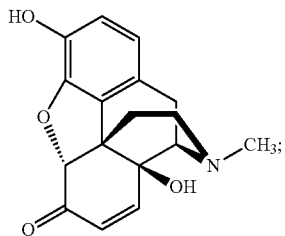

or
wherein the third morphinan has the chemical structure (XVIII):

(XVIII)

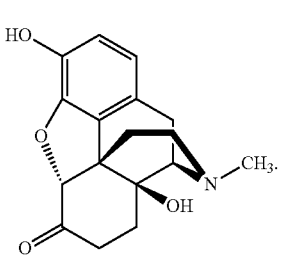

In some embodiments a mixture of compound (XVII) and (XVIII) is formed. It is noted that compound (XII), (XIII), (VII) and (XVIII) are known as neomorphinone, morphinone, 14-hydroxymorphinone and oxymorphone, respectively.

In some embodiments, a reaction mixture can be prepared to include the first morphinan compound and both neopinone isomerase and morphinone reductase B.

In some embodiments a reaction mixture can be prepared to include the first morphinan compound and neopinone isomerase, and only upon completion of the reaction, morphinone reductase B can be added to the reaction mixture.

In some embodiments, certain quantities of the second morphinan may in the presence of codeinone reductase be converted into a fourth morphinan, the fourth morphinan having the chemical structure (VI):

(VI)

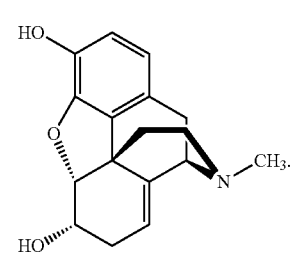

It is noted that compound (VI) is also known as neomorphine.

In general upon completion of the reaction, the reaction mixture constitutes no more than about 20% (w/w) of compound (VI) of all morphinan compounds.

In some embodiments, compound (VI) upon completion of the reaction constitute no more than about 15%, 14%, 13%, 12%, 11%, 10%, 9%, 8%, 7%, 6%, 5%, 4%, 3%, 2% of 1% (w/w) of all morphinan compounds.

Synthesis of 14-Hydroxycodeinone, Oxycodone and Hydrocodone

As shown in FIG. 4 and FIG. 5, in one embodiment, in the first and second morphinan compound, $R_1$ is a methoxy group, and the method comprises:

(c) (a) providing a first morphinan compound;

(d) (b) contacting the first morphinan compound with a neopinone isomerase under conditions permitting the conversion of the first morphinan compound into the second morphinan;

wherein the first morphinan compound is a chemical compound having the chemical structure (IX):

(IX)

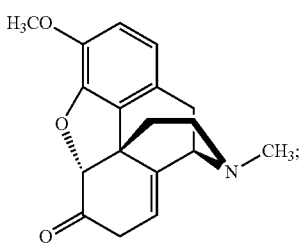

and the second morphinan compound is a chemical compound having the chemical structure (X):

(X)

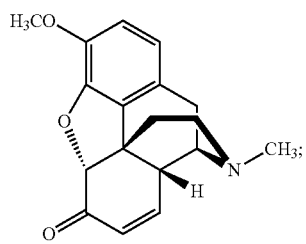

and the method further comprising contacting the second morphinan compound with morphinone reductase B under reaction conditions permitting the second morphinan compound into a third morphinan compound, wherein the third morphinan compound has the chemical structure: (XIV):

(XIV)

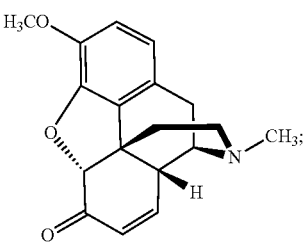

or wherein the third morphinan compound has the chemical structure (XV):

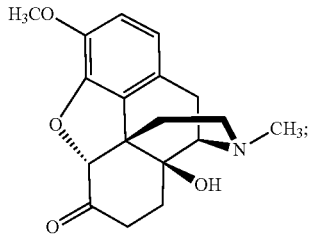

(XV)

and
or wherein the third morphinan compound has the chemical structure (XVI):

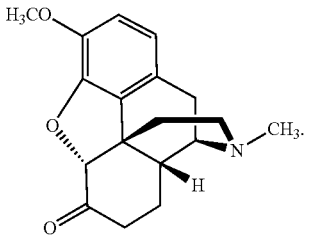

(XVI)

In some embodiments, a mixture comprising two or more of compounds (XIV), (XV) and (XVI) are formed. It is noted that compound (IX), (X), (XIV), (XV) and (XVI) are known as neopinone, codeinone, 14-hydroxycodeinone, oxycodone and hydrocodone, respectively.

In some embodiments, a reaction mixture can be prepared to include the first morphinan compound and both neopinone isomerase and morphinone reductase B.

In some embodiments, a reaction mixture can be prepared to include the first morphinan compound and neopinone isomerase, and only upon completion of the reaction, morphinone reductase B can be added to the reaction mixture.

In some embodiments, certain quantities of the second morphinan compound may in the presence of codeinone reductase be converted into a fourth morphinan compound, the fourth morphinan having the chemical structure (IV):

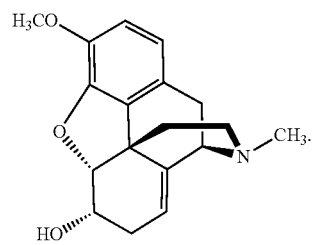

(IV)

It is noted that compound (IV) is known as neopine.

In general, upon completion of the reaction, the reaction mixture constitutes no more than about 20% (w/w) of compound (IV) of all morphinan compounds.

In some embodiments, compound (IV) upon completion of the reaction constitute no more than about 15%, 14%, 13%, 12%, 11%, 10%, 9%, 8%, 7%, 6%, 5%, 4%, 3%, 2% of 1% (w/w) of all morphinan compounds.

In Vitro Synthesis

In accordance with certain aspects of the present disclosure, a first morphinan compound is brought in contact with a neopinone isomerase, generally in catalytic quantities, under reaction conditions permitting an enzyme catalyzed chemical conversion of the first morphinan compound to form a second morphinan compound under in vitro reaction conditions. Under such in vitro reaction conditions, the initial reaction constituents can be provided in more or less pure form and can contacted with each other and mixed under conditions that permit the requisite chemical reactions, upon enzyme catalysis, to substantially proceed. Substantially pure forms of the first morphinan compound can be chemically synthesized, or isolated from natural sources, including from poppy plants, including *Papaver somniferum*. Other plant species that may be used in accordance herewith to obtain an alkaloid substrate include, without limitation, plant species belonging to the plant families of Eupteleaceae, Lardizabalaceae, Circaeasteraceae, Menispermaceae, Berberidaceae, Ranunculaceae, and Papaveraceae (including those belonging to the subfamilies of Pteridophylloideae, Papaveroideae and Fumarioideae), and further include plants belonging to the genus *Argemone*, including *Argemone mexicana* (Mexican Prickly Poppy), plants belonging to the genus *Berberis*, including *Berberis thunbergii* (Japanese Barberry), plants belonging to the genus *Chelidonium*, including *Chelidonium majus* (Greater Celandine), plants belonging to the genus *Cissampelos*, including *Cissampelos mucronata* (Abuta), plants belonging to the genus *Cocculus*, including *Cocculus trilobus* (Korean Moonseed), plants belonging to the genus *Corydalis*, including *Corydalis chelanthifolia* (Ferny Fumewort), *Corydalis cava; Corydalis ochotenis; Corydalis ophiocarpa; Corydalis platycarpa; Corydalis tuberosa*; and *Cordyalis bulbosa*, plants belonging to the genus *Eschscholzia*, including *Eschscholzia californica* (California Poppy), plants belonging to the genus *Glaucium*, including *Glaucium flavum* (Yellowhorn Poppy), plants belonging to the genus *Hydrastis*, including *Hydrastis canadensis* (Goldenseal), plants belonging to the genus *Jeffersonia*, including *Jeffersonia diphylla* (Rheumatism Root), plants belonging to the genus *Mahonia*, including *Mahonia aquifolium* (Oregon Grape), plants belonging to the genus *Menispermum*, including *Menispermum canadense* (Canadian Moonseed), plants belonging to the genus *Nandina*, including *Nandina domestica* (Sacred Bamboo), plants belonging to the genus *Nigella*, including *Nigella sativa* (Black Cumin), plants belonging to the genus *Papaver*, including *Papaver bracteatum* (Persian Poppy), *Papaver somniferum, Papaver cylindricum, Papaver decaisnei, Papaverfugax, Papaver nudicale, Papaver oreophyllum, Papaver orientale, Papaver paeonifolium, Papaver persicum, Papaver pseudo-orientale, Papaver rhoeas, Papaver rhopalothece, Papaver armeniacum, Papaver setigerum, Papaver tauricolum*, and *Papaver triniaefolium*, plants belonging to the genus *Sanguinaria*, including *Sanguinaria canadensis* (Bloodroot), plants belonging to the genus *Stylophorum*, including *Stylophorum diphyllum* (Celandine Poppy), plants belonging to the genus *Thalictrum*, including *Thalictrum flavum* (Meadow Rue), plants belonging to the genus *Tinospora*, including *Tinospora cordifolia* (Heartleaf Moonseed), plants belonging to the genus *Xanthoriza*, including *Xanthoriza simplicissima* (Yellowroot) and plants belonging to the genus *Romeria* including *Romeria carica*.

Referring again to FIG. 4, in some embodiments, the first morphinan compound can be formed in a reaction comprising providing a precursor morphinan compound and converting the precursor morphinan compound to form the first morphinan.

In some embodiments, the precursor compound can be a compound having the chemical structure (VII):

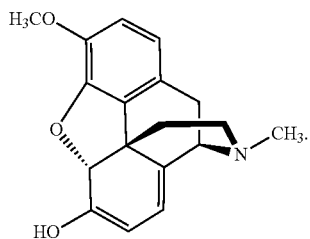

(VII)

In some embodiments, the precursor compound can be a compound having chemical structure (VII) and the precursor compound is reacted in the presence of T6-O-demethylase to form the first morphinan compound, wherein in the first morphinan compound, $R_1$ is a methoxy group. The foregoing reaction can be performed in-vivo or in-vitro.

In some embodiments, the precursor compound can be a compound having chemical structure (VIII):

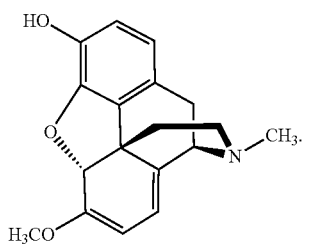

(VIII)

and the precursor compound is reacted in the presence of T6-O-demethylase, to form the first morphinan compound, wherein in the first morphinan compound, $R_1$ is a hydroxyl group.

In some embodiments, the precursor compound can be a compound having chemical structure (VII) and the precursor compound is reacted in the presence of codeine-O-demethylase to form a further precursor compound having the chemical structure (VIII), and the further precursor compound is reacted in the presence of T6-O-demethylase, to form the first morphinan compound, wherein in the first morphinan compound, $R_1$ is a hydroxyl group. The foregoing reactions can be performed in-vivo or in-vitro.

In accordance herewith, more or less pure forms of a neopinone isomerase enzyme may be isolated from natural sources, including microbial species, and any of the hereinbefore mentioned plant species, or the enzyme may be prepared recombinantly. Thus provided in here further is a method of making, neopinone isomerase, the method comprising:

(a) providing a chimeric nucleic acid sequence comprising as operably linked components:
  (i) a nucleic acid sequence encoding a neopinone isomerase; and
  (ii) one or more nucleic acid sequences capable of controlling expression in a host cell;
(b) introducing the chimeric nucleic acid sequence into a host cell and growing the host cell to produce the neopinone isomerase; and
(c) recovering the neopinone isomerase from the host cell.

In some embodiments, the neopinone isomerase is an enzyme encoded by a nucleic acid sequence comprising one or more nucleic acid sequences selected from the group consisting of:

(i) SEQ. ID NO: 14, SEQ. ID NO: 15, SEQ. ID NO: 16 and SEQ. ID NO: 17;

(ii) a nucleic acid sequence that is substantially identical to SEQ. ID NO: 14, SEQ. ID NO: 15, SEQ. ID NO: 16 or SEQ. ID NO: 17;

(iii) a nucleic acid sequence that is substantially identical to SEQ. ID NO: 14, SEQ. ID NO: 15, SEQ. ID NO: 16 or SEQ. ID NO: 17 but for the degeneration of the genetic code;

(iv) a nucleic acid sequence that is complementary to SEQ. ID NO: 14, SEQ. ID NO: 15, SEQ. ID NO: 16 or SEQ. ID NO: 17;

(v) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;

(vi) a nucleic acid sequence that encodes a functional variant of a polypeptide comprising one or more of the amino acid sequences set forth in in SEQ. ID NO: 18, SEQ. ID NO: 19, SEQ. ID NO: 20 or SEQ. ID NO: 21; and (vii) a nucleic acid sequence that hybridizes under stringent conditions to any one of the nucleic acid sequences set forth in (i), (ii), (iii), (iv), (v) or (vi).

In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the neopine isomerase can be a polypeptide encoded by a nucleic acid sequence selected from SEQ. ID NO: 1, SEQ. ID NO: 9, SEQ. ID NO: 12 and SEQ. ID NO: 53

In some embodiments, the polypeptide comprising one or more of the amino acid sequences set forth in SEQ. ID NO: 18, SEQ. ID NO: 19, SEQ. ID NO: 20 or SEQ. ID NO: 21 is selected from SEQ. ID NO: 2 and SEQ. ID NO: 54.

In some embodiments, two or more, or three or more nucleic acid sequences from the group consisting of SEQ. ID NO: 14, SEQ. ID NO: 15, SEQ. ID NO: 16 or SEQ. ID NO: 17 are selected.

Growth of the host cells leads to production of the neopinone isomerase. The neopinone isomerase polypeptide subsequently can be recovered, isolated and separated from other host cell components by a variety of different protein purification techniques including, e.g. ion-exchange chromatography, size exclusion chromatography, affinity chromatography, hydrophobic interaction chromatography, reverse phase chromatography, gel filtration, etc. Further general guidance with respect to protein purification may for example be found in: Cutler, P. Protein Purification Protocols, Humana Press, 2004, Second Ed. Thus substantially pure preparations of the neopinone isomerase polypeptides may be obtained.

In accordance herewith, a first morphinan compound is brought in contact with neopinone isomerase under reaction conditions permitting an enzyme catalyzed chemical conversion of the first morphinan compound to form the second morphinan compound.

In some embodiments, the agents are brought in contact with each other and mixed to form a mixture. In some embodiments, the mixture is an aqueous mixture comprising water and further optionally additional agents to facilitate enzyme catalysis, including buffering agents, salts, pH modifying agents, cofactors, or other enzymes, including, in certain embodiments, as herein described, codeinone reductase or codeine-O-demethylase, or as also herein described, in certain embodiments. Reactions may be performed at a range of different temperatures. In preferred embodiments, a reaction is performed at a temperature between about 18° C. and 60° C., or between about 37° C. and 55° C., or at around 50° C.

Reactions further may be conducted at different pH's, for example, in certain embodiments at a pH between 7 and 9. The pH may be controlled by the addition of buffering agents to the reaction mixtures. In embodiments, in which a reaction mixture includes both neopinone isomerase and codeinone reductase, a pH between about 5.0 and 9.0, and more preferably about 7.5. It is noted that in reactions involving both neopinone isomerase and codeinone reductase the operable pH range may differ from the operable pH range of reactions involving the use codeinone reductase alone, for example, in some embodiments the operable pH range may be greater in reactions involving both neopinone isomerase and codeinone reductase, ranging from about 5.0 to about 9.0.

In embodiments hereof, wherein a reaction mixture includes the enzyme codeinone reductase, the reaction mixture preferably further includes the cofactor nicotineamide adenine dinucleotide phosphate (NADP$^+$). In the performance of the reaction NADP$^+$ can be converted to NADPH. It is noted that the NADPH formed can be used as a cofactor in reactions involving neopinone or neomorphinone to form neopine and neomorphine, respectively.

In embodiments hereof, wherein a reaction mixture includes both codeinone reductase and neopinone isomerase, in preferred embodiments, the quantities of neopinone isomerase included in the reaction mixture exceed the quantities of codeinone reductase. Thus, for example, the quantities of neopinone isomerase may exceed the quantities of codeinone reductase by a factor of at least about 5×, 10×, 15×, 20× or 25× on a weight basis. In preferred embodiments, the quantities of neopinone isomerase, exceed the quantities of codeine reductase by a factor of about 17×, 18×, 19×, 20×, 21×, 22× or 23× on a weight basis. At these quantities, the formation of neopine and neomorphine at the expense of codeinone and morphinone, respectively, can be significantly reduced, in particular, when compared to reaction mixtures not including neopinone isomerase. In preferred embodiments, upon completion of the reaction, neopine or neomorphine constitute no more than about 20% (w/w) of all morphinan compounds present in the reaction mixture. In further preferred embodiments, neopine or neomorphine constitute no more than about 15%, 14%, 13%, 12%, 11%, 10%, 9%, 8%, 7%, 6%, 5%, 4%, 3%, 2% of 1% (w/w) of all morphinan compounds present in the reaction mixture.

Upon completion of the in vitro reaction the second morphinan compound, or morphinan compounds derived therefrom, including codeine and morphine, may be obtained in more or less pure form.

In Vivo Synthesis

In accordance with certain aspects of the present disclosure, a first morphinan compound is brought in contact with a neopinone isomerase enzyme, generally in catalytic quantities, under reaction conditions permitting an enzyme catalyzed chemical conversion of the first morphinan compound to form a second morphinan compound under in vivo reaction conditions. Under such in vivo reaction conditions, living cells are modified in such a manner that they produce the second morphinan. In certain embodiments, the living cells can be microorganisms, including bacterial cells, including *Escherichia coli* cells, for example and fungal cells, including, yeast cells, *Saccharomyces cerevisiae* cells and *Yarrowia lipolytica* cells, for example. In other embodiments, the living cells are multicellular organisms, including plants.

In some embodiments, the living cells can be selected to be host cells capable of producing the first morphinan compound, but not the second morphinan compound. In some embodiments, the living cells can be selected to be host cells capable of producing a first morphinan compound having formula (I), but not second morphinan compound having formula (II). Such cells include, without limitation, bacteria, yeast, other fungal cells, plant cells, or animal cells. Thus, by way of example only, a host cell can be a yeast host cell capable of producing a first morphinan having formula (I), but not a second morphinan having formula (II). In order to modulate such host cells in such a manner that they produce the second morphinan compound, a neopinone isomerase in accordance herewith can be heterologously introduced and expressed in the host cells.

In some embodiments, the living cells naturally produce the second morphinan compound, however the living cells are modulated in such a manner that the levels of the second morphinan compound produced by the cell are modulated, relative to the levels produced by the cell without heterologous introduction of the neopinone isomerase in such living cells.

In order to produce the second morphinan compound, provided herein is further a method for preparing a second morphinan compound comprising:

(A) providing a chimeric nucleic acid sequence comprising as operably linked components:
  (a) a nucleic acid sequence encoding a neopinone isomerase polypeptide comprising a polypeptide sequence encoded by a polynucleotide having a nucleic acid sequence comprising one or more nucleic acid sequences selected from the group consisting of:
    (i) SEQ. ID NO: 14, SEQ. ID NO: 15, SEQ. ID NO: 16 and SEQ. ID NO: 17;
    (ii) a nucleic acid sequence that is substantially identical to SEQ. ID NO: 14, SEQ. ID NO: 15, SEQ. ID NO: 16 or SEQ. ID NO: 17;
    (iii) a nucleic acid sequence that is substantially identical to SEQ. ID NO: 14, SEQ. ID NO: 15, SEQ. ID NO: 16 or SEQ. ID NO: 17 but for the degeneration of the genetic code;
    (iv) a nucleic acid sequence that is complementary to SEQ. ID NO: 14, SEQ. ID NO: 15, SEQ. ID NO: 16 or SEQ. ID NO: 17;
    (v) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;
(vi) a nucleic acid sequence that encodes a functional variant of a polypeptide comprising one or more of the amino acid sequences set forth in in SEQ. ID NO: 18, SEQ. ID NO: 19, SEQ. ID NO: 20 or SEQ. ID NO: 21; and
(vii) a nucleic acid sequence that hybridizes under stringent conditions to any one of the nucleic acid sequences set forth in (i), (ii), (iii), (iv), (v) or (vi); and
(b) one or more nucleic acid sequences capable of controlling expression in a host cell;
(B) introducing the chimeric nucleic acid sequence into a host cell capable of producing a first morphinan having the chemical structure (I):

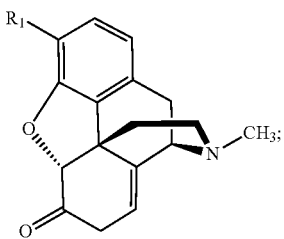

(I)

and
(C) growing the cell to produce a second morphinan having the chemical structure (II):

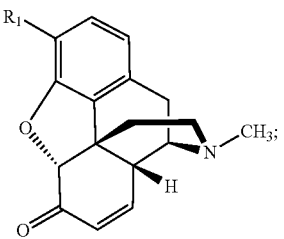

(II)

wherein $R_1$ is either a hydroxyl group, or a methoxy group.

In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the neopine isomerase can be a polypeptide encoded by a nucleic acid sequence selected from SEQ. ID NO: 1, SEQ. ID NO: 9, SEQ. ID NO: 12 and SEQ. ID NO: 53

In some embodiments, the polypeptide comprising one or more of the amino acid sequences set forth in SEQ. ID NO: 18, SEQ. ID NO: 19, SEQ. ID NO: 20 or SEQ. ID NO: 21 is selected from SEQ. ID NO: 2 and SEQ. ID NO: 54.

In some embodiments, two, three or four nucleic acid sequences from the group consisting of SEQ. ID NO: 14, SEQ. ID NO: 15, SEQ. ID NO: 16 or SEQ. ID NO: 17 are selected.

In some embodiments, the sequences SEQ. ID NO: 14, SEQ. ID NO: 15, SEQ. ID NO: 16 and SEQ. ID NO: 17 are selected, and SEQ. ID NO: 14, SEQ. ID NO: 15, SEQ. ID NO: 16 or SEQ. ID NO: 17 are linked in a 5' to 3' direction in the order: SEQ. ID NO: 14, SEQ. ID NO: 15, SEQ. ID NO: 16, SEQ. ID NO: 17.

In some embodiments, the nucleic acid sequence further comprises an interspersing sequence between SEQ. ID NO: 14 and 15 no longer than 39 nucleic acid residues.

In some embodiments, the nucleic acid sequence further comprises an interspersing sequence between SEQ. ID NO: 15 and 16 no longer than 6 nucleic acid residues.

In some embodiments, the nucleic acid sequence further comprises an interspersing sequence between SEQ. ID NO: 16 and 17 no longer than 66 nucleic acid residues.

In some embodiments, the nucleic acid sequence further comprises an interspersing sequence between SEQ. ID NO: 14 and 15 comprising or consisting of a nucleic acid sequence encoding SEQ. ID NO: 59.

In some embodiments, the nucleic acid sequence further comprises an interspersing sequence between SEQ. ID NO: 14 and 15 comprising a nucleic acid sequence encoding an amino acid sequence substantially identical to SEQ. ID NO: 59.

In some embodiments, the nucleic acid sequence further comprises an interspersing sequence between SEQ. ID NO: 15 and 16 comprising or consisting of a nucleic acid sequence encoding SEQ. ID NO: 60.

In some embodiments, the nucleic acid sequence further comprises an interspersing sequence between SEQ. ID NO: 15 and 16 comprising a nucleic acid sequence encoding an amino acid sequence substantially identical to SEQ. ID NO: 60.

In some embodiments, the nucleic acid sequence further comprises an interspersing sequence between SEQ. ID NO: 16 and 17 comprising or consisting of a nucleic acid sequence encoding SEQ. ID NO: 61.

In some embodiments, the nucleic acid sequence further comprises an interspersing sequence between SEQ. ID NO: 16 and 17 comprising a nucleic acid encoding an amino acid sequence substantially identical to SEQ. ID NO: 61.

In some embodiments, the method can further include a step c) comprising isolating the second morphinan.

In some embodiments, the nucleic acid sequences can be isolated from any of the hereinbefore mentioned plant species. Thus the present disclosure further includes a substantially pure polynucleotide comprising a nucleic acid sequence comprising one or more nucleic acid sequences selected from the group consisting of:
(i) SEQ. ID NO: 14, SEQ. ID NO: 15, SEQ. ID NO: 16 and SEQ. ID NO: 17;
(ii) a nucleic acid sequence that is substantially identical to SEQ. ID NO: 14, SEQ. ID NO: 15, SEQ. ID NO: 16 or SEQ. ID NO: 17;
(iii) a nucleic acid sequence that is substantially identical to SEQ. ID NO: 14, SEQ. ID NO: 15, SEQ. ID NO: 16 or SEQ. ID NO: 17 but for the degeneration of the genetic code;
(iv) a nucleic acid sequence that is complementary to SEQ. ID NO: 14, SEQ. ID NO: 15, SEQ. ID NO: 16 or SEQ. ID NO: 17;
(v) a nucleic acid sequence encoding a polypeptide comprising one or more of the amino acid sequences set forth in SEQ. ID NO: 18, SEQ. ID NO: 19, SEQ. ID NO: 20 or SEQ. ID NO: 21;
(vi) a nucleic acid sequence that encodes a functional variant of a polypeptide comprising one or more of the amino acid sequences set forth in in SEQ. ID NO: 18, SEQ. ID NO: 19, SEQ. ID NO: 20 or SEQ. ID NO: 21; and (vii) a nucleic acid sequence that hybridizes under stringent conditions to any one of the nucleic acid sequences set forth in (i), (ii), (iii), (iv), (v) or (vi).

In some embodiments, the nucleic acid sequence that is substantially identical to SEQ. ID NO: 14, SEQ. ID NO: 15, SEQ. ID NO; 16 or SEQ. ID NO: 17 can be at least 90% identical, at least 91% identical, at least 92% identical, at least 93% identical, at least 94% identical, at least 95% identical, at least 96% identical, at least 97% identical, at least 98% identical or 100% identical to SEQ. ID NO: 14, SEQ. ID NO: 15, SEQ. ID NO; 16 or SEQ. ID NO: 17.

In some embodiments, the nucleic acid sequence encodes a neopine isomerase and is selected from SEQ. ID NO: 1, SEQ. ID NO: 9, SEQ. ID NO: 12 and SEQ. ID NO: 53

In some embodiments the polypeptide comprising one or more of the amino acid sequences set forth in SEQ. ID NO: 18, SEQ. ID NO: 19, SEQ. ID NO: 20 or SEQ. ID NO: 21 is selected from SEQ. ID NO: 2 and SEQ. ID NO: 54.

In accordance herewith, the nucleic acid sequence encoding neopinone isomerase can be linked to a nucleic acid sequence capable of controlling expression of neopinone isomerase in a host cell. The present disclosure also provides, a nucleic acid sequence encoding a neopinone isomerase linked to a promoter capable of controlling expression in a host cell. Accordingly, the present disclosure provides in one embodiment, a chimeric polynucleotide comprising a polynucleotide comprising a nucleic acid sequence comprising as operably linked components:

(a) a polynucleotide comprising a nucleic acid sequence encoding a neopinone isomerase; and (b) a polynucleotide comprising a nucleic acid sequence capable of controlling expression of neopinone isomerase in a host cell.

Nucleic acid sequences capable of controlling expression in host cells that may be used herein include any transcriptional promoter capable of controlling expression of polypeptides in host cells. Generally, promoters obtained from bacterial cells are used when a bacterial host is selected in accordance herewith, while a fungal promoter will be used when a fungal host is selected, a plant promoter will be used when a plant cell is selected, and so on. Further nucleic acid elements capable of controlling expression in a host cell include transcriptional terminators, enhancers and the like, all of which may be included in the chimeric nucleic acid sequences of the present disclosure.

In accordance with the present disclosure, the chimeric nucleic acid sequences comprising a promoter capable of controlling expression in host cell linked to a nucleic acid sequence encoding a neopinone isomerase, can be integrated into a recombinant expression vector which ensures good expression in the host cell. Accordingly, the present disclosure includes a recombinant expression vector comprising as operably linked components:

(a) a polynucleotide comprising a nucleic acid sequence capable of controlling expression in a host cell; and (b) a polynucleotide comprising nucleic acid sequence encoding a neopinone isomerase, wherein the expression vector is suitable for expression in a host cell. The term "suitable for expression in a host cell" means that the recombinant expression vector comprises the chimeric nucleic acid sequence of the present disclosure linked to genetic elements required to achieve expression in a host cell. Genetic elements that may be included in the expression vector in this regard include a transcriptional termination region, one or more nucleic acid sequences encoding marker genes, one or more origins of replication and the like. In preferred embodiments, the expression vector further comprises genetic elements required for the integration of the vector or a portion thereof in the host cell's genome, for example if a plant host cell is used the T-DNA left and right border sequences which facilitate the integration into the plant's nuclear genome.

Pursuant to the present disclosure, the expression vector may further contain a marker gene. Marker genes that may be used in accordance with the present disclosure include all genes that allow the distinction of transformed cells from non-transformed cells, including all selectable and screenable marker genes. A marker gene may be a resistance marker such as an antibiotic resistance marker against, for example, kanamycin or ampicillin. Screenable markers that may be employed to identify transformants through visual inspection include 3-glucuronidase (GUS) (U.S. Pat. Nos. 5,268,463 and 5,599,670) and green fluorescent protein (GFP) (Niedz et al., 1995, Plant Cell Rep., 14: 403).

One host cell that particularly conveniently may be used is *Escherichia coli*. The preparation of the *E. coli* vectors may be accomplished using commonly known techniques such as restriction digestion, ligation, gel electrophoresis, DNA sequencing, the Polymerase Chain Reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Typically, these cloning vectors contain a marker allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells. Further, general guidance with respect to the preparation of recombinant vectors and growth of recombinant organisms may be found in, for example: Sambrook et al., Molecular Cloning, a Laboratory Manual, Cold Spring Harbor Laboratory Press, 2001, Third Ed.

Further included in the present disclosure are a host cell wherein the host cell comprises a chimeric nucleic acid sequence comprising in the 5' to 3' direction of transcription as operably linked components one or more polynucleotides comprising nucleic acid sequences encoding a neopinone isomerase. As hereinbefore mentioned the host cell is preferably a host cell capable of producing a morphinan alkaloid having chemical structure (I), not a morphinan alkaloid having chemical structure (II), but for the introduction of the chimeric nucleic acid sequences of the present disclosure.

As hereinbefore mentioned, in other embodiments, the host cells naturally produce a morphinan compound having chemical structure (II), however the host cells are modulated in such a manner that the levels of the morphinan compound having chemical structure (II) produced in the cells is modulated, relative to levels of such morphinan compound produced by the cell without heterologous introduction of the herein enzymes in such host cells. Such modulations may be achieved by a variety of modification techniques, including, but not limited to, the modulation of the enzymatic activity of an neopinone isomerase, for example by modulating the native nucleic acid sequences encoding the neopinone isomerase, for example by gene silencing methodologies, such as antisense methodologies; or by the use of modification techniques resulting in modulation of activity of the enzymes using for example site directed mutagenesis, targeted mutagenesis, random mutagenesis, virus-induced gene silencing, the addition of organic solvents, gene shuffling or a combination of these and other techniques known to those of skill in the art, each methodology designed to alter the activity of the enzymes of the neopinone isomerase, in such a manner that level of product morphinan compound in the host cells increases.

In some embodiments, the hereinbefore mentioned methods to modulate expression levels of the polynucleotides encoding neopinone isomerase of the present disclosure may result in modulations in the levels of plant alkaloids, including without limitation in the levels of morphine, codeine and codeinone. Thus, the present disclosure includes the use of the methodologies to modify the levels of plant morphinan alkaloids, in a plant naturally capable of producing plant morphinan alkaloid compounds.

In some embodiments the plant belongs to the plant family of Papaveraceae.

In some embodiments, the plant belongs to the plant species *Papaver somniferum, Papaver bracteatum, Papaver nudicale, Papaver orientale* or *Papaver rhoeas*.

In another aspect of the present disclosure, the polynucleotides encoding a neopinone isomerase may be used to examine the presence of the polynucleotide in a cell, or a cell extract, such as a polynucleotide containing extract. Accordingly, in some embodiments the polynucleotides encoding neopinone isomerase may be labeled and used as a probe to examine the presence of the polynucleotide in a cell, or a cell extract.

In another aspect of the present disclosure, the polynucleotides encoding neopinone isomerase of the present disclosure may be used to genotype plants.

In some embodiments, the plant belongs to the plant family of Papaveraceae.

In some embodiments, the plant belongs to the species *Papaver somniferum, Papaver bracteatum, Papaver nudicale, Papaver orientale* or *Papaver rhoeas*.

In general, genotyping provides a means of distinguishing homologs of a chromosome pair and can be used to identify segregants in subsequent generations of a plant population. Molecular marker methodologies can be used for phylogenetic studies, characterizing genetic relationships among plant varieties, identifying crosses or somatic hybrids, localizing chromosomal segments affecting monogenic traits, map based cloning, and the study of quantitative inheritance. See, e.g., Plant Molecular Biology: A Laboratory Manual, Chapter 7, Clark, Ed., Springer-Verlag, Berlin (1997). For molecular marker methodologies, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7-21. The particular method of genotyping in accordance with the present disclosure may involve the employment of any molecular marker analytic technique including, but not limited to, restriction fragment length polymorphisms (RFLPs). RFLPs reflect allelic differences between DNA restriction fragments caused by nucleic acid sequence variability. As is known to those of skill in the art, RFLPs are typically detected by extraction of plant genomic DNA and digestion of the genomic DNA with one or more restriction enzymes. Typically, the resulting fragments are separated according to size and hybridized with a nucleic acid probe. Restriction fragments from homologous chromosomes are revealed. Differences in fragment size among alleles represent an RFLP. Thus, the present disclosure further provides a means to follow segregation of a portion or genomic DNA encoding a polynucleotide of the present disclosure, as well as chromosomal nucleic acid sequences genetically linked to these polynucleotides using such techniques as RFLP analysis. Linked chromosomal nucleic sequences are within 50 centiMorgans (cM), often within 40 or 30 cM, preferably within 20 or 10 cM, more preferably within 5, 3, 2, or 1 cM of a genomic nucleic acid sequence encoding a polypeptide of the present disclosure. Thus, in accordance with the present disclosure the polynucleotides of the present disclosure may be used as markers to evaluate in a plant population the segregation of polynucleotides genetically linked thereto. In some embodiments, the plant population comprises or consists of plants belonging to the plant families Papaveraceae. In other embodiments, the plant population comprises or consists of plants belonging to the plants species *Papaver somniferum, Papaver bracteatum Papaver nudicale, Papaver orientale* or *Papaver rhoeas*.

In accordance with the present disclosure, the polynucleotide probes employed for molecular marker mapping of plant nuclear genomes selectively hybridize, under selective hybridization conditions, to a genomic sequence encoding a polypeptide of the present disclosure, including, in specific embodiments polypeptides comprising the amino acid sequence set forth in SEQ. ID NO: 2, or SEQ. ID NO: 54.

Typically, these probes are cDNA probes. Typically, these probes are at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid plant chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves a polynucleotide at a specific nucleic acid sequence.

Other methods of differentiating polymorphic (allelic) variants of the nucleic acid sequences of the present disclosure can be used by utilizing molecular marker techniques well known to those of skill in the art, including, without limitation: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include, without limitation, clamped denaturing gel electrophoresis (CDGE); heteroduplex analysis (HA), and chemical mismatch cleavage (CMC).

Thus, the present disclosure further provides a method of genotyping comprising the steps of contacting, under stringent hybridization conditions, a sample suspected of comprising a nucleic acid encoding a polypeptide of the present disclosure, including, in specific embodiments polypeptides comprising the amino acid sequence set forth in SEQ. ID NO: 2, or SEQ. ID NO: 54 with a nucleic acid probe capable of hybridizing to a polynucleotide sequence encoding the foregoing. Generally, the sample is a plant sample, and in some embodiments, a sample suspected of comprising a *Papaver somniferum* nucleic acid sequence encoding polynucleotides of the present disclosure. The polynucleotide probe selectively hybridizes, under stringent conditions, to a subsequence of the nucleic acid sequence encoding the polypeptide comprising a polymorphic marker. Selective hybridization of the polynucleotide probe to the polymorphic marker nucleic acid sequence yields a hybridization complex. Detection of the hybridization complex indicates the presence of that polymorphic marker in the sample. In preferred embodiments, the polynucleotide probe comprises a portion of a nucleic acid sequence encoding polypeptide of the present disclosure.

Uses of Morphinan Compounds

It will be clear form the foregoing that the neopinone isomerase according to the present disclosure may be used in a variety of processes and In another aspect, the present disclosure provides, in at least one embodiment, a use of a neopinone isomerase as a catalytic agent in a reaction to make a second morphinan product having a saturated carbon bond at position $C_8$-$C_{14}$ and a mono-unsaturated carbon bond at position $C_7$-$C_8$, using a first morphinan having a mono-unsaturated carbon bond at position $C_8$-$C_{14}$ and a saturated carbon bond at position $C_7$-$C_8$ as a substrate.

In some embodiments, the first and second morphinan can possess a bridging oxygen atom between carbon atoms $C_4$ and $C_5$, forming a tetrahydrofuranyl ring within the morphinan chemical structure.

In some embodiments, the first morphinan can be a chemical compound having the chemical structure (I):

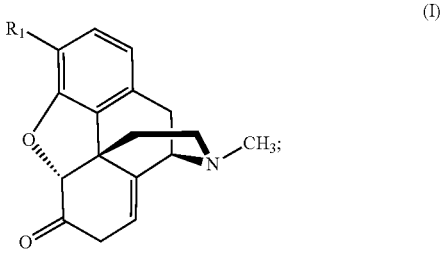

(I)

and
the second morphinan can be a chemical compound having the chemical structure (II):

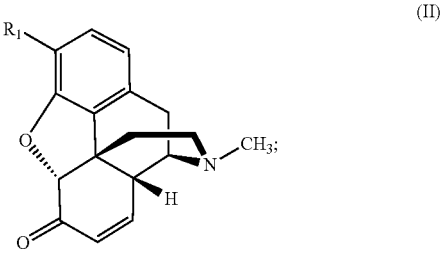

(II)

wherein $R_1$ is either a hydroxyl group, or a methoxy group.

The morphinan alkaloid compounds obtained in accordance with the present disclosure may be formulated for use as a pharmaceutical drug, therapeutic agent or medicinal agent. Thus the present disclosure further includes a pharmaceutical composition comprising a morphinan compound prepared in accordance with the methods of the present disclosure. Pharmaceutical drug preparations comprising a morphinan product in accordance with the present disclosure can comprise vehicles, excipients and auxiliary substances, such as wetting or emulsifying agents, pH buffering substances and the like. These vehicles, excipients and auxiliary substances are generally pharmaceutical agents that may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, phosphates, sulfates, and the like; and the salts of organic acids such as acetates, propionates, benzoates, and the like. It is also preferred, although not required, that the preparation will contain a pharmaceutically acceptable excipient that serves as a stabilizer. Examples of suitable carriers that also act as stabilizers for peptides include, without limitation, pharmaceutical grades of dextrose, sucrose, lactose, sorbitol, inositol, dextran, and the like. Other suitable carriers include, again without limitation, starch, cellulose, sodium or calcium phosphates, citric acid, glycine, polyethylene glycols (PEGs), and combinations thereof. The pharmaceutical composition may be formulated for oral and intravenous administration and other routes of administration as desired. Dosing may vary and may be optimized using routine experimentation.

In another aspect, the present disclosure further provides, in an embodiment, a use of a morphinan compound prepared in accordance with any one of the methods of the present disclosure to prepare a pharmaceutical composition comprising the morphinan compound.

The morphinan compounds of the present disclosure further may be used as precursor or feedstock material for the production of derivative morphinan compounds. Thus, for example, as has been described herein, codeinone made in accordance with the present disclosure can be used as a precursor to make codeine, codeine can be used as a precursor to make morphine, and morphinone can be used as a precursor compound to make morphine. It will be clear to those of skill in the art that the morphinone compounds made in accordance with the present disclosure can be used to make a wide variety of derivative morphinan compounds. Upon finishing synthesis the morphinan compounds can be used to formulate pharmaceutical drugs, as hereinbefore described.

In further embodiments, the present disclosure provides methods for treating a patient with a pharmaceutical composition comprising a morphinan compound prepared in accordance with the present disclosure. Accordingly, the present disclosure further provides a method for treating a patient with a morphinan compound prepared according to the methods of the present disclosure, the method comprising administering to the patient a pharmaceutical composition comprising a morphinan compound, wherein the pharmaceutical composition is administered in an amount sufficient to ameliorate a medical condition in the patient.

SUMMARY OF SEQUENCES

SEQ. ID NO: 1 sets forth a polynucleotide sequence encoding a neopinone isomerase polypeptide.

SEQ. ID NO: 2 sets forth a deduced amino acid sequence of a neopinone isomerase polypeptide.

SEQ. ID NO: 3 sets forth a polynucleotide sequence encoding a codeinone reductase polypeptide.

SEQ. ID NO: 4 sets forth a deduced amino acid sequence of a codeinone reductase polypeptide.

SEQ. ID NO: 5 sets forth a polynucleotide sequence encoding a T6-O-demethylase polypeptide.

SEQ. ID NO: 6 sets forth a deduced amino acid sequence of a T-6-O-polypeptide.

SEQ. ID NO: 7 sets forth a polynucleotide sequence encoding a codeine-O-demethylase polypeptide.

SEQ. ID NO: 8 sets forth a deduced amino acid sequence of a codeine-6-O-polypeptide.

SEQ. ID NO: 9 sets forth a polynucleotide sequence encoding a neopinone isomerase polypeptide.

SEQ. ID NO: 10 sets forth a polynucleotide sequence encoding a PR polypeptide (PR10-8).

SEQ. ID NO: 11 sets forth a deduced amino acid sequence encoding a PR-polypeptide (PR10-8).

SEQ. ID NO: 12 sets forth a polynucleotide sequence encoding a neopinone isomerase polypeptide (codon optimized).

SEQ. ID NO: 13 sets forth a polynucleotide sequence encoding a morphinone reductase polypeptide.

SEQ. ID NO: 14 sets forth a polynucleotide sequence encoding a portion of the neopinone isomerase polypeptide set forth in SEQ. ID NO: 1.

SEQ. ID NO: 15 sets forth a polynucleotide sequence encoding a portion of the neopinone isomerase polypeptide set forth in SEQ. ID NO: 1.

SEQ. ID NO: 16 sets forth a polynucleotide sequence encoding a portion of a the neopinone isomerase polypeptide set forth in SEQ. ID NO: 1.

SEQ. ID NO: 17 sets forth a polynucleotide sequence encoding a portion of the neopinone isomerase polypeptide set forth in SEQ. ID NO: 1.

SEQ. ID NO: 18 sets forth a deduced amino acid sequence of a portion of the neopinone isomerase polypeptide set forth in SEQ. ID NO: 2.

SEQ. ID NO: 19 sets forth a deduced amino acid sequence of a portion of the neopinone isomerase polypeptide set forth in SEQ. ID NO: 2.

SEQ. ID NO: 20 sets forth a deduced amino acid sequence of a portion of the neopinone isomerase polypeptide set forth in SEQ. ID NO: 2.

SEQ. ID NO: 21 sets forth a deduced amino acid sequence of a portion of the neopinone isomerase polypeptide set forth in SEQ. ID NO: 2.

SEQ. ID NO: 22 sets forth a deduced amino acid sequence of a morphinone reductase B polypeptide.

SEQ. ID NO: 23 sets forth a polynucleotide sequence of a PR-polypeptide (MLP-2).

SEQ. ID NO: 24 sets forth a deduced amino acid sequence of a PR-polypeptide (MLP-2).

SEQ. ID NO: 25 sets forth a polynucleotide sequence of a PR-polypeptide (MLP-3).

SEQ. ID NO: 26 sets forth a deduced amino acid sequence of a PR-polypeptide (MLP-3).

SEQ. ID NO: 27 sets forth a polynucleotide sequence of a PR-polypeptide (MLP-4).

SEQ. ID NO: 28 sets forth a deduced amino acid sequence of a PR-polypeptide (MLP-4).

SEQ. ID NO: 29 sets forth a polynucleotide sequence of a PR-polypeptide (MLP-15).

SEQ. ID NO: 30 sets forth a deduced amino acid sequence of a PR-polypeptide (MLP-15).

SEQ. ID NO: 31 sets forth a polynucleotide sequence of a PR-polypeptide (PR10-4).

SEQ. ID NO: 32 sets forth a deduced amino acid sequence of a PR-polypeptide (PR10-4).

SEQ. ID NO: 33 sets forth a polynucleotide sequence of a PR-polypeptide (PR10-5).

SEQ. ID NO: 34 sets forth a deduced amino acid sequence of a PR-polypeptide (PR10-5).

SEQ. ID NO: 35 sets forth a polynucleotide sequence of a PR-polypeptide (PR10-7).

SEQ. ID NO: 36 sets forth a deduced amino acid sequence of a PR-polypeptide (PR10-7).

SEQ. ID NO: 37 sets forth a polynucleotide sequence of a PR-polypeptide (PR10-8).

SEQ. ID NO: 38 sets forth a deduced amino acid sequence of a PR-polypeptide (PR10-8).

SEQ. ID NO: 39 sets forth a polynucleotide sequence of a PR-polypeptide (PR10-9).

SEQ. ID NO: 40 sets forth a deduced amino acid sequence of a PR-polypeptide (PR10-9).

SEQ. ID NO: 41 sets forth a polynucleotide sequence of a PR-polypeptide (PR10-10).

SEQ. ID NO: 42 sets forth a deduced amino acid sequence of a PR-polypeptide (PR10-10).

SEQ. ID NO: 43 sets forth a polynucleotide sequence of a PR-polypeptide (PR10-11).

SEQ. ID NO: 44 sets forth a deduced amino acid sequence of a PR-polypeptide (PR10-11).

SEQ. ID NO: 45 sets forth a polynucleotide sequence of a PR-polypeptide (PR10-12).

SEQ. ID NO: 46 sets forth a deduced amino acid sequence of a PR-polypeptide (PR10-12).

SEQ. ID NO: 47 sets forth a polynucleotide sequence of a PR-polypeptide (PR10-13).

SEQ. ID NO: 48 sets forth a deduced amino acid sequence of a PR-polypeptide (PR10-13).

SEQ. ID NO: 49 sets forth a polynucleotide sequence of a PR-polypeptide (PR10-14).

SEQ. ID NO: 50 sets forth a deduced amino acid sequence of a PR-polypeptide (PR10-14).

SEQ. ID NO: 51 sets forth a polynucleotide sequence of a PR-polypeptide (PR10-15).

SEQ. ID NO: 52 sets forth a deduced amino acid sequence of a PR-polypeptide (PR10-15).

SEQ. ID NO: 53 sets forth a polynucleotide sequence encoding a neopinone isomerase polypeptide (truncated).

SEQ. ID NO: 54 sets forth a deduced amino acid sequence of a neopinone isomerase polypeptide (truncated).

SEQ. ID NO: 55 sets forth a polynucleotide sequence of a PR-polypeptide (MLP-1).

SEQ. ID NO: 56 sets forth a deduced amino acid sequence of a PR-polypeptide (MLP-1).

SEQ. ID NO: 57 sets forth a polynucleotide sequence of a thebaine synthase polypeptide.

SEQ. ID NO: 58 sets forth a deduced amino acid sequence of a thebaine synthase polypeptide.

EXAMPLES

Hereinafter are provided examples of specific implementations for performing the methods of the present disclosure, as well as implementations representing the compositions of the present disclosure. The examples are provided for illustrative purposes only, and are not intended to limit the scope of the present disclosure in any way.

Example 1—Cloning and Sequencing of Gene Encoding Neopinone Isomerase

The *Papaver somniferum* neopinone isomerase gene was cloned and sequenced. The neopinone isomerase gene was identified within a subset of genes encoding pathogenesis-related 10 (PR10) proteins, based on gene expression and protein abundance profiles in various opium poppy (*Papaver somniferum*) organs, tissues and cell types and cellular fractions. Nucleic acid sequences are set forth in SEQ. ID NO: 1 (including some 5' and 3' upstream and downstream sequences and SEQ. ID NO: 9 (coding sequence only). The amino acid sequence is set forth in SEQ. ID NO: 2.

Example 2—Expression of Neopinone Isomerase in *E. coli*

Figure 6:
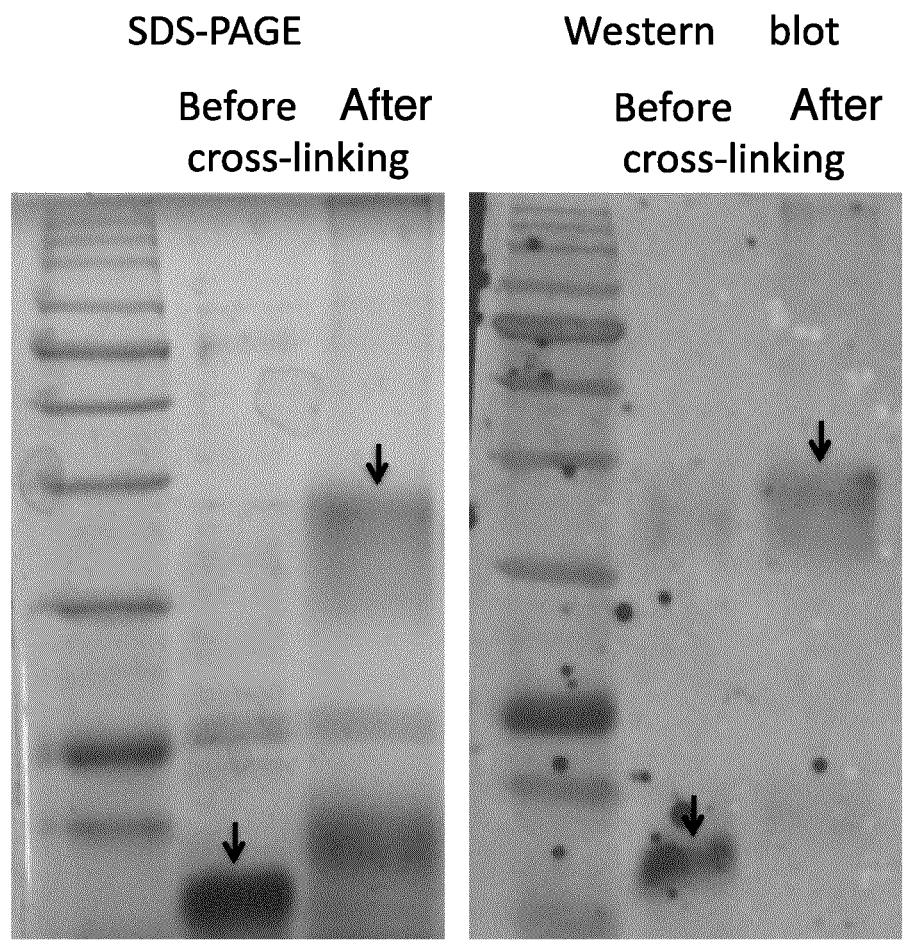
FIG. 6 depicts certain experimental results, notably a photograph of an SDS PAGE gel electrophoresis experiment showing the expression of neopinone isomerase in *Escherichia coli*.

A codon-optimized PR10-3 gene (SEQ. ID NO: 12), encoding neopinone isomerase (NISO) was expressed in *Escherichia coli* with a His$_6$-tag on the N-terminus, and cloned into the pACE vector or pET 19b vector. Expression vectors were transformed into *E. coli* stain Rosetta (DE3) pLysS (EMD Chemicals), which were subsequently induced overnight using 0.2 mM isopropyl β-D-thiogalactoside (IPTG) at 16° C. Cells were harvested by centrifugation and sonicated in 50 mM sodium phosphate, pH 7.0, 300 mM NaCl and 10% (v/v) glycerol. After centrifugation at 20,000 g for 10 min, the supernatant was loaded onto Talon (Clontech) cobalt-affinity resin. Purification was performed according to the manufacturer's instructions. Purified, recombinant proteins were desalted using PD 10 column (GE healthcase), and stored in 50 mM sodium phosphate, pH 7.0, 50 mM NaCl and 10% (v/v) glycerol. Protein concentration was determined by the Bradford assay (Bio-Rad) using bovine serum albumin as the standard. Chemical crosslinking was performed to demonstrate that neopinone isomerase functions as a homodimer. Briefly, the crosslinking reagent bis[sulfosuccinimidyl] suberate (BS3) was prepared at a concentration of 10 mM in PBS buffer (10 mM sodium phosphate buffer, pH 7.4, 137 mM NaCl, 2.7 mM KCl). The BS3 solution (2 μL) was added to 20 μL of purified protein (1 μg/L). The reaction was incubated on ice for 1 h followed by the addition of 5 μL of 10% (w/v) sodium dodecyl sulfate to quench the reaction. Protein samples were then boiled for 5 min and subjected to SDS-PAGE and immunoblot analysis. SDS-PAGE results are shown in FIG. 6.

Example 3—Expression of Neopinone Isomerase in Yeast

Yeast strains with chromosome-integrated T6ODM and COR1.3 genes were constructed using a USER cloning system. USER (uracil-specific excision reaction)-based cloning has been used for the integration of multiple genes into the yeast genome owing to its relatively straightforward application and independence from the enzyme-based ligation of DNA fragments. Multiple PCR products of BIA biosynthetic genes and Gal1/Gal10 promoter regions were simultaneous cloned to the USER cloning vectors initially nicked with AsiSI and Nb.BsmI and then transformed into yeast cells using the LiAc/PEG/single-stranded carrier DNA (ssDNA) transformation method. The high-copy number pESC-Ura (or, alternatively, pESC-Leu or pESC-His) vector was used to express neopinone isomerase (NISO) gene candidates using the Gal10 promoter. PCR-amplified candidate genes from cDNA using primers flanked with SpeI and NotI restriction sites were ligated to the pESC-Ura vector to generate transient expressing constructs. Transient expression constructs were individually transformed to the platform yeast strains with chromosome-integrated BIA biosynthetic genes using the LiAc/PEG/single-stranded carrier DNA (ssDNA) transformation method. Each yeast strain transiently expressing a candidate gene was inoculated in SD-drop out medium overnight. The overnight cultures were then diluted into a SD-drop out medium containing 2% (w/v) galactose and 200 μM of the BIA suitable for conversion by the baseline yeast strain and/or the transient expression construct. Yeast cultures were grown for 24 h.

Example 4—Neopinone Isomerase In Vitro Activity

NISO PR10-Type Protein-Coupled T6ODM-COR Assays with Thebaine as Substrate

Figure 7:
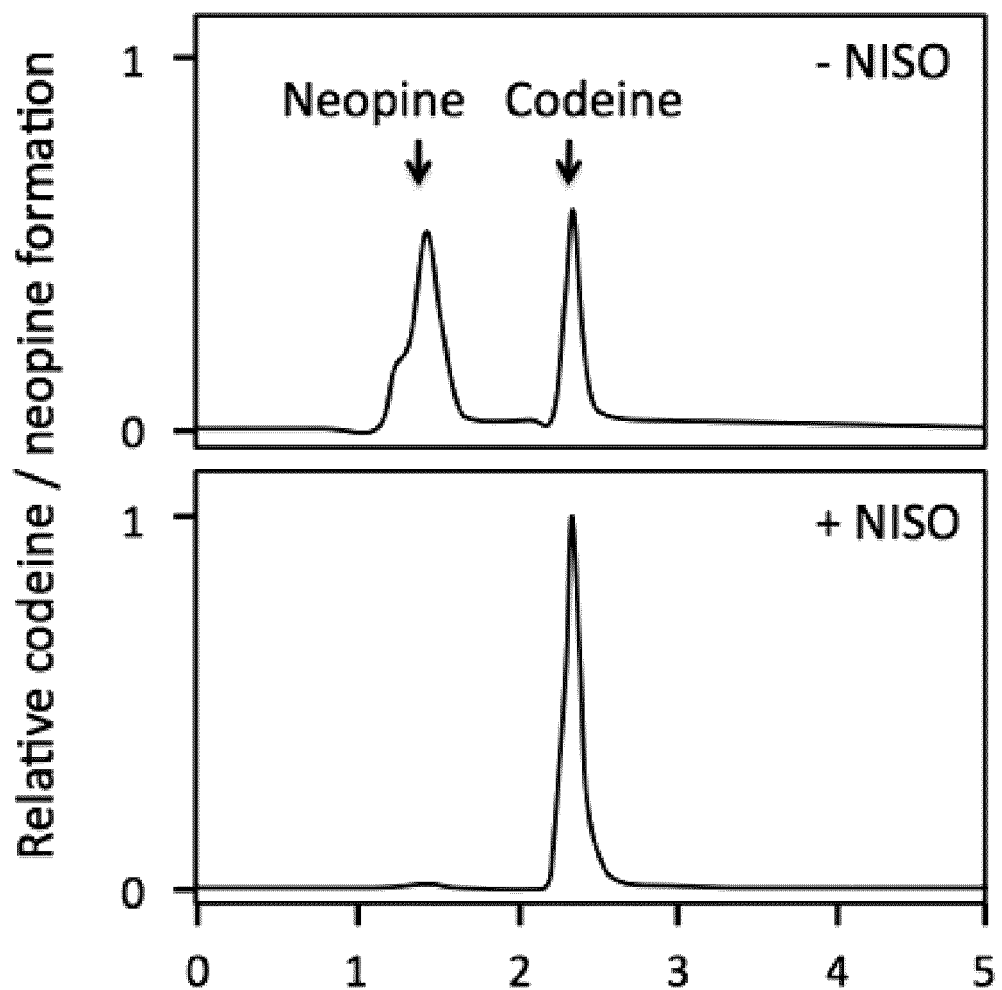
FIG. 7 depicts certain experimental results, notably LC-MS/MS trace obtained in the performance of a neopinone isomerase in vitro assay.
Figure 8:
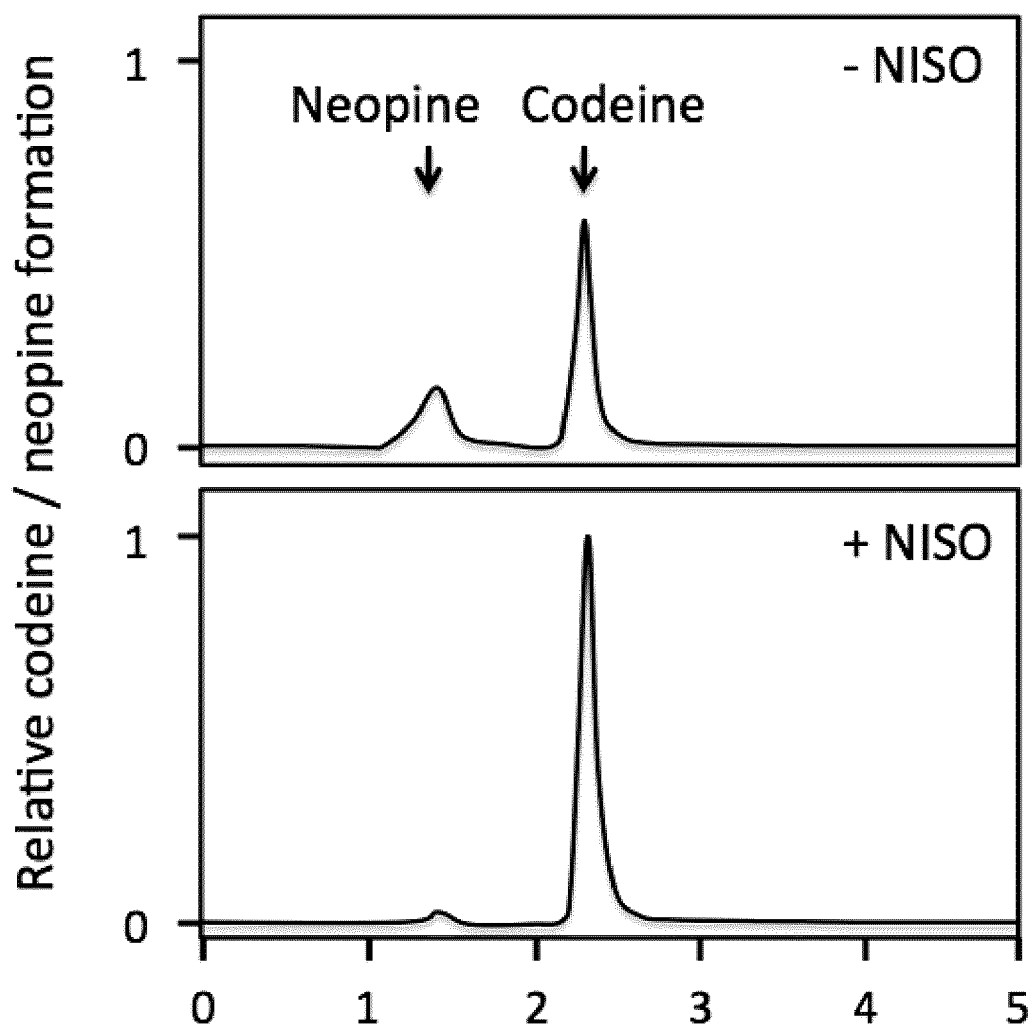
FIG. 8 depicts certain experimental results, notably LC-MS/MS trace obtained in the performance of another a neopinone isomerase in vitro assay
Figure 15:
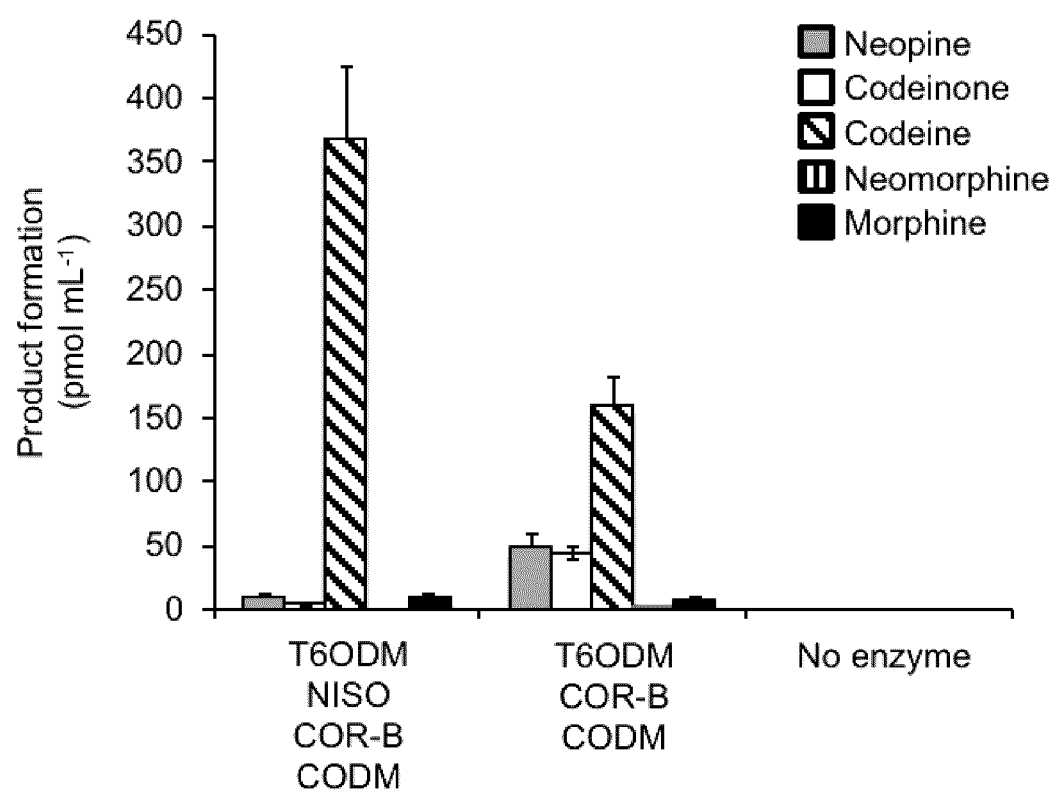
FIG. 15 depicts certain experimental results, notably bar graphs obtained in the performance of an experiment evaluating morphinan alkaloid compound production in assays using no enzyme; T6ODM, COR and CODM; or T6ODM, COR, CODM and NISO. The morphinan alkaloids evaluated are: neopine, codeinone, codeine, neomorphine and morphine, as indicated by the legend in FIG. 15.

A 50 μL-reaction mixture containing purified recombinant T6ODM (~9 μg), purified recombinant COR1.3 (~1-6 μg), 100 μM thebaine, 800 μM NADPH, 8 mM α-ketoglutaric acid, 800 μM ferrous sulfate, and 8 mM Na-ascorbate in 50 mM Bis-tris propane (pH 7.0 or 6.0) buffer was incubated at 30° C. for 1 hr. When indicated, assays also included NISO (~0.5 μg). All assays were quenched with 200 μL of acetonitrile and centrifuged at 17,000 g for 40 min. The supernatant was analyzed by LC-MS/MS. Results are shown in FIG. 7.
NISO PR10-Type Protein-Coupled COR Activity Assays Using Codeinone or Morphinone as Substrate A 50 μL-reaction mixture containing individual purified recombinant NISO (~5-10 μg), purified recombinant COR1.3 (~1-6 μg), 80 μM codeinone or morphinone, 800 μM NADPH in 50 mM Bis-tris propane (pH 7.0 or 6.0) buffer was incubated at 30° C. for 1 hr. When indicated, assays also included NISO (~0.6 μg). All assays were quenched with 200 μL of acetonitrile and centrifuged at 17,000 g for 40 min. The supernatant was analyzed by LC-MS/MS. Results are shown in FIG. 8.
NISO PR10-Type Protein-Coupled T6ODM-COR CODM Assays with Thebaine as Substrate—Detection of Morphine A 50 μL-reaction mixture containing purified recombinant T6ODM (~9 μg), purified recombinant COR1.3 (~1-6 μg), purified CODM, 100 μM thebaine, 800 μM NADPH, 8 mM α-ketoglutaric acid, 800 μM ferrous sulfate, and 8 mM Na-ascorbate in 50 mM Bis-tris propane (pH 7.0 or 6.0) buffer was incubated at 30° C. for 1 hr. When indicated, assays also included NISO (~0.5 μg). All assays were quenched with 200 μL of acetonitrile and centrifuged at 17,000 g for 40 min. The supernatant was analyzed by LC-MS/MS. Results are shown in FIG. 15. As can be seen in FIG. 15 in the presence of NISO codeine production increases substantially. Furthermore, morphine production increases as well. By contrast neopine production is reduced.

Example 5—Neopinone Isomerase In Vivo Activity

Figure 9:
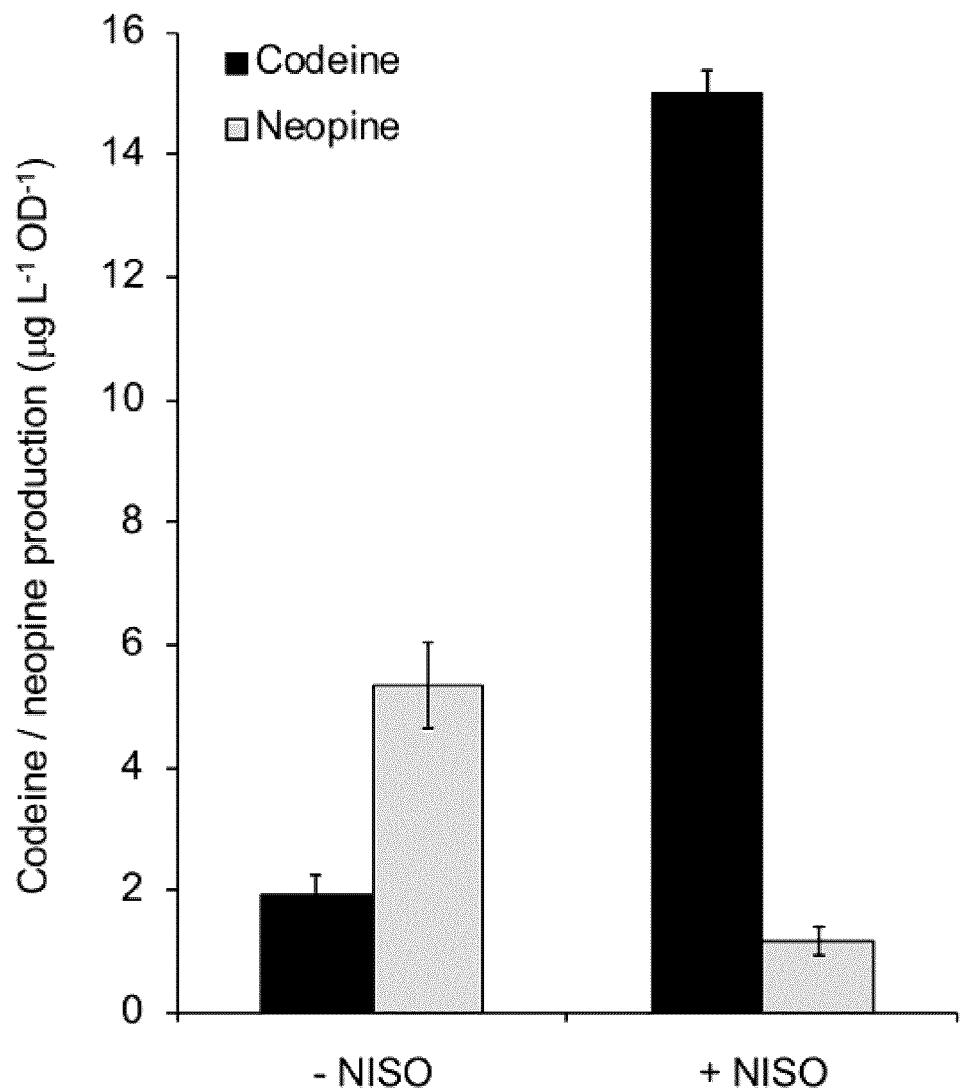
FIG. 9 depicts certain experimental results, notably a bar graph obtained in the performance of a neopinone isomerase in vivo assay.

Yeast cells expressing neopinone isomerase were prepared as described in Example 3. Yeast cells were removed from their culture medium by centrifugation and 5 μL of supernatant, containing alkaloids secreted by the yeast cells into the culture medium, was subjected to high-resolution mass spectrometry (MS) analysis. Alkaloids produced in yeast were characterized by high-resolution MS$^n$ analysis. For MS$^n$ experiments, alkaloids were injected by HPLC for electrospray ionization (ESI) prior to analysis by LTQ-Orbitrap-XL. Operation was conducted using LTQ Tune Plus v. 2.5.5 SP1 and Xcalibur v. 2.1.0.1140, with additional analyses using QualBrowser feature of Xcalibur. Internal calibration, external calibration, tuning, and general operations were performed using routine procedures optimized for alkaloid detection, with the exception that ESI, rather than heated HESI, was employed with reduced flow rates to minimize heat-induced degradation of analytes during ionization. Data acquisition for MS$^2$ was performed using a single scan event, involving CID conducted in linear ion trap (IT) with normalized collision energy (NCE) of 35%, and detection by FTMS with resolution of 60,000 FWHM and scan range m/z 90-340. Data acquisition for MS$^3$ was performed by first identifying the most intense ions in $MS^2$, optimizing NCE for CID-based fragmentation of these ions (15-35%), and adjusting FTMS scan ranges for detection of $MS^3$ ions. To ensure sufficient $MS^3$ detection by FTMS, individual runs comprised of only one scan event were conducted for each $MS^2$ ion subjected to CID analysis. Error was maintained at <2 ppm to allow prediction of elemental formulae for all ions. Compound identity was based on comparisons with authentic standards and $MS^n$ assignments available in the literature. Results are shown in FIG. 9.

Example 6—Gene-Silencing of Neopinone Isomerase

Virus induced gene silencing (VIGS) of a nucleic acid sequence encoding neopine isomerase was performed using the tobacco rattle virus (TRV) vector system, which is based on the pYL156 plasmid, as described previously (Hagel and Facchini, 2010). The vector used to silence NISO expression, labeled pPR10-3, targeted a 187 bp region of the coding sequence. *Agrobacterium tumefaciens* strains harboring (i) pTRV1 and (ii) either pPR10-3 or the empty pTRV2 vector were co-inoculated at a 1:1 ratio into the cotyledons and apical meristem of 2 to 3-week-old opium poppy, Bea's choice variety, seedlings and leaves using a needleless syringe. Infiltrated plants were harvested after 8 to 12 weeks of growth. Tissue was harvested for RNA extraction as described above, from a 2 cm section of stem located approximately 1 cm below the flower bud.

Plants were screened for infection by RT-PCR to identify samples containing sequences specific to pYL156 plasmid (GAPDH). Samples included 10 and 12 plants containing pPR10-3 and pTRV2 constructs, respectively. Stem cDNA from selected plants was analyzed by qRT-PCR to determine relative transcript abundance. Latex was collected from flower buds for alkaloid analysis. Latex samples were freeze-dried for 24 h and resuspended in a solution of methanol and acetonitrile (1:1) to a final concentration of 25 µg (dry weight)/µL. Samples were incubated on a shaker at room temperature and 200 rpm for 4 h. Extracts were centrifuged at 21,000×g for 20 min at 4° C. and the supernatant prepared for LC-MS analysis. Major alkaloids, thebaine, noscapine and papaverine were analyzed by 10 µL injection of a 1:50 dilution, using full-scan mode. For targeted analysis of codeinone, neopine, codeine, morphinone, neomorphine and morphine, 2 µL of undiluted sample was analyzed by MRM to identify trace amounts of metabolites.

Suppression of NISO transcript abundance in opium poppy by VIGS lead to a significant drop in morphine (FIG. 10F) accumulated in the latex, and an increase in upstream metabolites including thebaine (FIG. 10B), codeinone (FIG. 10C), neopine (FIG. 10D) and codeine (FIG. 10E). The greatest change in metabolite levels was recorded for neopine, which increased 10-fold, from 6.7 to 69 µg $g^{-1}$ dry weight. (FIG. 10). NISO transcript levels were significantly suppressed (pPR10-3) (p=0.0003) compared with the control (empty vector, pTRV2) (FIG. 10A). Alkaloid content (µg $g^{-1}$ dry weight) is shown for various metabolites. Values represent the mean±standard deviation of 10 and 12 biological replicates from pPR10-3 and pTRV2-infected plants, respectively. The asterisk marks statistically significant differences as determined using an unpaired, two-tailed Student t test (significant p values noted on graph).

Example 7—Identification of NISO Functional Domains

Figure 12A:
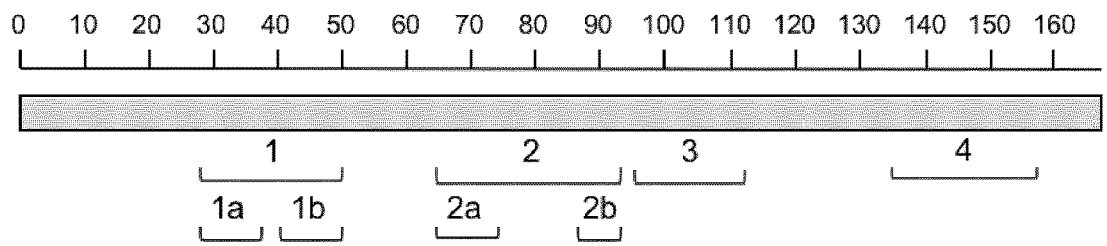
FIG. 12A further shows the location of Domain 1 (1) (including Subdomain 1a (1a), and Subdomain 1b (1b)); Domain 2 (2) (including Subdomain 2a (2a), and Subdomain 2b (2b)); Domain 3 (3); and Domain 4 (4) within the NISO polypeptide. Vertical bars in FIG. 12B represent neopine produced as a percentage of total product. All assays contained COR. Shown are results from assays comprising no NISO (-), and the inclusion of NISO (NISO), a Domain 1 mutant (Δ1), a Domain 2 mutant (Δ2), a Domain 3 mutant (Δ3), a Domain 4 mutant (Δ4), a Domain 1a mutant (Δ1a), a Domain 1b mutant (Δ1b), a Domain 2 mutant (Δ2b) and a Domain 2 mutant (Δ2b).
Figure 12B:
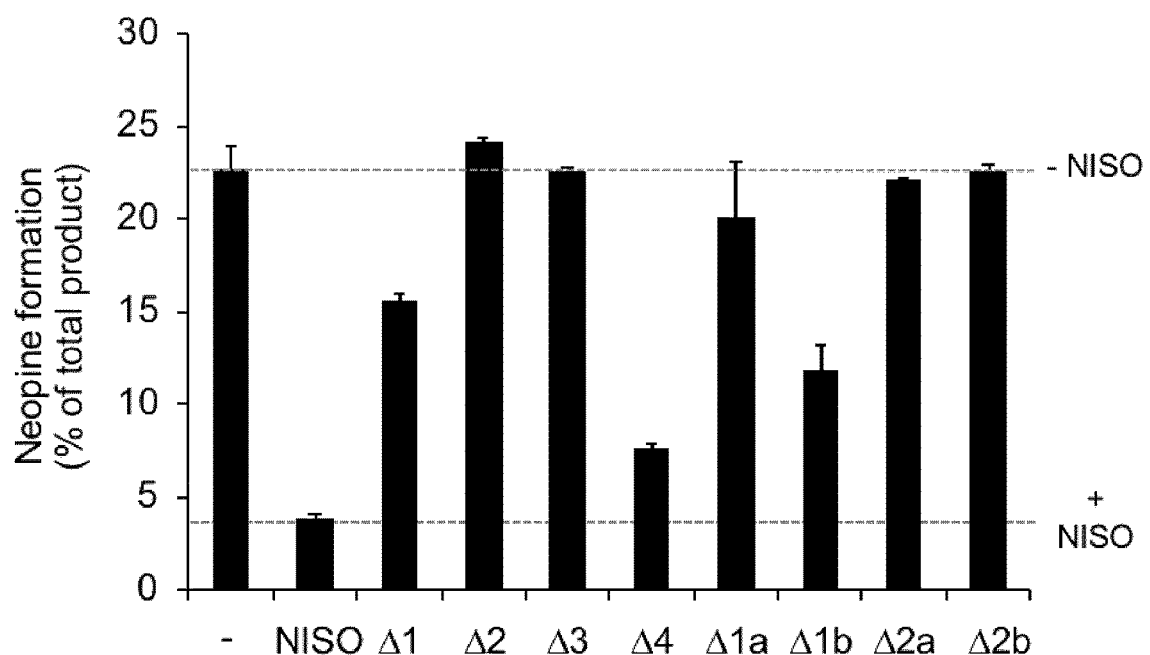
FIG. 12 depicts a schematic representation of a NISO polypeptide (FIG. 12A) and certain experimental results obtained in the performance of an experiment to evaluate the in vitro activity of NISO mutants (FIG. 12B).

Several proteins with similarity to NISO (SEQ. ID NO: 2) were identified in the *Papaver somniferum* latex transcriptome including the following proteins PR10-8 (SEQ. ID NO: 38 (nucleic acid sequence: SEQ. ID NO: 37); PR10-9 (SEQ. ID NO: 40 (nucleic acid sequence: SEQ. ID NO: 39); PR10-10 (SEQ. ID NO: 42 (nucleic acid sequence: SEQ. ID NO: 37); PR10-5 (SEQ. ID NO: 34 (nucleic acid sequence: SEQ. ID NO: 33); PR10-4 (SEQ. ID NO: 32 (nucleic acid sequence: SEQ. ID NO: 31), PR10-11 (SEQ. ID NO: 44 (nucleic acid sequence: SEQ. ID NO: 43); PR10-12 (SEQ. ID NO: 46 (nucleic acid sequence: SEQ. ID NO: 45): MLP15 (SEQ. ID NO: 30 (nucleic acid sequence SEQ. ID NO: 29); MLP1 (SEQ. ID NO: 56 (nucleic acid sequence: SEQ. ID NO: 55), MLP2 (SEQ. ID NO: 24 (nucleic acid sequence: SEQ. ID NO:23); MLP3 (SEQ. ID NO: 26 (nucleic acid sequence: SEQ. ID NO: 25); MLP4 (SEQ. ID NO: 28 (nucleic acid sequence: SEQ. ID NO: 27); PR10-14 (SEQ. ID NO: 50 (nucleic acid sequence: SEQ. ID NO: 49); PR10-15 (SEQ. ID NO: 30 (nucleic acid sequence: SEQ. ID NO: 29); and a thebaine synthase polypeptide (SEQ. ID NO: 58 (nucleic acid sequence: SEQ. ID NO: 57). Sequences of all of the foregoing were aligned as shown in FIG. 11. The following domains showing significant sequence similarity were identified: Domain 1 (SEQ. ID NO: 14) (comprising Subdomain 1a, and 1b), Domain 2 (SEQ. ID NO: 15) (comprising Subdomains 2a and 2b), Domain 3 (SEQ. ID NO: 16) and Domain 4 (SEQ. ID NO: 17) (as shown in FIG. 11). Mutant proteins Δ1, Δ2, Δ3, Δ4, Δ1a, Δ1b Δ2a, Δ2b with altered Domains 1, 2, 3, 4, 1a, 1b, 2a and 2b, respectively, were prepared and neopine formation in the presence of each of the mutant proteins and COR was assessed and compared to a positive control (intact NISO) and a negative control (no NISO). The results are shown in FIG. 12. The impact of altering Domain 1, Domain 2 and Domain 3 is particularly significant, with mutant proteins Δ1, Δ1a, Δ1b, Δ2, Δ2a, Δ2b and Δ3, showing neopine formation levels very similar to those achieved in the absence of NISO. The effect on neopine formation using the Δ4 mutant was less pronounced, but nevertheless significant in all cases. Thus all four Domains 1, 2, 3, and 4 are contributing to NISO activity.

Figure 13A:
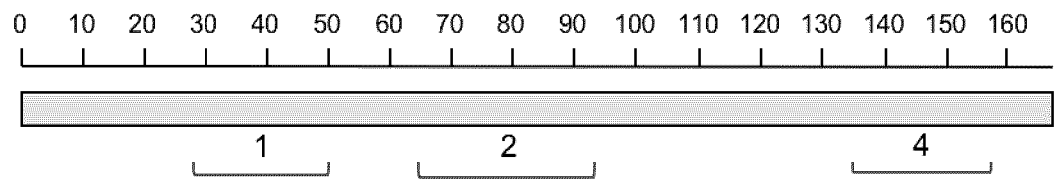
FIG. 13 depicts a schematic representation of a PR10-8 polypeptide (FIG. 13A) and certain experimental results obtained in the performance of an experiment to evaluate the activity of PR10-8 mutants (FIG. 13B) FIG. 13A further shows the location of Domain 1 (1), Domain 2 (2), and Domain 4 (4) within the PR10-8 polypeptide. Vertical bars in FIG. 13B represent neopine produced as a percentage of total product. All assays contained COR. Shown are results from assays comprising no NISO and no PR10-8 (-), and the inclusion of NISO (NISO), PR10-8 (PR10-8), a PR10-8 Domain 1 mutant (PR10-8Δ1; containing Domain 1 from NISO), a PR10-8 Domain 2 mutant (PR10-8Δ2; containing Domain 2 from NISO), a PR10-8 Domain 4 mutant (PR10-8Δ4; containing Domain 4 from NISO).
Figure 13B:
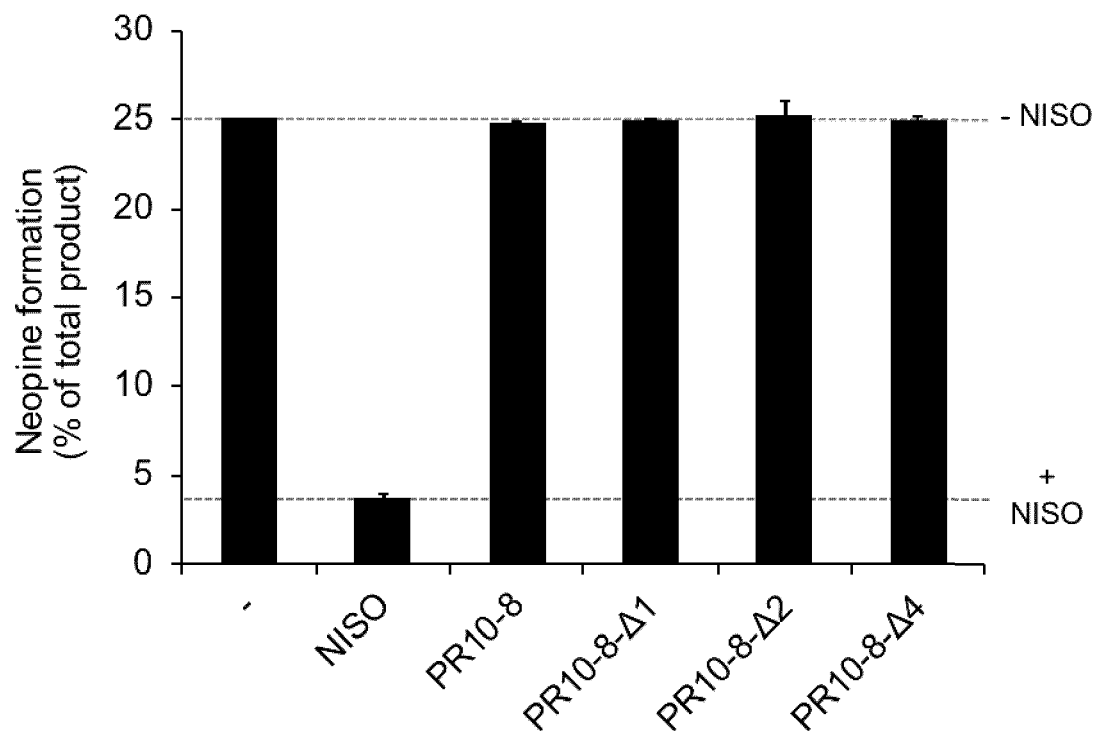

In a further experiment, PR10-8 mutant proteins were prepared, notably PR10-8Δ1, PR10-8Δ2, and PR10-8Δ4, which contained independent replacement of the indicated Domain in PR10-8 with the corresponding Domain from NISO. Neopine formation in the presence of the mutant proteins and COR was assessed, and compared to neopine formation using COR and NISOΔ1, NISOΔ2, and NISOΔ3. Results are shown in FIG. 13. In the absence of NISO, neopine constitutes about 25% of the reaction product. Neopine formation can be reduced to 5% or less in the presence of NISO. Consistent with the previous experiment, in the presence of NISOΔ1, NISOΔ2, or NISOΔ3 an increase in neopine is observed, relative to wildtype NISO. By contrast, PR10-8, as well as the PR10-8Δ1, PR10-8Δ2, and PR10-8Δ4 mutants were unable to reduce neopine production. Thus the relatively modest sequence differences between Domains Δ1, Δ2, Δ3, Δ4 of NISO and PR10-8 nevertheless are significant with respect to the ability to suppress neopine production in the presence of COR. In this respect, related polypeptides exhibiting significant sequence similarity, for example 95%, 96%, 97%, 98%, or 99% to the sequence of Domains Δ1, Δ2, Δ3, or Δ4 of NISO are likely to be particularly effective in suppressing neopine formation in the presence of COR.

Example 8—Production of Hydrocodone

Figure 14:
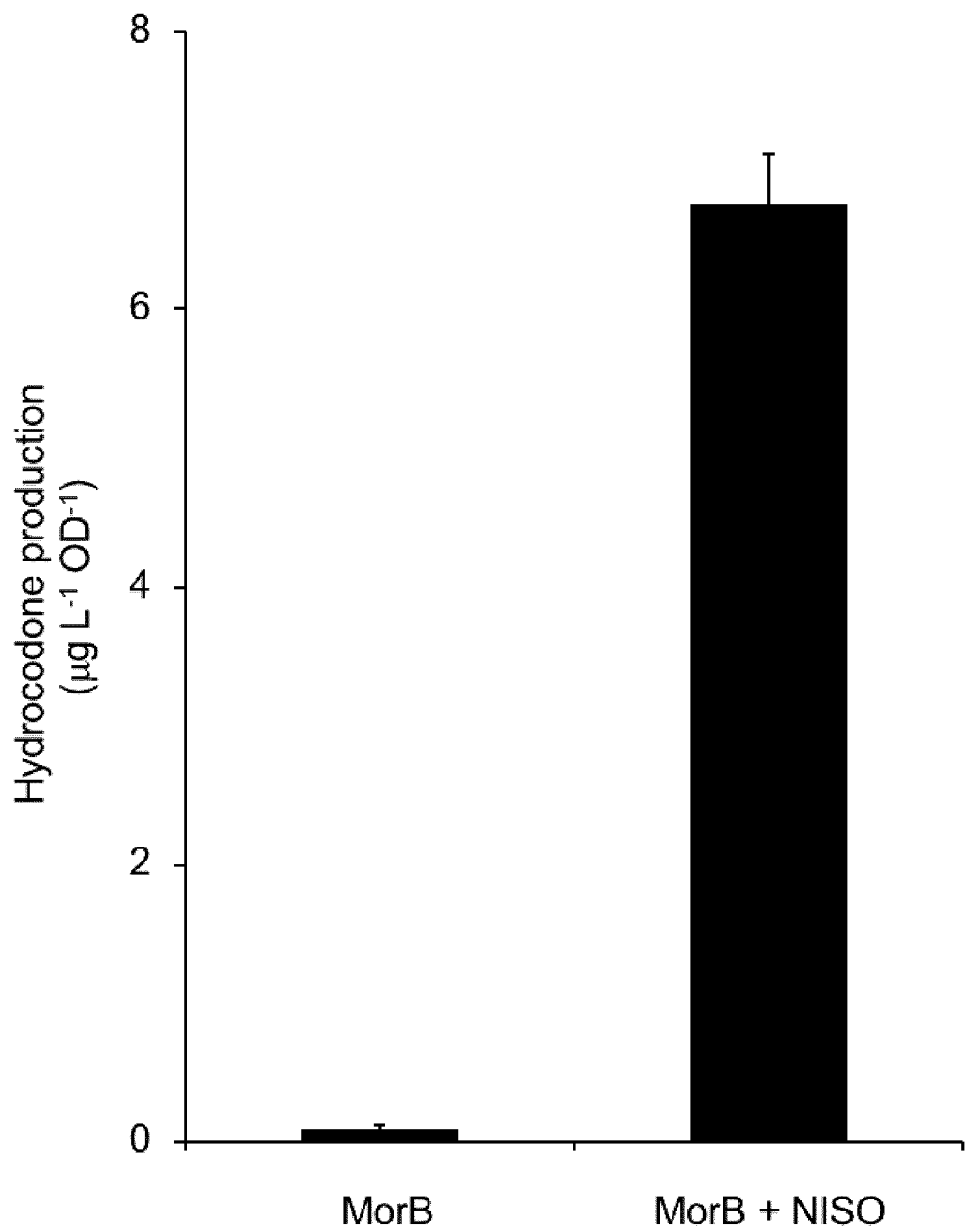
FIG. 14 depicts certain experimental results, notably bar graphs obtained in the performance of an experiment evaluating morphinan alkaloid compound production in assays using MorB alone (MorB), or a combination of NISO and MorB (MorB+NISO). The morphinan alkaloid evaluated is hydrocodone.

Yeast strains with chromosomally integrated T6ODM were transformed (as described in Example 3) with NISO, or with NISO and further a morphine reductase form *Pseudomonas putida* M10 (SEQ. ID NO: 13 (nucleic acid sequence); SEQ. ID NO: 22 (amino acid sequence), referred to as MorB. The production of hydrocone was assayed and the results are shown in FIG. 14. As can be seen in FIG. 14, in the presence of MorB alone trace amounts of hydrocone are produced. By contrast, in the presence of both NISO and MorB significant quantities of hydrocone are produced. Thus it is inferred that NISO is able to reduce neopine production and hydrocone can be produced in the presence of NISO at the expense of neopine.

Example 9—Production of Codeine and Morphine

Figure 16A:
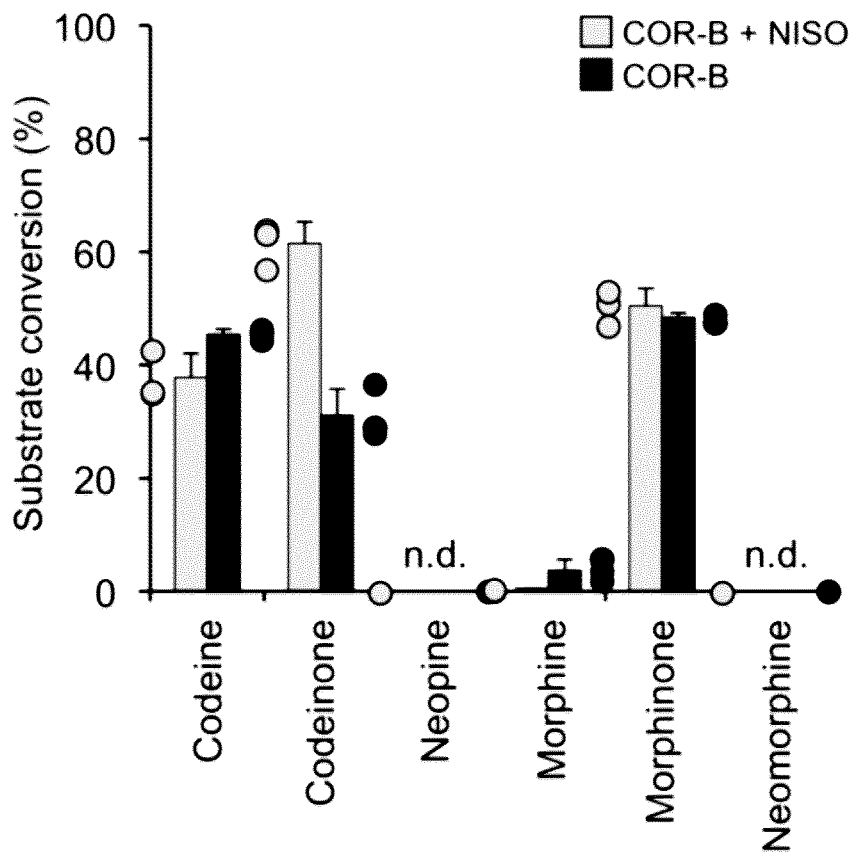
FIG. 16 depicts certain experimental results, notably bar graphs obtained in the performance of an experiment evaluating morphinan alkaloid compound production in assays using COR alone, or COR together with NISO. The substrate morphinan alkaloids evaluated are: codeine, neopine, morphine, neomorphine codeinone, and morphinone, and the product alkaloid morphinans evaluated are codeine and morphine as indicated by the legend in FIG. 16. Substrate conversion (FIG. 16A) and product formation (FIG. 16B) are shown.
Figure 16B:
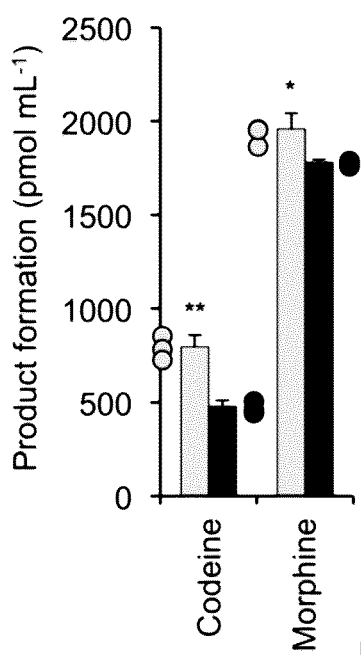

Assay mixtures containing purified recombinant COR-B (~0.1 µg) alone, or purified recombinant COR-B (~0.1 µg) together with purified recombinant NISO (0.196 µg) (1:4 molar ratio), Na-ascorbate cofactor, and 1 mM NADPH, were incubated for 20 mins using one of the following substrates: codeine, neopine, morphine, neopmorphine, codeinone and morphinone. The percentages substrate conversion and products formed were determined. Results are shown in FIG. 16. As can be seen in FIG. 16, in the presence of NISO, codeinone substrate turnover increased almost 2-fold. The products of assays using codeinone and morphinone as a substrate, resulted in a substantial increase in product in the presence of COR-B and NISO together, i.e. codeine and morphine, respectively, when compared to assay mixtures including COR-B alone.

SEQUENCE LISTING

SEQ. ID NO: 1
ATGTACAGCTCATAATGTCACAATATCAGCTGATTCTTTTTCTATATAAAC
TCGTTATACCAACATGGACTCAGTATCAGCTGCTCTAGTATTTCATAGTTC
CATATACTTGTGTGCAATGGCTCATCATGGTGTTTCAGGTCTAGTTGGGAA
AATTGTAACTGAATTGGAGGTGAATTGTAATGCCGACGAATTTTATAAGAT
TTTGAAGCGCGATGAAGATGTTCCACGGGCAGTTTCTGATCTTTTCCCTCC
CGTCAAAATTGCCAAAGGAGATGGACTTGTTTCTGGTTGTATCAAGGAATG
GGACTGTGTTCTTGATGGTAAGGCGATGAGCGGCAAGGAGGAAACAACACA
CAACGATGAAACGAGGACTTTGCGTCACCGTGAATTGGAAGGAGACTTGAT
GAAGGATTACAAGAAGTTTGATTCCATAATTGAAGTTAATCCAAAACCAAA
TGGACATGGAAGCATTGTGACGTGGTCAATTGAGTATGAGAAAATGAACGA
AGATTCTCCGGCTCCCTTTGCTTATCTAGCTTCCTTCCATCAGAACGTTGT
GGAAGTTGATTCTCACCTCTGCCTTTCTGAATAAGATGCAAGTACATGAAC
ACGACTTTAGTGTTCGATGTACGTCAGTATATGTTGTTTAAATGTTCTTCT
TGCGGTATGCCTATGTCTACGTGATCAAGTTCAGTGTTCGTACACGTGAGC
TTTGTGGTTTTGTGGTTACCTAT

SEQ. ID NO: 2
MDSVSAALVFHSSIYLCAMAHHGVSGLVGKIVTELEVNCNADEFYKILKRD
EDVPRAVSDLFPPVKIAKGDGLVSGCIKEWDCVLDGKAMSGKEETTHNDET
RTLRHRELEGDLMKDYKKFDSIIEVNPKPNGHGSIVTWSIEYEKMNEDSPA
PFAYLASFHQNVVEVDSHLCLSE

SEQ. ID NO: 3
ATGGAGAGTAATGGTGTACCTATGATCACTCTCAGTTCCGGCATTCGGATG
CCTGCTTTAGGTATGGGAACAGCTGAAACAATGGTAAAAGGAACAGAAAGA
GAGAAATTGGCGTTTTTGAAAGCGATAGAGGTCGGTTACAGACACTTCGAT
ACAGCTGCTGCATACCAAAGTGAAGAGTGTCTTGGTGAAGCTATAGCTGAA
GCACTTCAACTTGGTCTAATAAAATCTCGAGATGAACTCTTCATCACTTCC
AAGCTCTGGTGCGCTGATGCTCACGCTGATCTTGTCCTCCCTGCTCTTCAG
AATTCTCTGAGGAATCTTAAATTGGACTATCTTGATCTATATTTGATACAC
CATCCGGTAAGCTTGAAGCCAGGGAAGTTTGTTAACGAAATACCAAAGGAT
CATATCCTTCCAATGGACTACAAATCTGTATGGGCAGCCATGGAAGAGTGT
CAGACCCTTGGCTTCACTAGGGCAATCGGGGTCTGTAATTTCTCATGCAAA
AAGCTTCAAGAGTTGATGGCAGCAGCCAAGATCCCTCCAGTTGTGAATCAA
GTGGAGATGAGCCCGACTTTACATCAAAAAAATCTGAGGGAATATTGCAAG
GCCAATAATATCATGATCACTGCACACTCGGTTTTGGGAGCCATATGTGCT
CCATGGGGCAGCAATGCAGTTATGGATTCTAAGGTGCTTCACCAGATTGCT
GTGGCAAGAGGAAAATCTGTTGCCCAGGTTAGTATGAGATGGGTTTACCAG
CAAGGCGCGAGTCTAGTGGTGAAAAGTTTCAATGAAGGGAGGATGAAGGAA
AACCTTAAGATATTTGATTGGGAACTAACGGCAGAGAATATGGAAAAGATC
AGTGAGATTCCGCAATCTAGAACAAGCTCTGCTGATTTCTTGTTATCACCG
ACTGGACCTTTCAAAACTGAAGAAGAGTTCTGGGATGAGAAGGATTGA

SEQ. ID NO: 4
MESNGVPMITLSSGIRMPALGMGTAETMVKGTEREKLAFLKAIEVGYRHFD
TAAAYQSEECLGEAIAEALQLGLIKSRDELFITSKLWCADAHADLVLPALQ
NSLRNLKLDYLDLYLIHHPVSLKPGKFVNEIPKDHILPMDYKSVWAAMEEC
QTLGFTRAIGVCNFSCKKLQELMAAAKIPPVVNQVEMSPTLHQKNLREYCK
ANNIMITAHSVLGAICAPWGSNAVMDSKVLHQIAVARGKSVAQVSMRWVYQ
QGASLVVKSFNEGRMKENLKIFDWELTAENMEKISEIPQSRTSSADFLLSP
TGPFKTEEEFWDEKD

SEQ. ID NO: 5
ATGGAGAAAGCAAAACTTATGAAGCTAGGTAATGGTATGGAAATACCAAGT
GTTCAAGAATTGGCTAAACTCACGCTTGCCGAAATTCCATCTCGATACGTA
TGCGCCAATGAAAACCTTTTGTTGCCTATGGGTGCATCTGTCATAAATGAT
CATGAAACCATTCCTGTCATCGATATAGAAAATTTATTATCTCCAGAACCA
ATAATCGGAAAGTTAGAATTAGATAGGCTTCATTTTGCTTGCAAAGAATGG
GGTTTTTTTCAGGTAGTGAACCATGGAGTCGACGCTTCATTGGTGGATAGT
GTAAAATCAGAAATTCAAGGTTTCTTTAACCTTTCTATGGATGAGAAACT
AAATATGAACAGGAAGATGGAGATGTGGAAGGATTTGGACAAGGCTTTATT
GAATCAGAGGACCAAACACTTGATTGGGCAGATATATTTATGATGTTCACT
CTTCCACTCCATTTAAGGAAGCCTCACTTATTTTCAAAACTCCCAGTGCCT
CTCAGGGAGACAATCGAATCCTACTCATCAGAAATGAAAAAGTTATCCATG
GTTCTCTTTAATAAGATGGAAAAAGCTCTACAAGTACAAGCAGCCGAGATT
AAGGGTATGTCAGAGGTGTTTATAGATGGGACACAAGCAATGAGGATGAAC

-continued

```
TATTATCCCCCTTGTCCTCAACCAAATCTCGCCATCGGTCTTACGTCGCAC
TCGGATTTTGGCGGTTTGACAATCCTCCTTCAAATCAACGAAGTGGAAGGA
TTACAGATAAAAGAGAGGGGACATGGATTTCAGTCAAACCTCTACCTAAT
GCGTTCGTAGTGAATGTTGGAGATATTTTGGAGATAATGACTAATGAATT
TACCATAGTGTCGATCACCGGGCAGTAGTAAACTCAACAAATGAGAGGCTC
TCAATCGCAACATTTCATGACCCTAGTCTAGAGTCGGTAATAGGCCCAATA
TCAAGCTTGATTACTCCAGAGACACCTGCTTTGTTTAAAAGTGGATCTACA
TATGGGGATCTTGTGGAGGAATGTAAAACAAGGAAGCTCGATGGAAAATCA
TTTCTTGACTCCATGAGGATTTGA
```

SEQ. ID NO: 6
```
MEKAKLMKLGNGMEIPSVQELAKLTLAEIPSRYVCANENLLLPMGASVIND
HETIPVIDIENLLSPEPIIGKLELDRLHFACKEWGFFQVVNHGVDASLVDS
VKSEIQGFFNLSMDEKTKYEQEDGDVEGFGQFIESEDQTLDWADIFMMFT
LPLHLRKPHLFSKLPVPLRETIESYSSEMKKLSMVLFNKMEKALQVQAAEI
KGMSEVFIDGTQAMRMNYYPPCPQPNLAIGLTSHSDFGGLTILLQINEVEG
LQIKREGTWISVKPLPNAFVVNVGDILEIMTNGIYHSVDHRAVVNSTNERL
SIATFHDPSLESVIGPISSLITPETPALFKSGSTYGDLVEECKTRKLDGKS
FLDSMRI
```

SEQ. ID NO: 7
```
ATGGAGACACCAATACTTATCAAGCTAGGCAATGGTTTGTCAATACCAAGT
GTTCAGGAATTGGCTAAACTCACGCTTGCAGAAATTCCATCTCGATACACA
TGCACCGGTGAAAGCCCGTTGAATAATATTGGTGCGTCTGTAACAGATGAT
GAAACAGTTCCTGTCATCGATTTGCAAAATTTACTATCTCCAGAACCCGTA
GTTGGAAAGTTAGAATTGGATAAGCTTCATTCTGCTTGCAAAGAATGGGGT
TTCTTTCAGCTGGTTAACCATGGAGTCGACGCTTTACTGATGGACAATATA
AAATCAGAAATTAAAGGTTTCTTTAACCTTCCAATGAATGAGAAAACTAAA
TACGGACAGCAAGATGGAGATTTTGAAGGATTTGGACAACCCTATATTGAA
TCGGAGGACCAAAGACTTGATTGGACTGAAGTGTTTAGCATGTTAAGTCTT
CCTCTCCATTTAAGGAAGCCTCATTTGTTTCCAGAACTCCCTCTGCCTTTC
AGGGAGACACTGGAATCCTACCTATCAAAAATGAAAAAACTATCAACGGTT
GTCTTTGAGATGTTGGAAAAATCTCTACAATTAGTTGAGATTAAAGGTATG
ACAGACTTATTTGAAGATGGGTTGCAAACAATGAGGATGAACTATTATCCT
CCTTGTCCTCGACCAGAGCTTGTACTTGGTCTTACGTCACACTCGGATTTT
AGCGGTTTGACAATTCTCCTTCAACTTAATGAAGTTGAAGGATTACAAATA
AGAAAAGAAGAGAGGTGGATTTCAATCAAACCTCTACCTGATGCGTTCATA
GTGAATGTTGGAGACATTTTGGAGATAATGACTAATGGGATTTACCGTAGC
GTCGAGCACCGGGCAGTAGTAAACTCAACAAAGGAGAGGCTCTCAATCGCG
ACATTTCATGACTCTAAACTAGAGTCAGAAATAGGCCCAATTTCGAGCTTG
GTCACACCAGAGACACCTGCTTTGTTCAAAAGAGGTAGGTATGAGGATATT
TTGAAGGAAAATCTTTCAAGGAAGCTTGATGGAAAATCATTTCTCGACTAC
ATGAGGATGTGA
```

SEQ. ID NO: 8
```
METPILIKLGNGLSIPSVQELAKLTLAEIPSRYTCTGESPLNNIGASVTDD
ETVPVIDLQNLLSPEPVVGKLELDKLHSACKEWGFFQLVNHGVDALLMDNI
KSEIKGFFNLPMNEKTKYGQQDGDFEGFGQPYIESEDQRLDWTEVFSMLSL
PLHLRKPHLFPELPLPFRETLESYLSKMKKLSTVVFEMLEKSLQLVEIKGM
TDLFEDGLQTMRMNYYPPCPRPELVLGLTSHSDFSGLTILLQLNEVEGLQI
RKEERWISIKPLPDAFIVNVGDILEIMTNGIYRSVEHRAVVNSTKERLSIA
TFHDSKLESEIGPISSLVTPETPALFKRGRYEDILKENLSRKLDGKSFLDY
MRM
```

SEQ. ID NO: 9
```
ATGGACTCAGTATCAGCTGCTCTAGTATTTCATAGTTCCATATACTTGTGT
GCAATGGCTCATCATGGTGTTTCAGGTCTAGTTGGGAAAATTGTAACTGAA
TTGGAGGTGAATTGTAATGCCGACGAATTTTATAAGATTTTGAAGCGCGAT
GAAGATGTTCCACGGGCAGTTTCTGATCTTTTCCCTCCCGTCAAAATTGCC
AAAGGAGATGGACTTGTTTCTGGTTGTATCAAGGAATGGGACTGTGTTCTT
GATGGTAAGGCGATGAGCGGCAAGGAGGAAACAACACACAACGATGAAACG
AGGACTTTGCGTCACCGTGAATTGGAAGGAGACTTGATGAAGGATTACAAG
AAGTTTGATTCCATAATTGAAGTTAATCCAAAACCAAATGGACATGGAAGC
ATTGTGACGTGGTCAATTGAGTATGAGAAAATGAACGAAGATTCTCCGGCT
CCCTTTGCTTATCTAGCTTCCTTCCATCAGAACGTTGTGGAAGTTGATTCT
CACCTCTGCCTTTCTGAATAA
```

SEQ. ID NO: 10
```
ATGGCTCATCACGGTGTTTCAGGTCTAGTTGGGAAACTTGTAACTCAATTA
GAGGTCAATTGTGATGCTGACGAATTTTATAAAATTTGGAAGCACCATGAA
GAAGTTCCAAAGGCAGTTTCTCATTTTTTCCCTGCCGTCAAAGTTGTCAAA
GGAGATGGACTTGTTTCTGGTTGTATCAAGGAATGGCACTATATCCTCGAG
GGTAAGGCGATGAGCGCAATGGAGGAAACGACACACAATGATGAAACAAGG
ACTTTACATCACCAGGTAGTTGAAGGAGAAGTGATGAAGGATTACAAGGCG
ATTGCTTCCATAATTCAAGTTAATCCAAATCCAAATGGACATGGAAGCATT
GTGACGTGGTCAATTGAGTATGAGAAAATGAACGAAGATTCTCCAACTCCC
TTTGCTTATCTTGAATTCTTCCATCAGAACATAATCGATATGAATTCTCAC
CTCTACGTAGGCTCTGATTCTCACCTCCACGTTGATGAATAA
```

SEQ. ID NO: 11
```
MAHHGVSGLVGKLVTQLEVNCDADEFYKIWKHHEEVPKAVSHFFPAVKVVK
GDGLVSGCIKEWHYILEGKAMSAMEETTHNDETRTLHHQVVEGEVMKDYKA
IASIIQVNPNPNGHGSIVTWSIEYEKMNEDSPTPFAYLEFFHQNIIDMNSH
LYVGSDSHLHVDE
```

SEQ. ID NO: 12
```
ATGGCGCACCACGGTGTGAGCGGCCTGGTTGGCAAGATCGTGACCGAGCTG
GAAGTTAACTGCAACGCGGATGAGTTCTATAAGATTCTGAAACGTGACGAA
GATGTTCCGCGTGCGGTGAGCGACCTGTTTCCGCCGGTTAAGATCGCGAAA
GGTGATGGCCTGGTGAGCGGCTGCATTAAAGAGTGGGACTGCGTGCTGGAT
GGCAAGGCGATGAGCGGTAAAGAGGAAACCACCCACAACGACGAAACCCGT
```

```
ACCCTGCGTCACCGTGAGCTGGAAGGTGACCTGATGAAGGATTACAAGAAA
TTCGATAGCATCATTGAGGTTAACCCGAAACCGAACGGTCACGGCAGCATC
GTGACCTGGAGCATTGAGTACGAAAAGATGAACGAAGACAGCCCGGCGCCG
TTCGCGTATCTGGCGAGCTTTCACCAGAACGTGGTTGAGGTTGATAGCCAC
CTGTGCCTGAGCGAATAA
                                    SEQ. ID NO: 13
CGAGGAAGGCCTCCACGAAGGCGATCAGGTCGAGGTTGGAATCCCGGGAGA
CGGTGGGGAAGCCCACCAGGCGGTCGAGCATCTCGGCGGCGGTCATGGCGC
GCTCCTTGGTCACGTTTCGGGAAATCCTATCACGCCCGCGGGGCAGGCCGG
CGGCCTGGGCGTCATAGCCCCAGACTATCCGGTCGATGCCGTCACTCTTTT
TGACAGCAGTCATTAACAGGCTTAAGATGTCGGGCGACGACGGATACCCGT
CCATTCACTCTTCATCTGGAGGCGTATTGATGCCGGATACATCCTTCTCCA
ACCCCGGGCTCTTCACCCCGCTGCAGCTGGGCAGCCTCAGCCTGCCCAACC
GCGTGATCATGGCGCCGCTGACCCGCTCGCGCACGCCGGACAGCGTTCCCG
GCAGGTTGCAGCAGATCTACTATGGCCAGCGCGCCAGCGCCGGGCTGATCA
TCAGCGAGGCCACCAATATCTCGCCCACCGCCCGCGGCTACGTCTACACGC
CGGGGATCTGGACCGACGCGCAGGAAGCCGGCTGGAAGGGCGTCGTCGAGG
CGGTGCATGCCAAGGGCGGGCGCATCGCCCTGCAGCTGTGGCACGTCGGCC
GTGTCTCCCACGAGCTGGTGCAGCCCGACGGCCAGCAGCCCGTGGCACCGA
GCGCCCTCAAGGCCGAGGGGGCGGAATGCTTCGTCGAGTTCGAGGACGGCA
CGGCGGGGCTGCACCCCACCAGCACGCCGCGGGCGCTTGAGACCGACGAGA
TCCCCGGCATCGTCGAGGACTACCGCCAGGCTGCGCAGCGCGCCAAGCGTG
CCGGCTTCGACATGGTCGAGGTCCACGCCGCCAACGCCTGCCTGCCCAACC
AGTTCCTCGCCACCGGCACCAACCGGCGCACCGACCAGTACGGCGGCTCCA
TCGAGAACCGGGCGCGCTTCCCGCTGGAGGTGGTCGACGCCGTGGCCGAGG
TGTTCGGGCCCGAGCGGGTCGGCATCCGCCTGACCCCCTTCCTCGAGCTCT
TCGGCCTCACCGACGACGAGCCCGAGGCGATGGCCTTCTACCTGGCCGGCG
AGCTCGACCGCCGCGGCCTGGCCTACCTCCACTTCAACGAGCCCGACTGGA
TCGGTGGCGATATCACCTACCCCGAAGGCTTCCGGGAGCAGATGCGCCAGC
GCTTCAAGGGTGGGCTGATCTACTGCGGCAACTACGATGCCGGGCGCGCCC
AGGCCCGCCTGGATGACAACACCGCCGACGCCGTGGCCTTCGGCCGCCCCT
TCATCGCCAACCCCGATCTGCCCGAGCGCTTCCGCCTGGGGGCCGCCCTCA
ACGAGCCCGACCCCAGCACCTTCTACGGCGGCGCCGAGGTCGGCTACACCG
ACTACCCCTTCCTCGACAACGGCCACGACCGGCTCGGCTGAGTCAGCGTCC
GCCCCTGGAAGCATCAGCAAGCCCGGCCAGCGTGCCGGGCTTGTGGCGTGA
TGGGGAGGGTGGTGCGGGGCATCGTCGGTGATTGGCGCACATCAACACCGC
GGCGTCAGATCCACAGAACGCATTCCGAGGGACCGCC
                                    SEQ. ID NO: 14
TTGAAGCGCGATGAAGATGTTCCACGGGCAGTTTCTGATCTTTTCCCTCCC
GTCAAAATTGCCA
                                    SEQ. ID NO: 15
TGGGACTGTGTTCTTGATGGTAAGGCGATGAGCGGCAAGGAGGAAACAACA
CACAACGATGAAACGAGGACTTTGCGTCACCGTGAATTG
                                    SEQ. ID NO: 16
GACTTGATGAAGGATTACAAGAAGTTTGATTCCATAATTGAAGTTAATCCA
AAACC
                                    SEQ. ID NO: 17
GCTCCCTTTGCTTATCTAGCTTCCTTCCATCAGAACGTTGTGGAAGTTGAT
TCTCACCTCTGCCTTTCTGAATAA
                                    SEQ. ID NO: 18
LKRDEDVPRAVSDLFPPVKIA
                                    SEQ. ID NO: 19
DCVLDGKAMSGKEETTHNDETRTLRHREL
                                    SEQ. ID NO: 20
DLMKDYKKFDSIIEVNPK
                                    SEQ. ID NO: 21
APFAYLASFHQNVVEVDSHLCLSE
                                    SEQ. ID NO: 22
MPDTSFSNPGLFTPLQLGSLSLPNRVIMAPLTRSRTPDSVPGRLQQIYYGQ
RASAGLIISEATNISPTARGYVYTPGIWTDAQEAGWKGVVEAVHAKGGRIA
LQLWHVGRVSHELVQPDGQQPVAPSALKAEGAECFVEFEDGTAGLHPTSTP
RALETDEIPGIVEDYRQAAQRAKRAGFDMVEVHAANACLPNQFLATGTNRR
TDQYGGSIENRARFPLEVVDAVAEVFGPERVGIRLTPFLELFGLTDDEPEA
MAFYLAGELDRRGLAYLHFNEPDWIGGDITYPEGFREQMRQRFKGGLIYCG
NYDAGRAQARLDDNTADAVAFGRPPFIANPDLPERFRLGAALNEPDPSTFYG
GAEVGYTDYPFLDNGHDRLG
                                    SEQ. ID NO: 23
TGTTTCGTCATCAAAGGTCGTTTGCTCCTTAACAATCATCCTAATACCCAG
CTAAGACAATAATCAGTATCAACTATCAGAAATGGCTCATGCTCATGGTAT
TTCAGGTCTAGTTGGGAAACTTATTACTGAATCGGAGGTTAACTGCAACGC
TGACAAGTTTTACCAAATGTTTAAGCACGATGAAAATATTACAAATATAAT
TCCTCATATCTATACTAGTTTCAAGGTTGTCGAGGGAGATGGACTTATTTC
TGGTTGTACCAAGGAATGGGGCTATCTTTCTGAGGGCAAAGCAAGGATTGT
TAAGGAGCAAACGACCTTTGATGACGAAACAAGGACGATACATCATTGCGC
AAAAGCAGGAGACATGATGAATGATTACAAGAAGTTCGTTCTAACACTTGT
AGTTAATCCAAAGGCTCATGGACAAGGAAGCACAGTCAAGTGGATTATAGA
TTATGAGAAGATAAATGAGGATTCTCCAGTTCCTTTTGCTTATCTATCTCT
GTGCATTAAGATCACTGAAGGTCTGAACTCTCACATCTACGCTTCCGAATA
GGTTATCAATGGATATGTCCACCGATATGTTTGTGTATCGGCGAATATCAG
GACTCAGTATATATGGTGTGTGCTAATGGAGTTTCTACTAGATCTCCTATG
ATCGACCTAATAAATGCGTACGTACTTGCATGTATGTGTGGTGTGTTTCAT
TTCGTTTCGTTTTTCATCTACTTTCTGTAATTTCTA
```

SEQ. ID NO: 24
MAHAHGISGLVGKLITESEVNCNADKFYQMFKHDENITNIIPHIYTSFKVV
EGDGLISGCTKEWGYLSEGKARIVKEQTTFDDETRTIHHCAKAGDMMNDYK
KFVLTLVVNPKAHGQGSTVKWIIDYEKINEDSPVPFAYLSLCIKITEGLNS
HIYASE

SEQ. ID NO: 25
TGTGCGAGGATACATAATTTCTATATAAACTCATTCAACTAGCTAATAATT
CATCAAAATTCAATTGAATTTATATGTGTCATTGTTTTTCAAACTTACTTA
TATATCAAGGAAAACAATCAATATCAATTACCAAAAATGGCTCAACATCAT
ACCATTTCAGGTCTTATTGGGAAGCTTGTGACCGAATCAGAAGTTAATTGC
GATGCTGAAAAATATTACAAAATAATTAAGCACCACGAAGATGTACCTAAT
GCAACCCCTTATGTTTCCGATGTCAAAGTTACTGAAGGACATGGTACCACT
TCGGGTTGTGTCAAGCAATGGAACTTTGTTGTTGCGGGTCGAAACGAATAT
GTCCTTGAAAAACAACATACAATGATGAAACAAGGACAATATGTCACAGT
GACTTTGAAGGAGACCTGATGAAGAAATACAAGAAGTTTGATGCAATCCTT
GTAGTTAAGCCAAAGGATAATGGACATGGTAGTAATGTGAGATGGACTATT
GAATATGAGAAGAATAACGAGGATTCTCCGGTTCCAATTGATTATCTAGGT
TTCTTCCAATCGTTAATCGATGACTTGAACTCTCATCTTTGCTCCTCTTAA
TAATTTGGATTGATGATACGTATCAACACCTTCTACGTACAGTTCGATCGC
TTATGTGGGTATGTATTTGTGTGATAATAAATAGTATGTGGATTTTTCACA
ATATATACAATAATGTGCATACATGCACGTGTGATTTGTCTTATTTATTTT
CATTATCATTTTTTGTCATGTTTTAAGGCGTATAATATG

SEQ. ID NO: 26
MAQHHTISGLIGKLVTESEVNCDAEKYYKIIKHHEDVPNATPYVSDVKVTE
GHGTTSGCVKQWNFVVAGRNEYVLEKTTYNDETRTICHSDFEGDLMKKYKK
FDAILVVKPKDNGHGSNVRWTIEYEKNNEDSPVPIDYLGFFQSLIDDLNSH
LCSS

SEQ. ID NO: 27
CTTCCACACACTCTTGTGCAAACTTCTATACTACATATCTACAATCAACAA
CTATATCAATGGCTAGTTATGATTATGGTCTTTCCGGTCTAATTGGGAAAT
TTTATAATTCAATTGGAGATCAATAGCGATGCTGACAATTTTTATGAAATCT
ATAAGCATTGCAAAGATGTTCCTAAGGCAGTTCCTCATCTTTTCACTGGTG
TTAAAGTTACCAAAGGAGATGAACTCGTTTCTGGTTGTATCAAGGAATGGA
ACTATGTTCTTGAGGGTAAGGCGATGACCGCTGTGGAGGAAACAACAATTG
ACGATGCAACAAGGACCTTGACACACCACGTAATTGAAGGAGACGTGATGA
AGGATTACAAGAAGTTCGATGTGATTATTGAAGCTAATCCGAAGCCTAGTG
GACAAGGAACCATTGGAGGAAGCATTGTGACTGTGTCTATTGTATATGACA
GAATGAATGCGAAGTCTCCAGCTCCCTTCGATTATTACAAATTCTATTATC
AGAACATAGTAGATATGGATGCTCACATCTCCACTTCTTAGTAAACTATCT
TAATCTCCGTGTTGGGTGTGCGTATGCATGTGCATATGTACGTCAGTACTC
GTTGATCAATTTGTATGCGTTACTTCACGAGATCTATTGCATCTCTATAAC
TATGTATCATTTTAAATAAATGGAGTAAGTTATTTAAAATAAAAAAAA

SEQ. ID NO: 28
MASYDYGLSGLIGKFIIQLEINSDADNFYEIYKHCKDVPKAVPHLFTGVKV
TKGDELVSGCIKEWNYVLEGKAMTAVEETTIDDATRTLTHHVIEGDVMKDY
KKFDVIIEANPKPSGQGTIGGSIVTVSIVYDRMNAKSPAPFDYYKFYYQNI
VDMDAHISTS

SEQ. ID NO: 29
ATTGATGATGGTTGATACTGGTTCATTCACAATCATCCTAATATTAATTAG
TTAAGGCAAGAACCAGTATCAACCATCATCAATGGCCCATCAACATACAAT
TTCAGGTCTTGTGGGAAAACTTATTACTGAATCGGAGGTTAACTGCAATGC
CGACAAGTATTACCAAATATTTAAGCACCATGAAGACCTTCCAAGCGCAAT
CCCTCATATTTACACTAGCGTCAAAGCTGTCGAGGGACATGGAACTACTTC
TGGATGTGTCAAGGAGTGGTGCTATATTCTTGAGGGGAAACCACTTACAGT
TAAGGAGAAAACAACGTACAATGATGAAACAAGAACGATAAATCATAATGG
AATAGAAGGAGGCATGATGACTGATTACAAGAAGTTCGTTGCAACACTTGT
AGTTAAGCCAAAAGCTAATGGGCAAGGAAGCATCGTGACATGGATAGTGGA
TTATGAGAAGATTAATGAGGATTCTCCAGTTCCTTTCGACTATCTAGCTTT
CTTCCAACAAAACATCGAAGACTTGAACTCTCACCTCTGTGCTTCTGATTA
AATTATCAATGGGTATGTCCATATGCAACGATGAACATCAGTGTTCTCTGT
ATGATAATAAAGTCTATATGTGGA

SEQ. ID NO: 30
MAHQHTISGLVGKLITESEVNCNADKYYQIFKHHEDLPSAIPHIYTSVKAV
EGHGTTSGCVKEWCYILEGKPLTVKEKTTYNDETRTINHNGIEGGMMTDYK
KFVATLVVKPKANGQGSIVTWIVDYEKINEDSPVPFDYLAFFQQNIEDLNS
HLCASD

SEQ. ID NO: 31
GCTTTATTTATATGCCGGCCCTCAATAACCAAAGACACTCGATGCATCTGT
GCAGTACATATATATACGTACTGCATTATTAAGACACACAAACCAACAGCT
TCATTTGTCTCTCGAGTAGTAACAATCAATATCATCAATTTTCATCCATGG
CTCATCCCCATCCTATTTCAGGTCTAGTTGGGAAACTAGTGACTGAATTGG
AGGTTAACTGCGACGCTGACAAGTATTACAAAATTTTTAAGCACCATGAAG
ATGTTCCAAAAGCAGTACCTCATATGTACACTAGCGTCAAAGTTGTCGAGG
GACATGGAATTACTTCTGGTTGTGTCAAGGAATGGGGTTATCTTCTTGAGG
GAAAAGAACTGATTGTCAAGGAAACAACAACATACACTGATGAAACAAGGA
CGATACATCATAGCGCAGTAGGAGGACACATGACGAAGATTTACAAGAAGT
TTGATGCAACGCTTGTAGTCAATCCAAAGCCTAGTGGCCATGGAAGCACGG
TGAGTTGGACTATTGATTATGAGAAAATTAACGAGGATTCTCCCGTTCCTA
TTCCATATCTAGCTTTCTTCCATAAGCTCATCGAGGACTTGAACTCTCACC
TCTGCGCTTCTGATTAAAGAAATTATTGATTTATTGTTCTCGATGGACAAT
TTCAGCTGTTGGTTTGTGTGTGTTAATAATGCAGTACGTATATATATGTAC
TGCACAGATGCATCGAGTGCTTTTGGTTATTGAGGGCCGGCATATAAATAA
AGCCACTCCTACTCAAGTATTT

SEQ. ID NO: 32
MAHPHPISGLVGKLVTELEVNCDADKYYKIFKHHEDVPKAVPHMYTSVKVV
EGHGITSGCVKEWGYLLEGKELIVKETTTYTDETRTIHHSAVGGHMTKIYK
KFDATLVVNPKPSGHGSTVSWTIDYEKINEDSPVPIPYLAFFHKLIEDLNS
HLCASD

SEQ. ID NO: 33
TTTGACCGGCAGTTTATGATAATCTCACCAGCAGTAGATACTTATGATAGG
TAATTGGCCACTAAACAAATGCTTGTTTTTCTATATAAACTAGATCAACTT
TCATTGAAATTTATCATCAACTGCTCCAGCAATTATAGTTCTCTACAAACT
TCAATATATAGGGCAACAATCATCAACCATCTATGGCGCATCATGGTGTTT
CAGGTCTAGTTGGGAAACTTGTAACTGAATTGGAGGTCCATTGCAATGCTG
ACGCATACTATAAAATCTTTAAGCACCAAGAAGATGTACCAAAGGCAATGC
CTCATCTTTACACTGGCGGGAAAGTTATCAGTGGAGATGCAACCCGTTCTG
GTTGTATCAAGGAATGGAACTACATTCTTGAGGGTAAGGCGCTGATCGCAG
TGGAGGAAACAACACATGACGATGAAACAAGGACCTTAACACACCGCATAA
CTGGAGGAGACTTGACAAAGGATTACAAAAAGTTCGTTAAGATCGTTGAAG
TTAATCCAAAGCCTAATGGACATGGAAGCATTGTGACTGTATCCCTTGTGT
ATGAGAAAATGAACGAGGGTTCTCCAACTCCCTTTAATTATCTACAATTTG
TCCATCAGACCATTGTAGGCTTGAATTCTCACATCTGCGCTTCTTAGTAAA
ATACATCCGAACTTCAGCGTTGGGTTTAAGTATGCACGTACGATCGTCGGT
ACTTGTTGTTTAATTAGTTGTACTGTACGTTATTCCTACACACTGCACTAT
CATGCCTATGTATGTTTGATTAAATAAGACTATGGAACTATGGGATTTATC
ATATGCGATGATCCTTTTGAATAAATCAAATAAGTCATTTAAAATGTGTTT
TTTTTTTTCTCTTTTCT

SEQ. ID NO: 34
MAHHGVSGLVGKLVTELEVHCNADAYYKIFKHQEDVPKAMPHLYTGGKVIS
GDATRSGCIKEWNYILEGKALIAVEETTHDDETRTLTHRITGGDLTKDYKK
FVKIVEVNPKPNGHGSIVTVSLVYEKMNEGSPTPFNYLQFVHQTIVGLNSH
ICAS

SEQ. ID NO: 35
GCATCACAAATTAAACCAACGAGATCAGCGACTACACTATAATATACTGCA
ATTATTAGGAAAATGAGGTACGAGTTTATAAACGAGTTTGATGCACATGCA
TCAGCAGACGATGTTTGGGGAGGAATCTATGGCTCCATTGATTACCCTAAA
CTAGTGGTTCAATTACTTCCAACTGTCCTCGAAAAGAAGGAAATCTTGGAA
GGCGATGGTCATAATGTTGGTACTGTTCTGCATGTTGTGTACCTTCCAGGA
TTTGTTCCGCGGACGTACAACGAGAAGATTGTAACGATGGATCACAAAAAA
CGTTACAAGGAAGTACAAATGGTTGAAGGAGGATACTTGGATATGGGATTT
ACATATGTCATGGTAATTCATGAAGTACTAGCAAAAGAATGTAATTCTTGT
ATCATTAGATCAATTGTTAAGTGTGAAGTCAAGGATGAATTTGCTGCAAAT
GTTTCTAATATTCGCAACACCTTTGATGGATATGTCGCCTTAGCCCGAGCC
GTTCCGGAATATATTGCGAAGCAGCACGCAACATCAGCAGCTAATTAACTT
GCTGCCGCAGTTAATAAATGGATTTTCGATGGTCTAAATAATATGGAACTG
GATAAAGTACCTAGGACTGAGATTACTGTTTCCTTCCTATGTTATTCCTCT
TGTGATCTTCTTTTCTCTCTTTCTATGTTTTTGTGCTTTATCTTTT

SEQ. ID NO: 36
MRYEFINEFDAHASADDVWGGIYGSIDYPKLVVQLLPTVLEKKEILEGDGH
NVGTVLHVVYLPGFVPRTYNEKIVTMDHKKRYKEVQMVEGGYLDMGFTYVM
VIHEVLAKECNSCIIRSIVKCEVKDEFAANVSNIRNTFDGYVALARAVPEY
IAKQHATSAAN

SEQ. ID NO: 37
TAGAAAATTTAGGGGGGGCTAGTGACCCCACTGACCCCAGTGTAGATTCGC
CACTGATATCAGTTGCTCTAATCTTCCATACTGCCATATATTTCTGTGCAA
ATTTCAGGATAACAATCTTGAACTGTTGATGGCTCATCACGGTGTTTCAGG
TCTAGTTGGGAAACTTGTAACTCAATTAGAGGTCAATTGTGATGCTGACGA
ATTTTATAAAATTTGGAAGCACCATGAAGAAGTTCCAAAGGCAGTTTCTCA
TTTTTTTCCCTGCCGTCAAAGTTGTCAAAGGAGATGGACTTGTTTCTGGTTG
TATCAAGGAATGGCACTATATCCTCGAGGGTAAGGCGATGAGCGCAATGGA
GGAAACGACACACAATGATGAAACAAGGACTTTACATCACCAGGTAGTTGA
AGGAGAAGTGATGAAGGATTACAAGGCGATTGCTTCCATAATTCAAGTTAA
TCCAAATCCAAATGGACATGGAAGCATTGTGACGTGGTCAATTGAGTATGA
GAAAATGAACGAAGATTCTCCAACTCCCTTTGCTTATCTTGAATTCTTCCA
TCAGAACATAATCGATATGAATTCTCACCTCTACGTAGGCTCTGATTCTCA
CCTCCACGTTGATGAATAAAATGTCATTACCGTAAGTACATGAACGCGGCT
TTAGTGTTTGATGTACGTCAGTATGTGCTGTTTGAATTGATCAGTTTCCTG
TGTTATTCTTACTTGAATCAGTTGCTTATGCTAGTCTTGCAGTATGCCTGT
GTCTACGTGCCTGTGTTTCATAATAATAAAGGCTAAGAGCACTTGCAAGTT
ATAATTCTCTTCTTTATATCCCTTTTCCTATGGTGTATTCTGTTTAATCAA
GTTCTGTTTTCTCTAGCACAAGGGTTTCCACAAATTATCTCAGTTACCCTG
AATTATTTTTCTTAATTGCAAATGTAAAAGGTACTAAAAGGAGAATTACT
AGTACCTAGTAGTCGTAACCCAATCAATTGAGCCAAATTTGATGCCTATAA
TATGCGATAATGTAGCTAAGAAAGCTTTCTGAATCAACAGTATATATATAT
TGTTGCGGTGTCAACTCCTACTTCTTTTATTAGAGTTAGTTTATTACCTTA
TTATTTGTTTTCCGTACGTACTTAACATTCAGTTTCCTAGTTTATAAGATT
TCTTCAGTGAGTTGCTTGCTTACCAAGTTTATTCAGCTATATATAGCTCGA
TCCTAGCTTGTAACAGGACAAATTATCAATATAAGAAGTT

SEQ. ID NO: 38
MAHHGVSGLVGKLVTQLEVNCDADEFYKIWKHHEEVPKAVSHFPPAVKVVK
GDGLVSGCIKEWHYILEGKAMSAMEETTHNDETRTLHHQVVEGEVMDYKAI
ASIIQVNPNPNGHGSIVTWSIEYEKMNEDSPTPFAYLEFFHQNIIDMNSHL
YVGSDSHLHVDE

SEQ. ID NO: 39
ACTGTAACGTGCAAGTCCGCATAGTCTTACTTATTCAAACATTTATATAAA
CCCATAGCCCTAAGCATATAGaATCAaTaTCAACTGCTAAGGTCTTCCAAA
ATTCTATATACTTTTTCAGCAACAAACTGTTAATGGCTCATCATGGCGTTT
CTGGTTTAGTTGGGAAACTTGTAACTCAATTGGAGGTCAATTGTGATGCTG

ATAAATTGTATAAAATCTATAAGCACCATGAAGATGTTCCAAAGGCAATTT
CTCATCTTTTCACCGGTGTAAAAGTTCTCGAAGGACATGGACTTCGTTCTG
GCTGTATCAAGGAATGGAAATATATTATTGATGGTAAGGCGTTGACTGCTG
TGGAGGAAACAACCCATGGCGATGAAACAAGGACTTTAAAACATCGCGTCA
TTGATGGAGACTTGATGAAGGATTACAAGAAGTTCGACAAGATCATTGAAG
CTAATCCAAAGCCAAATGGACATGGAAGCATTGTGACTGTCTCTCTTTTGT
ATGAGAAGATAAATGAGGACTCTCCAGCTCCGTTTGATCATCTCAAATTCT
TCCATCAAAACATAGAAGATATGAATTCTCACATCTGCGCTTCAGAGTAAA
ATATCTCATCTTCATTGTTGGGTGTACGTATGCGTTCAGTAAGTCAGTGCT
TGAGAAATTAGTTGTGTGCGTTATTCCAGTCAGTGTTTTGTGTAAGTAGTT
GGAATGTTGGATGCGTTATTCCTACAGTGTGCTATATGCTTAGGGCTATGG
GTTTATATAAATGTTTGAATAAAAGTAAAAAAACTAAAAAGAGACTAGCCA
AAGGCACACAGGGGATAGNAACAAATAAATTTAAA

SEQ. ID NO: 40
MAHHGVSGLVGKLVTQLEVNCDADKLYKIYKHHEDVPKAISHLFTGVKVLE
GHGLRSGCIKEWKYIIDGKALTAVEETTHGDETRTLKHRVIDGDLMKDYKK
FDKIIEANPKPNGHGSIVTVSLLYEKINEDSPAPFDHLKFFHQNIEDMNSH
ICASE

SEQ. ID NO: 41
AGTATTTCATAGTTCCATATACTTGTGTGCAATGGCTCATCATGGTGTTTC
AGGTCTAGTTGGGAAACTTGTTACTCAGCTGGAGGTCAATTGCGATGCAGA
CATATTTTATAAAATCGTTAAGCACCATGAAGAAGTTCCAAACGTAATTCC
TCATTTTTTCACCGGCGTTCAAGTGACCAAAGGAGATGGACTTGTTTCTGG
TTGTATCAAGGAATGGAACTATGTTCTTGAGGGTAAGGCGATGACCGCTGT
GGAGGAAACAACCCACGCCGATGAAACAAGGACCCTAACACACCACATAAC
TGAAGGAGACGCGATGAAAGATTACAAGAAGTTTGATGTGATCGTTGAAAC
TAATCCAAAGCCTAATGGACATGGAAGCGTTGTGACATATTCTATTGTGTA
TGAGAAAATCAATGAGGATTCTCCAGCTCCCTTTGATTATCTAAAATTCTT
CCATCAGAACATAGTAGACATGAGTGCTCACATCTGCTCTTCTGCATAATA
TACCAATGAACTTCAGTGTTGTTGCGTGGACGTATTCACGTGAAAATGAAC
GTCGGTGCTTGCTGTTCAATTTGTGTGCGTTATTCCTTCACTATGATGATG
TCTATGGATGTTTGGTTAAATAAGACTTGTGTGTGGACTATCGGATCTATT
GCATCTCTGCTGATCTTTTTAAATAAAACATACAGTATAAAATATTTAATT
AGTTGCGCCTTGTTAGTCTGTGACTCCCATATCCAAAATCTATTATTGTGA
TTTAAAACTTGCGAACTGATCAAAAATCTATATTGTGCCAAAAATTTAATA
CTTATTGGAAAC

SEQ. ID NO: 42
MAHHGVSGLVGKLVTQLEVNCDADIFYKIVKHHEEVPNVIPHFFTGVQVTK
GDGLVSGCIKEWNYVLEGKAMTAVEETTHADETRTLTHHITEGDAMKDYKK
FDVIVETNPKPNGHGSVVTYSIVYEKINEDSPAPFDYLKFFHQNIVDMSAH
ICSSA

SEQ. ID NO: 43
TTGCCCTAAATACAGCTCATTATCCAGTCACCACCCTTTATCATTCCTGTA
GTTTCTGGTTGTTTCTATATAAACTCGTTCAGCTAAGACTAATTTTCATCG
CAATCACACTCATCCTAATATTCAGCTAAGGAAACCGTAAGTATCAACTTT
TAGCAATGGCTCATACTCGTGGTATTTCAGGTCTAGTTGGGAAACTTGTTA
TGGAAACGGAGGTTAACTGCAACGCTGACAAGTATTACCAAATATATAAGC
ACCATGAAGATCTTCCAAGCGCAATCCCTCATATTGTCACTAGCGCCAAAG
CTGTTGAGGGACATGGAACTACTTCTGGTTGCGTCAAGGAGTGGGGCTATA
TGCATGAGGGTAAAACACTTACTTGCAAGGAGAAAACTACCTATAACGATG
AAACAAGGACGATATGTCATAGCATATCTGAAGGAGACTTGATGAATGATT
ACAAGAAGTTCGATGCAACACTTGTCGTTGATCCAAAGGATAATGGACATG
GAAGCATTGTGAAGTATATTTTAGATTATGAGAAGATAAATGAGGATTCTC
CGGTTCCTATTCATTATCTAGCTCTGTGCAATCAAGCCACCGAAGACTTGA
ACACTTACCTTTGTGCTTCTGTCTAAGTTATCAATGGATATCTCCGCCGAA
TAAAATATGCAAGTATGAATACCACTGTTCTACTTCTATCAGTGGTATCTAA
TAATAAAGTCTATATGTGGAATTTCCACTAGACCTATTGTCTATAATAAAT
GCTTCCATACTTGTACGTACCTGTTGTTTTCTTCATTTCTTTTTGTTATGG
AGTACTGTTTTCGTCTACTATCTTTTATTTTTACTGAAAATCAAGGCGTA
ATAATA

SEQ. ID NO: 44
MAHTRGISGLVGKLVMETEVNCNADKYYQIYKHHEDLPSAIPHIVTSAKAV
EGHGTTSGCVKEWGYMHEGKTLTCKEKTTYNDETRTICHSISEGDLMNDYK
KFDATLVVDPKDNGHGSIVKYILDYEKINEDSPVPIHYLALCNQATEDLNT
YLCASV

SEQ. ID NO: 45
GTTCGATATATATACTTCTGTTCATACTTCAGGGCAACAATCGTCAACTGT
CAATGGCTCGTCACGGAGGTTCAGGTCTAGTAGGGAAACTTGTAACTGAAC
TGGAGGTCTACTGCGATGCTGACAAATATTATAAAATCTGGAAGCACCACG
AAGATGTTCCGAAGGCAATGCCTCATATGTTCACTGGTGTCCAACCTATCA
AAGGAGATGGAATCTGTTCCGGCAGCATCAAGGAATGGAACTATATCATTG
AAGGTAAGGCAATGAGAGCTATGGAGGAATCAACACATAACGATGAAACGA
GAACAATAAGTCACCGTGTTAGAAGGAGACCTGCTGAAGGATTACAAGA
AGTTTGAATCGATAAATGAAATCAATCCTAAGCCTAACGGAAATGGATGCG
TCGTGACATGGACTATTGCATATGAGAAAATCAATGAGGATTCTCCAACTC
CCTTTGCATATATACCTTTCGTCCATCAGGCCATTGAAGACACGAACAAAC
ATCTTGCTGGTTCCGAGTAAATGGTCTACGCCGTCTATACATGAATAACCC
GATTCTCCGTCGGGGTACGTATGCTCATGCACGTACATTTATTAATCAGT
TGAAGTTTATGTGGGTTATTGTTGCAGTATATGCCTAAATGGCCATTTCGG
CCTATATTTGTTGTCATTGTTCTGTCAGTAACTACCTAGTTTGGTGTGTAC
TCTCATTAGAGAGAAACTAAATGTACCAACTATTTGATGATTTGAATTTTC
TTTCCTGATAAAAAAA

SEQ. ID NO: 46
MARHGGSGLVGKLVTELEVYCDADKYYKIWKHHEDVPKAMPHMFTGVQPIK
GDGICSGSIKEWNYIIEGKAMRAMEESTHNDETRTISHRVVEGDLLKDYKK
FESINEINPKPNGNGCVVTWTAYEKINEDSPTPFAYIPFVHQAIEDTNKHL
AGSE

SEQ. ID NO: 47
CTTCAATAATCTCCAATCTATTGAGCAAAAATCCTCAACTACTTGATGGCT
CATCATGGTGTTTCGGGTTTAGTCGGGAAAGTTGTAACTGAATTGGAGCTC
AATTGCGATGCTGACGAATACTATAAAGTCTATAAGCACCATCAACTAGTA
CCAAATGAGGCAGTTTCTCATCTTTTCACTGGTGTTAAAGCTCTTGAAGGA
GGAGACGGCCTCAGTCCCGTTCATATCAAGGAATGGAGCTATATTCTTGAG
GGAAAGACAATGACCGCCGTGGAAGAATCAACATATGACGATGAAACAAGG
ACCATATCGCACCGCATCGTTGAAGGAGATGTTATGAAGGATTACAAGAAG
TTTGATGAGATCGTTGTAGCTAAACCAAAGCCTGATGGACATGGAAGCATT
GTATCCATATCTATAATGTATGAGAAAATAAACGAGGATTCTCCAACTCCA
TTTGACATCCTGAAAACTTTCCATCAGAACATTCTAGACCTAAGTGCTCAC
ATCTGTGCTTCCGAGTAAAATATCTCTCAAGTGTTTGGGTGTTACTTGTTG
TCATTTATGTGTGCGTTATTCATGCATGGACTATGCATGGCTTTGTAACCG
CAGTTTATCGCTTCTTTGATCATCTTTTTTTCTTTTTTTATACTTCTTTTT
TAAAGAAGTTTTGGCTCTATGTCCGTCCCTTGCTATTTTAATTTTTTGTTC
TTTGATCAGTAAATATTTTTGCTTAAAAAAAAAAACAATCATGAGCTACGTC
TATGT

SEQ. ID NO: 48
MAHHGVSGLVGKVVTELELNCDADEYYKVYKHHQLVPNEAVSHLFTGVKAL
EGGDGLSPVHIKEWSYILEGKTMTAVEESTYDDETRTISHRIVEGDVMKDY
KKFDEIVVAKPKPDGHGSIVSISIMYEKINEDSPTPFDILKTFHQNILDLS
AHICASE

SEQ. ID NO: 49
CAACAACTATCAGCTGGTCCAGCTGACCACTGTTTCTGCTGATGAACCTTA
AGGAACAAATTTCAGCAGAGAGATACAAGCTGAGGGTGTTATCAAATATTC
GACGTAGGAAGCGCTATCAAACCTGACTTTCATCCTTGAAATTAGAAGTTC
AAGTCTCCGCTTTAAGAATAATTAGTGATCCATTCAAAACTTCAACCGTGT
CTCCAAATGTCGCATTGTATGTGTCACCACAGTGAATTTCAGGTAAAATTT
TCAAATAAGACTGTTGATAGGATTCTCCTAAAAGGGGATTCAGAAAGTATG
ACTGTTAGATCAAGAAATTTCCAAAATAGAAAGGTCAACTTATAATTTCTA
GTGGTTATATCTTATCGCAATACTAGTGGTGGAAAGGTCAACTTATAATTT
CTGGGTGGATCTGGTTAACGATCGTTGCCGCCAATTACAGCTCACTATTG
AGTCATCAGTAGTTCAGCACAATTTCATCAATTCATTCCTGTAGTTGCAGG
TTGTTTAATTCTATATAAGCTCATGAAATATCAGTATTCATCTAAGGCAAG
AATCAGTATCAACTATCAGCAATGGCACATCACTATTCCACTTCCGGTCTA
GTTGGGAAACTTGTTACTGAAATGAGGTTAACTGCAACGCCGAAAACTAT
TACCAAATATTTAAGCAGCATGAAGGCGTTCCAAAAGCAATACCTCATATT
TTTACGAGCATGAAAGTTCTTGAGGGACATGGACTTACTTCCGGTTGTATC
AAGGAATGGCACTATCTTCATGAGGGAAAAGCACTCAAATTCAAGGAGACC
ACGACATATAACGATGAAGAAAGGACGATATGTCACAGCGTTATAGGAGGT
GACTTGTTGAATGATTACAAGAACTTCAGTGCGACACTTCTGGTTAAGGTT
AAGCCTATGGGTCATGGAACTACGTACCTGGCTCCGCCAGTGCAGCCAGCT
CCCAAGCAACATTTTAGCCAACCAGCCCAGCCGGCATCCAAGCATCATCAT
TTTAGCCTTCATAGGCCTCATTTAAACCAACCAGCACAGCCAGATTCCAAG
CATCATCTTAGTCTTCATAGGCCTCATTTAAACCTTTGCAAGACCATTTCA
CACTGCCCACTGACCGGCCGTGTCTTGGGTGTGCAAGATTCTTCCCCACCT
GCTCCTACCTACGTGGCTCCGCCAGTTCCTACATACGTGGCTCCGCCCATG
CATGGAAGCACTGTGATGTGGATTATAGATTATGAGAAGATCAATAAGGAT
TCTCCAATCCCCGTTCCTTATCTGGCTTTCTTCCATCAGATCATTGTAGAC
TTGAACTCTCACTTCTCCGCTTCTTATTAAATTATGGATAGATATGCATGC
CCACGGATTTATATATATGTATGCAACGACAATCACAGTGTCTTGTGTACG
ATATATGTGTGGAAATAAAAAACTATATATAAACGTGGTCATGCCAAAAAT
CTATTTTCGGCCTAATCAAGGCTTTACTTATTGCATGTGTATGAGTGGTTT
GTTTCATAATACTAGGGCATATGAATAAGTGAATGAATTATGTAAGTCATT
TGGATTGATTCTTTCATGTTATAATAAGATAAAAAACAAACATTCAGAATA
ATGTCGGCATCGTATGGGCCGCGACAGTGCATCACTAAG

SEQ. ID NO: 50
MAHHYSTSGLVGKLVTEMEVNCNAENYYQIFKQHEGVPKAIPHIFTSMKVL
EGHGLTSGCIKEWHYLHEGKALKFKETTTYNDEERTICHSVIGGDLLNDYK
NFSATLLVKVKPMGHGTTYLAPPVQPAPKQHFSQPAQPASKHHHFSLHRPH
LNQPAQPDSKHHLSLHRPHLNLCKTISHCPLTGRVLGVQDSSPPAPTYVAP
PVPTYVAPPMHGSTVMWIIDYEKINKDSPIPVPYLAFFHQIIVDLNSHFSA
SY

SEQ. ID NO: 51
CGATCATCCAAATATTTAGCTAAGCCAACAATTATAATTCAGTATCAATCA
CTATATCACTATCAGCAATGGCTCAGCCTCAATGTATTTCAGGTCTATCTG
GGAAACTTGTGACTAAATCAAATGTTAACTGCGGTGCCAACGATTTTTACA
CAATTTTTAAGCAGCATGTAGATGTTCCGAAAGCGATACCTCAAATTTACA
AGTGCGTGAAAGTTGTTGAGGGAGATGGAACTACTTCCGGTTGTATCAAGG
AATGGGATACCATTGTGAGGGTAAGGAACTGATTGTCAAGGAGAAAACGA
CATACACCGATGAAACAAGGACGATATGTCACTGCGTAGTAGGAGGAGACA
TAGCAAATGAGTACAAGAAATTTTATGCAATTCTTGTGGTTAATCCAAAGC
CTTGTGGTAATGGAAGCATTGTGAGTTGGACTGTTGATTACGAGAAGATTA
ATAAGGATTCTCCAATTCCTATTCCTTATATAGCTCTGTTCGCTCGGGTCA
TTGAAGGCTTGGACTCCTACCTCTGCGCTTATGCTTAAATTATCGATGGGT
TTGCATATATATCATGGGAGAATCCTAGGGTCCTGCAGATGGTAATAAAAC
TATAAATAAGCGTGGACTTGCCAAGATTCTACCTTCTACCTTATCATCAAG
GCTTACATATTGCATGTCTGCGTGGTTTGTTTCGTATTAAATGAATAAGTT

AATTATCCAAGTCGTTTGGAGTGTTTCTACTGTTTATAATGAACAAGTGAT
TTATCTAAGTCGTTTGAATTGTTTGTTTTTGTTTATTAAATTCTCATCATT
AAC

SEQ. ID NO: 52
MAQPQCISGLSGKLVTKSNVNCGANDFYTIFKQHVDVPKAIPQIYKCVKVV
EGDGTTSGCIKEWGYHCEGKELIVKEKTTYTDETRTICHCVVGGDIANEYK
KFYAILVVNPKPCGNGSIVSWTVDYEKINKDSPIPIPYIALFARVIEGLDS
YLCAYA

SEQ. ID NO: 53
ATGGCTCATCATGGTGTTTCAGGTCTAGTTGGGAAAATTGTAACTGAATTG
GAGGTGAATTGTAATGCCGACGAATTTTATAAGATTTTGAAGCGCGATGAA
GATGTTCCACGGGCAGTTTCTGATCTTTTCCCTCCCGTCAAAATTGCCAAA
GGAGATGGACTTGTTTCTGGTTGTATCAAGGAATGGGACTGTGTTCTTGAT
GGTAAGGCGATGAGCGGCAAGGAGGAAACAACACACAACGATGAAACGAGG
ACTTTGCGTCACCGTGAATTGGAAGGAGACTTGATGAAGGATTACAAGAAG
TTTGATTCCATAATTGAAGTTAATCCAAAACCAAATGGACATGGAAGCATT
GTGACGTGGTCAATTGAGTATGAGAAAATGAACGAAGATTCTCCGGCTCCC
TTTGCTTATCTAGCTTCCTTCCATCAGAACGTTGTGGAAGTTGATTCTCAC
CTCTGCCTTTCTGAATAA

SEQ. ID NO: 54
MAHHGVSGLVGKIVTELEVNCNADEFYKILKRDEDVPRAVSDLFPPVKIAK
GDGLVSGCIKEWDCVLDGKAMSGKEETTHNDETRTLRHRELEGDLMKDYKK
FDSIIEVNPKPNGHGSIVTWSIEYEKMNEDSPAPFAYLASFHQNVVEVDSH
LCLSE

SEQ. ID NO: 55
CTTCAATAATCTCCAATCTATTGAGCAAAAATCCTCAACTACTTGATGGCT
CATCATGGTGTTTCGGGTTTAGTCGGGAAAGTTGTAACTGAATTGGAGCTC
AATTGCGATGCTGACGAATACTATAAAGTCTATAAGCACCATCAACTAGTA
CCAAATGAGGCAGTTTCTCATCTTTTCACTGGTGTTAAAGCTCTTGAAGGA
GGAGACGGCCTCAGTCCCGTTCATATCAAGGAATGGAGCTATATTCTTGAG
GGAAAGACAATGACCGCCGTGGAAGAATCAACATATGACGATGAAACAAGG
ACCATATCGCACCGCATCGTTGAAGGAGATGTTATGAAGGATTACAAGAAG
TTTGATGAGATCGTTGTAGCTAAACCAAAGCCTGATGGACATGGAAGCATT
GTATCCATATCTATAATGTATGAGAAAATAAACGAGGATTCTCCAACTCCA

TTTGACATCCTGAAAACTTTCCATCAGAACATTCTAGACCTAAGTGCTCAC
ATCTGTGCTTCCGAGTAAAATATCTCTCAAGTGTTTGGGTGTTACTTGTTG
TCATTTATGTGTGCGTTATTCATGCATGGACTATGCATGGCTTTGTAACCG
CAGTTTATCGCTTCTTTGATCATCTTTTTTTCTTTTTTTATACTTCTTTTT
TAAAGAAGTTTTGGCTCTATGTCCGTCCCTTGCTATTTTAATTTTTTGTTC
TTTGATCAGTAAATATTTTTGCTTAAAAAAAAAACAATCATGAGCTACGTC
TATGT

SEQ. ID NO: 56
MMAHHGVSGLVGKVVTELELNCDADEYYKVYKHHQLVPNEAVSHLFTGVKA
LEGGDGLSPVHIKEWSYILEGKTMTAVEESTYDDETRTISHRIVEGDVMKD
YKKFDEIVVAKPKPDGHGSIVSISIMYEKINEDSPTPFDILKTFHQNILDL
SAHICASEYPYDVPDYA

SEQ. ID NO: 57
ATGGATTCTATTAATTCTTCCATATACTTCTGTGCATATTTTAGAGAACTA
ATCATCAAATTGTTGATGGCTCCTCTTGGTGTTTCAGGTTTAGTCGGGAAA
CTTTCAACTGAATTGGAGGTCGATTGCGATGCTGAAAAATATTATAACATG
TATAAGCACGGAGAAGATGTGCAAAAGGCAGTTCCTCATCTTTGCGTTGAC
GTCAAAGTTATCAGTGGAGATCCGACCAGTTCAGGTTGTATCAAGGAATGG
AATGTTAACATTGATGGTAAGACGATTCGCTCAGTAGAGGAAACAACACAC
AATGATGAAACGAAAACGTTGCGTCACCGTGTATTTGAAGGAGACATGATG
AAGGATTTCAAGAAGTTTGATACGATAATGGTAGTCAATCCAAAGCCGGAT
GGAAATGGATGTGTTGTGACACGGTCAATTGAGTATGAGAAAACCAACGAG
AATTCTCCGACTCCCTTTGATTATCTACAATTCGGCCATCAGGCCATTGAA
GACATGAACAAATACTTACGCGATTCTGAATAA

SEQ. ID NO: 58
MDSINSSIYFCAYFRELIIKLLMAPLGVSGLVGKLSTELEVDCDAEKYYNM
YKHGEDVQKAVPHLCVDVKVISGDPTSSGCIKEWNVNIDGKTIRSVEETTH
NDETKTLRHRVFEGDMMKDFKKFDTIMVVNPKPDGNGCVVTRSIEYEKTNE
NSPTPFDYLQFGHQAIEDMNKYLRDSE

SEQ. ID NO: 59
KGDGLVSGCIKEW

SEQ. ID NO: 60
EG

SEQ. ID NO: 61
PNGHGSIVTWSIEYEKMNEDSP

---

The invention claimed is:

1. A method of making a second morphinan compound having a saturated carbon bond at position C8-C14 and a mono-unsaturated carbon bond at position C7-C8, the method comprising:
   providing a host cell transformed with an expression construct comprising a nucleic acid sequence encoding neopinone isomerase and expressing the neopinone isomerase with a first morphinan compound having a mono-unsaturated carbon bond at position C8-C14 and a saturated carbon bond at position C7-C8
   under reaction conditions permitting the conversion of the first morphinan compound into the second morphinan compound;
   wherein the neopinone isomerase is a polypeptide encoded by:

(i) a nucleic acid molecule comprising a nucleic acid sequence of each of SEQ ID NO: 14, SEQ ID NO: 15, SEQ ID NO: 16, and SEQ ID NO: 17;
(ii) a nucleic acid molecule comprising a nucleic acid sequence having at least 90% identity to each of SEQ ID NO: 14, SEQ ID NO: 15, SEQ ID NO: 16 and SEQ ID NO: 17; or
(iii) a nucleic acid molecule comprising within the nucleic acid molecule a nucleic acid sequence having at least 90% identity to each of SEQ ID NO: 14, SEQ ID NO: 15, SEQ ID NO: 16 and SEQ ID NO: 17 but for the degeneration of the genetic code or
wherein the neopinone isomerase is:
(iv) a polypeptide comprising each of the amino acid sequences SEQ ID NO: 18, SEQ ID NO: 19, SEQ ID NO: 20, and SEQ ID NO: 21; or
(v) a polypeptide comprising within the polypeptide an amino acid sequence having at least 90% identity to each of the amino acid sequences SEQ ID NO: 18, SEQ ID NO: 19, SEQ ID NO: 20, and SEQ ID NO: 21.

2. The method according to claim 1, wherein the method further comprises isolating the second morphinan compound.

3. The method according to claim 1, wherein the first and second morphinan compounds possess a bridging oxygen atom between carbon atoms C4 and C5, forming a tetrahydrofuranyl ring within the morphinan chemical structure.

4. The method according to claim 1, wherein the first morphinan compound is a chemical compound having the chemical structure (I):

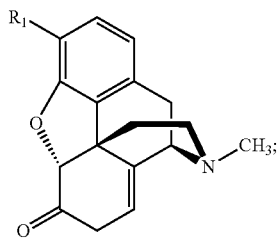

(I)

the second morphinan compound is a chemical compound having the chemical structure (II):

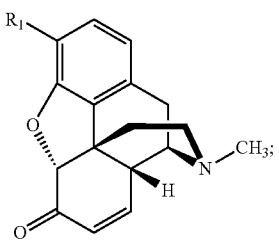

(II)

wherein R₁ is either a hydroxyl group or a methoxy group.

5. The method according to claim 4, the method further comprising transforming the host cell with an expression construct comprising a nucleic acid sequence encoding codeinone reductase and expressing the codeinone reductase,
wherein the R₁ of the second morphinan compound is a methoxy group, and
wherein reaction conditions permitting the conversion of the second morphinan compound into a third morphinan compound having the chemical structure (III):

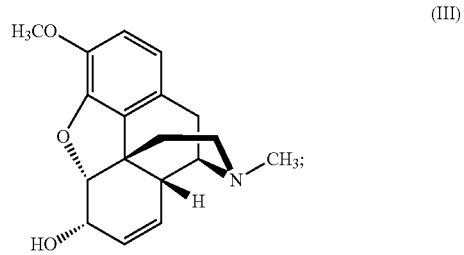

(III)

6. The method according to claim 5, wherein the method further comprises isolating the third morphinan compound having chemical structure (Ill).

7. The method according to claim 5, wherein additionally a fourth morphinan having the chemical structure (IV):

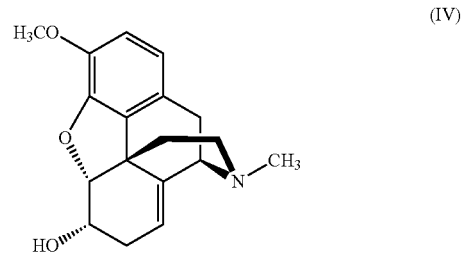

(IV)

is formed, and
wherein the quantity of compound (IV) upon completion of the reaction does constitute no more than 20% (w/w) of all morphinan compounds.

8. The method according to claim 7, wherein, compound (IV) upon completion of the reaction constitutes no more than 15%, 14%, 13%, 12%, 11%, 10%, 9%, 8%, 7%, 6%, 5%, 4%, 3%, 2% of 1% (w/w) of all morphinan compounds.

9. The method according claim 5, the method further comprising transforming the host cell with an expression construct comprising a nucleic acid sequence encoding codeinone-O-demethylase and expressing the codeinone-O-demethylase,
wherein reaction conditions permitting the conversion of the third morphinan compound into a fourth morphinan compound having the chemical structure (V):

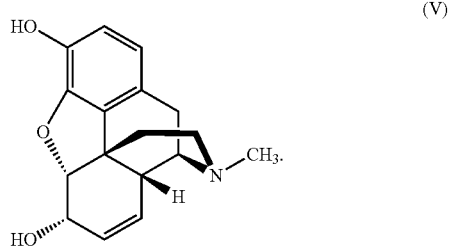

(V)

10. The method according to claim 9, wherein the method further comprises isolating the fourth morphinan compound having chemical structure (V).

* * * * *